United States Patent
Coffin

(10) Patent No.: US 10,947,513 B2
(45) Date of Patent: *Mar. 16, 2021

(54) ENGINEERED VIRUS

(71) Applicant: REPLIMUNE LIMITED, Oxford (GB)

(72) Inventor: Robert Coffin, Oxford (GB)

(73) Assignee: Replimune Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/068,830

(22) PCT Filed: Jan. 9, 2017

(86) PCT No.: PCT/GB2017/050038
§ 371 (c)(1),
(2) Date: Jul. 9, 2018

(87) PCT Pub. No.: WO2017/118866
PCT Pub. Date: Jul. 13, 2017

(65) Prior Publication Data
US 2019/0032024 A1  Jan. 31, 2019

(30) Foreign Application Priority Data

Jan. 8, 2016 (GB) ..................... 1600380
Jan. 8, 2016 (GB) ..................... 1600381
Jan. 8, 2016 (GB) ..................... 1600382

(51) Int. Cl.
| | | |
|---|---|---|
| *C12N 7/00* | (2006.01) | |
| *A61K 39/395* | (2006.01) | |
| *A61P 35/00* | (2006.01) | |
| *A61K 35/763* | (2015.01) | |
| *A61K 45/06* | (2006.01) | |
| *C07K 14/005* | (2006.01) | |
| *C07K 14/535* | (2006.01) | |
| *C07K 16/28* | (2006.01) | |
| *A61K 39/00* | (2006.01) | |

(52) U.S. Cl.
CPC ............ *C12N 7/00* (2013.01); *A61K 35/763* (2013.01); *A61K 39/3955* (2013.01); *A61K 39/39558* (2013.01); *A61K 45/06* (2013.01); *A61P 35/00* (2018.01); *C07K 14/005* (2013.01); *C07K 14/535* (2013.01); *C07K 16/2818* (2013.01); *A61K 2039/505* (2013.01); *C12N 2710/16621* (2013.01); *C12N 2710/16622* (2013.01); *C12N 2710/16632* (2013.01); *C12N 2710/16633* (2013.01); *C12N 2710/16643* (2013.01); *C12N 2740/13022* (2013.01)

(58) Field of Classification Search
CPC ............ C12N 7/00; C12N 15/86; C12N 2740/15051; C12N 2760/16034; C12N 7/02; C12N 2750/14011; C12N 2750/14023; C12N 2710/10043; C12N 15/861; C12N 2710/16632; C12N 2710/16643; C12N 2710/10332; A61P 35/00; A61K 39/3955; A61K 45/06; A61K 47/26; A61K 2039/5258; A61K 2039/5156; A61K 2039/572; A61K 2039/575; A61K 39/39558; A61K 35/763; A61K 35/761; A61K 35/765; A61K 35/768; A61K 48/0091; B01D 15/363; B01D 15/362; B01D 15/361; B01D 15/30; C07K 14/5434; G01N 33/56983; A61L 2202/22; A61L 2/0017; A61L 2/022
See application file for complete search history.

(56) References Cited

U.S. PATENT DOCUMENTS

| | | |
|---|---|---|
| 5,122,458 A | 6/1992 | Post et al. |
| 5,168,062 A | 12/1992 | Stinski |
| 5,288,641 A | 2/1994 | Roizman |
| 5,328,688 A | 7/1994 | Roizman |
| 5,385,839 A | 1/1995 | Stinski |
| 5,599,691 A | 2/1997 | Roizman |
| 5,602,007 A | 2/1997 | Dunn et al. |
| 5,698,531 A | 12/1997 | Nabel et al. |
| 5,824,318 A | 10/1998 | Mohr et al. |
| 5,846,707 A | 12/1998 | Roizman |
| 6,040,169 A | 3/2000 | Brown et al. |
| 6,071,692 A | 6/2000 | Roizman |
| 6,120,773 A | 9/2000 | Roizman |
| 6,172,047 B1 | 1/2001 | Roizman et al. |
| 6,297,219 B1 | 10/2001 | Nabel et al. |
| 6,340,673 B1 | 1/2002 | Roizman et al. |
| 6,423,528 B1 | 7/2002 | Brown et al. |

(Continued)

FOREIGN PATENT DOCUMENTS

| | | |
|---|---|---|
| WO | WO 2016/008976 | 1/1916 |
| WO | WO 2017/118866 | 7/1917 |

(Continued)

OTHER PUBLICATIONS

Loskog, Angelica, "Immunostimulatory Gene Therapy Using Oncolytic Viruses as Vehicles," *Viruses*, 2015, 7:5780-5791.

(Continued)

*Primary Examiner* — Bao Q Li

(74) *Attorney, Agent, or Firm* — Norton Rose Fulbright US LLP

(57) ABSTRACT

The present invention relates to oncolytic virus comprising: (i) a GM-CSF-encoding gene; and (ii) an immune co-stimulatory pathway activating molecule or an immune co-stimulatory pathway activating molecule-encoding gene.

26 Claims, 33 Drawing Sheets

Specification includes a Sequence Listing.

(56) References Cited

U.S. PATENT DOCUMENTS

| | | | |
|---|---|---|---|
| 6,428,968 | B1 | 8/2002 | Molnar-Kimber et al. |
| 6,649,157 | B2 | 11/2003 | Coffey et al. |
| 6,770,274 | B1 | 8/2004 | Martuza et al. |
| 7,063,835 | B2 | 6/2006 | Coffin |
| 7,223,593 | B2 | 5/2007 | Coffin |
| 7,537,924 | B2 | 5/2009 | Coffin |
| 7,749,745 | B2 | 7/2010 | Johnson et al. |
| 7,981,669 | B2 | 7/2011 | Coffin et al. |
| 8,273,568 | B2 | 9/2012 | Martuza et al. |
| 8,277,818 | B2 | 10/2012 | Coffin |
| 8,361,978 | B2 | 1/2013 | Rabkin et al. |
| 8,470,577 | B2 | 6/2013 | Johnson et al. |
| 8,679,830 | B2 | 3/2014 | Coffin et al. |
| 8,680,068 | B2 | 3/2014 | Coffin |
| 8,703,120 | B2 | 4/2014 | Martuza et al. |
| 8,871,193 | B2 | 10/2014 | Johnson et al. |
| 8,986,672 | B2 | 3/2015 | Zhang et al. |
| 9,827,307 | B2 | 11/2017 | Rabkin et al. |
| 9,868,961 | B2 | 1/2018 | Beauchamp |
| 10,039,796 | B2 | 8/2018 | Zhang et al. |
| 10,301,600 | B2 | 5/2019 | Coffin |
| 2003/0091537 | A1 † | 5/2003 | Coffin |
| 2008/0014175 | A1 | 1/2008 | Hallahan et al. |
| 2010/0297072 | A1 | 11/2010 | DePinho |
| 2014/0154216 | A1 | 6/2014 | Coffin |
| 2014/0271677 | A1 | 9/2014 | Palese et al. |
| 2015/0232812 | A1 | 8/2015 | Coffin |

FOREIGN PATENT DOCUMENTS

| | | |
|---|---|---|
| WO | WO 97/12623 | 4/1997 |
| WO | WO 01/53505 | 7/2001 |
| WO | WO 01/53506 | 7/2001 |
| WO | WO 2006/002394 | 1/2006 |
| WO | 2007/052029 A1 † | 5/2007 |
| WO | WO 2007/123737 | 11/2007 |
| WO | WO 2014/022138 | 2/2014 |
| WO | WO 2014/036412 | 3/2014 |
| WO | WO 2014/066532 | 5/2014 |
| WO | 2015/077624 A1 † | 5/2015 |

OTHER PUBLICATIONS

Office Action issued Corresponding European Patent Application No. 1770385, dated May 21, 2019.

Robbins, Paul D., et al; "Viral Vectors for Gene Therapy"; Pharmacol, Ther.; vol. 80, No. 1; pp. 35-47; 1998.

Allison, et al; "For Their Discovery of Cancer Therapy by Inhibition of Negative Immune Regulation"; The Nobel Assembly at Karolinska Institutet; 2018 Nobel Prize in Physiology of Medicine.

Cell Signaling Technology; Immune Checkpoint Signaling in the Tumor Microenvironment; Mar. 2018.

Chou et al., "Mapping of Herpes Simplex Virus-1 Neurovirulence to $\gamma_1 34.5$, a Gene Nonessential for Growth in Culture," *Science*, 1990, 250(4985):1262-1266.

Du et al., "Tumor-specific oncolytic adenoviruses expressing granulocyte macrophage colony-stimulating factor or anti-CTLA4 antibody for the treatment of cancers," *Cancer Gene Therapy*, 2014, 21(8):340-348.

Gangi et al., "The safety of talimogene laherparepvec for the treatment of advanced melanoma," *Expert Opinion on Drug Safety*, 2016, pp. 1-5.

Gibney et al., "Preliminary results from a phase ½ study of INCB024360 combined with ipilimumab (ipi) in patients (pts) with melanoma." 2014 ASCO Annual Meeting, No. 3010.

International Search Report and Written Opinion issued in International Patent Application No. PCT/GB2017/050038, dated Apr. 24, 2017.

Liu et al., "ICP34.5 deleted herpes simplex cirus with enhanced oncolytic, immune stimulating, and anti-tumour properties," *Gene Therapy*, 2003, 10(4):292-303.

Maclean et al., "Herpes simplex cirus type 1 deletion variants 1714 and 1716 pinpoint neurovirulence-related sequences in Glasgow strain 17 + between immediate early gene 1 and the 'a' sequence," *Journal of General Virology*, 1991, 72:631-639.

Piasecki et al., "Talimogene laherparepvec increases the anti-tumor efficacy of the anti-PD-1 immune checkpoint blockade," *AACR Annual Meeting Presentation Abstract*, Apr. 19, 2015.

Reese, "Abstract IA24: New frontiers in oncolytic virus therapy," *Cancer Immunology Research*, 2016, 4(11):1A24-1A24.

Robinson et al., "Novel Immunocompetent Murine Tumor Model for Evaluation of Conditionally Replication-Competent (Oncolytic) Murine Adenoviral Vectors," *Journal of Virology*, 2009, 83(8):3450-3462.

Senzer et al., "Phase II Clinical Trial of a Granulocyte-Macrophage Colony-Stimulating Factor-Encoding, Second-Generation Oncolytic herpesvirus in Patients with Unresectable Metastatic Melanoma" *Journal of Clinical Oncology*, 2009, 27(34):5763-5771.

Simpson et al., "Combination of a Fusogenic Glycoprotein, Prodrug activation, and Oncolytic Herpes Simplex Virus for Enhanced Local Tumor Control," *Cancer Research*, 2006, 66(9):4835-4842.

Sokolowski et al., "Oncolytic virotherapy using herpes simplex virus: how far have we come?" *Oncolytic Virotherapy*, 2015, 4:207-219.

Yan et al., "Developing Novel Oncolytic Adenoviruses through Bioselection," *Journal of Virology*, 2003, 77(4):2640-2650.

Todo, Tomoki, "Armed" oncolytic herpes simplex viruses for brain tumor therapy, pp. 208-213, Jul./Aug. Sep. 2008.†

† cited by third party

Cell death assessed by crystal violet staining: low magnification

Virus: 5 injections of 5x10⁶ pfu into the right flank tumor only
Anti-PD1: 10mg/kg i.p. Q3Dx9 (clone RMP1-14; BioXCell)

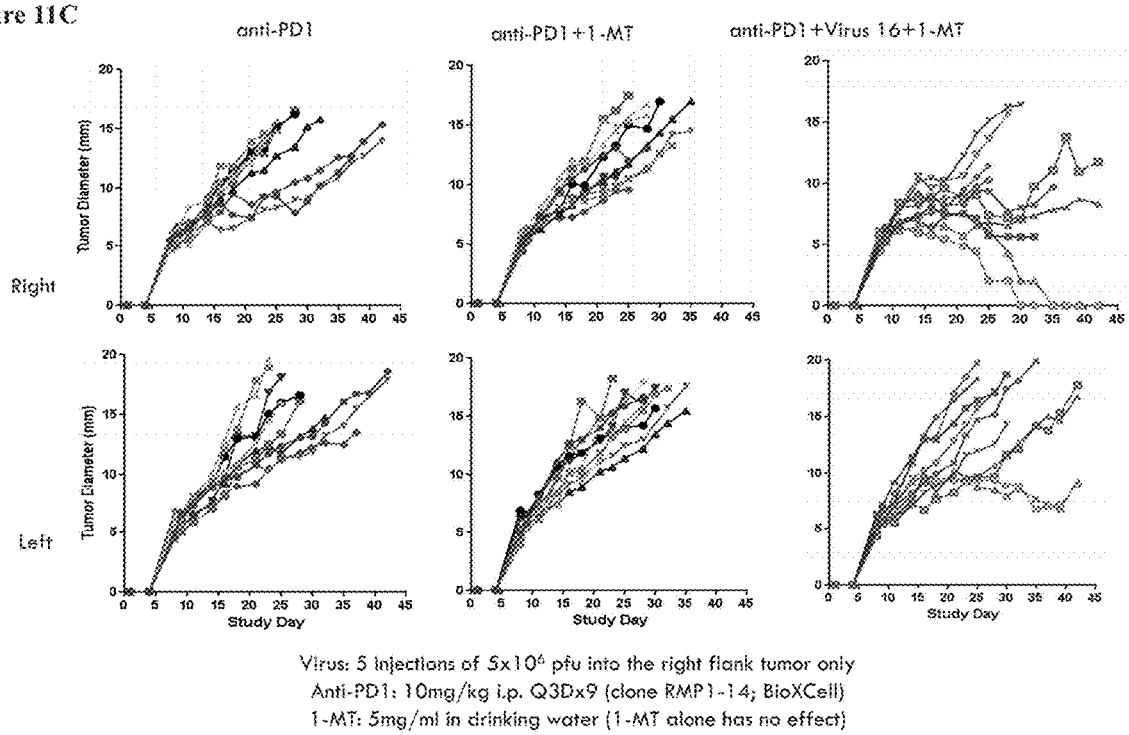

Human A549 lung cancer tumors in nude mice (no immune effect)
3 injections of Virus 16 or Virus 19 over 1 wk of vehicle or the indicated dose of virus (N=10/group)

Rat 9L glioma tumors in immune competent rats
Virus: $5 \times 10^5$ pfu injected 3x/wk into the right tumor only for 3 wks Mouse A20 tumors in immune competent mice (dual flank tumors)
Viruses: 5x10⁴ pfu of the indicated virus injected 3x into the right tumor only

ENGINEERED VIRUS

CROSS-REFERENCE TO RELATED APPLICATION

This application is a national phase under 35 U.S.C. § 371 of International Application No. PCT/GB2017/050038, filed Jan. 9, 2017, which claims the benefit of priority to Great Britain Patent Application Serial Nos. 1600380.8, 1600381.6, and 1600382.4, all filed Jan. 8, 2016, the entire contents of each of which are hereby incorporated by reference in their entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself and enhanced due to the recognition by the host of so called damage associated molecular patterns (DAMPs) which aid in the activation of the immune response.

Viruses also engage with various mediators of the innate immune response as part of the host response to the recognition of a viral infection through e.g. toll-like receptors and cGAS/STING signalling and the recognition of pathogen associated molecular patterns (PAMPs) resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micro-metastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to induce immune responses or increase the immunogenicity of antigens released following virus replication and cell death, genes intended to shape the immune response which is generated, genes to increase the general immune activation status of the tumor, or genes to increase the direct oncolytic properties (i.e. cytotoxic effects) of the virus. Importantly, viruses have the ability to deliver encoded molecules which are intended to help to initiate, enhance or shape the systemic anti-tumor immune response directly and selectively to tumors, which may have benefits of e.g. reduced toxicity or of focusing beneficial effects on tumors (including those not infected by the virus) rather than off-target effects on normal (i.e. non-cancerous) tissues as compared to the systemic administration of these same molecules or systemic administration of other molecules targeting the same pathways.

It has been demonstrated that a number of viruses including, for example, herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models. Clinical trials of ICP34.5 deleted, or ICP34.5 and ICP6 deleted, HSV have also shown safety and selective replication in tumor tissue in humans.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. GM-CSF is a pro-inflammatory cytokine which has multiple functions including the stimulation of monocytes to exit the circulation and migrate into tissue where they proliferate and mature into macrophages and dendritic cells. GM-CSF is important for the proliferation and maturation of antigen presenting cells, the activity of which is needed for the activation of an anti-tumor immune response. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy are clearly needed.

Recently it has been shown that oncolytic immunotherapy can result in additive or synergistic therapeutic effects in conjunction with immune checkpoint blockade (i.e. inhibition or 'antagonism' of immune checkpoint pathways, also termed immune co-inhibitory pathways). Checkpoint (immune inhibitory pathway) blockade is intended to block host immune inhibitory mechanisms which usually serve to prevent the occurrence of auto-immunity. However, in cancer patients these mechanisms can also serve to inhibit the induction of or block the potentially beneficial effects of any immune responses induced to tumors.

Systemic blockade of these pathways by agents targeting CTLA-4, PD-1 or PD-L1 have shown efficacy in a number of tumor types, including melanoma and lung cancer. However, unsurprisingly, based on the mechanism of action, off target toxicity can occur due to the induction of auto-immunity. Even so, these agents are sufficiently tolerable to provide considerable clinical utility. Other immune co-inhibitory pathway and related targets for which agents (mainly antibodies) are in development include LAG-3, TIM-3, VISTA, CSF1R, IDO, CEACAM1, CD47. Optimal clinical activity of these agents, for example PD1, PDL1, LAG-3, TIM-3, VISTA, CSF1R, IDO, CD47, CEACAM1, may require systemic administration or presence in all tumors due to the mechanism of action, i.e. including targeting of the interface of immune effector cells with tumors or other immune inhibitory mechanisms in/of tumors. In some cases, more localised presence in e.g. just some tumors or in some lymph nodes may also be optimally effective, for example agents targeting CTLA-4.

An alternative approach to increasing the anti-tumor immune response in cancer patients is to target (activate) immune co-stimulatory pathways, i.e. in contrast to inhibiting immune co-inhibitory pathways. These pathways send activating signals into T cells and other immune cells, usually resulting from the interaction of the relevant ligands on antigen presenting cells (APCs) and the relevant receptors on the surface of T cells and other immune cells. These signals, depending on the ligand/receptor, can result in the increased activation of T cells and/or APCs and/or NK cells and/or B cells, including particular subtypes, increased differentiation and proliferation of T cells and/or APCs and/or NK cells and/or B cells, including particular subtypes, or suppression of the activity of immune inhibitory T cells such as regulatory T cells. Activation of these pathways would therefore be expected to result in enhanced anti-tumor immune responses, but it might also be expected that systemic activation of these pathways, i.e. activation of immune responses generally rather than anti-tumor immune responses specifically or selectively, would result in considerable off target toxicity in non-tumor tissue, the degree of such off target toxicity depending on the particular immune co-stimulatory pathway being targeted. Nevertheless agents (mainly agonistic antibodies, or less frequently the soluble ligand to the receptor in question) targeting immune co-stimulatory pathways, including agents targeting GITR, 4-1-BB, OX40, CD40 or ICOS, and intended for systemic use (i.e. intravenous delivery) are in or have been proposed for clinical development.

For many of these approaches targeting immune co-inhibitory or co-inhibitory pathways to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed. Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the optimal activity of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely explains the promising combined anti-tumor effects of oncolytic agents and immune co-inhibitory pathway blockade in mice and humans that have so far been observed.

The above discussion demonstrates that there is still much scope for improving oncolytic agents and cancer therapies utilising oncolytic agents, anti-tumor immune responses and drugs which target immune co-inhibitory or co-stimulatory pathways.

SUMMARY OF THE INVENTION

The invention provides oncolytic viruses expressing GM-CSF and at least one molecule targeting an immune co-stimulatory pathway. GM-CSF aids in the induction of an inflammatory tumor micro-environment and stimulates the proliferation and maturation of antigen presenting cells, including dendritic cells, aiding the induction of an anti-tumor immune responses. These immune responses are amplified through activation of an immune co-stimulatory pathway or pathways using an immune co-stimulatory pathway activating molecule or molecules also delivered by the oncolytic virus.

The use of an oncolytic virus to deliver molecules targeting immune co-stimulatory pathways to tumors focuses the amplification of immune effects on anti-tumor immune responses, and reduces the amplification of immune responses to non-tumor antigens. Thus, immune cells in tumors and tumor draining lymph nodes are selectively engaged by the molecules activating immune co-stimulatory pathways rather than immune cells in general. This results in enhanced efficacy of immune co-stimulatory pathway activation and anti-tumor immune response amplification, and can also result in reduced off target toxicity. It is also important for focusing the effects of combined systemic immune co-inhibitory pathway blockade and immune co-stimulatory pathway activation on tumors, i.e. such that the amplified immune responses from which co-inhibitory blocks are released are antitumor immune responses rather than responses to non-tumor antigens.

The invention utilizes the fact that, when delivered by an oncolytic virus, the site of action of co-stimulatory pathway activation and of GM-CSF expression is in the tumor and/or tumor draining lymph node, but the results of such activation (an amplified systemic anti-tumor-immune response) are systemic. This targets tumors generally, and not only tumors to which the oncolytic virus has delivered the molecule or molecules targeting an immune co-stimulatory pathway or pathways and GM-CSF. Oncolytic viruses of the invention therefore provide improved treatment of cancer through the generation of improved tumor focused immune responses. The oncolytic virus of the invention also offers improved anti-tumor immune stimulating effects such that the immune-mediated effects on tumors which are not destroyed by oncolysis, including micro-metastatic disease, are enhanced, resulting in more effective destruction of these tumors, and more effective long term anti-tumor vaccination to prevent future relapse and improve overall survival.

Anti-tumor efficacy is improved when an oncolytic virus of the invention is used as a single agent and also when the virus is used in combination with other anti-cancer modalities, including chemotherapy, treatment with targeted agents, radiation and, in preferred embodiments, immune checkpoint blockade drugs (i.e. antagonists of an immune co-inhibitory pathway) and/or agonists of an immune co-stimulatory pathway.

Accordingly, the present invention provides an oncolytic virus comprising: (i) a GM-CSF-encoding gene; and (ii) an immune co-stimulatory pathway activating molecule or immune co-stimulatory pathway activating molecule-encoding gene. The virus may encode more than one immune co-stimulatory pathway activating molecule/gene.

The immune co-stimulatory pathway activating molecule is preferably GITRL, 4-1-BBL, OX40L, ICOSL or CD40L or a modified version of any thereof or a protein capable of blocking signaling through CTLA-4, for example an antibody which binds CTLA-4. Examples of modified versions include agonists of a co-stimulatory pathway that are secreted rather than being membrane bound, and/or agonists modified such that multimers of the protein are formed.

The virus may be a modified clinical isolate, such as a modified clinical isolate of a virus, wherein the clinical isolate kills two or more tumor cell lines more rapidly and/or at a lower dose in vitro than one or more reference clinical isolates of the same species of virus.

The virus is preferably a herpes simplex virus (HSV), such as HSV1. The HSV typically does not express functional ICP34.5 and/or functional ICP47 and/or expresses the US11 gene as an immediate early gene.

The invention also provides:
a pharmaceutical composition comprising a virus of the invention and a pharmaceutically acceptable carrier or diluent;
the virus of the invention for use in a method of treating the human or animal body by therapy;
the virus of the invention for use in a method of treating cancer, wherein the method optionally comprises administering a further anti-cancer agent;
a product of manufacture comprising a virus of the invention in a sterile vial, ampoule or syringe;
a method of treating cancer, which comprises administering a therapeutically effective amount of a virus or a pharmaceutical composition of the invention to a patient in need thereof, wherein the method optionally comprises administering a further anti-cancer agent which is optionally an antagonist of an immune co-inhibitory pathway, or an agonist of an immune co-stimulatory pathway;
use of a virus of the invention in the manufacture of a medicament for use in a method of treating cancer, wherein the method optionally comprises administering a further anti-cancer agent which is optionally an antagonist of an immune co-inhibitory pathway, or an agonist of an immune co-stimulatory pathway;
a method of treating cancer, which comprises administering a therapeutically effective amount of an oncolytic virus, an inhibitor of the indoleamine 2,3-dioxygenase (IDO) pathway and a further antagonist of an immune co-inhibitory pathway, or an agonist of an immune co-stimulatory pathway to a patient in need thereof.

BRIEF DESCRIPTION OF THE FIGURES

FIG. 11 shows the antitumor effects of Virus 16 in Balb/c mice harboring mouse CT26 tumors in the left and right flanks. Groups of 10 mice were then treated with: Vehicle (3 injections into right flank tumors every other day); 5×10exp6 pfu of Virus 16 (mRP1) injected in the right flank tumor every other day; anti-mouse PD1 alone (10 mg/kg i.p. every three days, BioXCell clone RMP1-14); anti-mouse CTLA-4 (3 mg/kg i.p every three days, BioXCell clone 9D9); anti-mouse PD1 together with Virus 16; anti-mouse CTLA4 together with Virus 16; 1-methyl trypotophan (I-MT; IDO inhibitor (5 mg/ml in drinking water)); anti-mouse PD1 together with 1-methyl trypotophan; or anti-mouse PD1 together with 1-methyl trypotophan and Virus 16. Effects on tumor size were observed for a further 30 days. Greater tumor reduction was seen in animals treated with combinations of virus and checkpoint blockade than with the single treatment groups. FIG. 11C shows that enhanced tumor reduction was observed using Virus 16 together with both anti-PD1 and IDO inhibition as compared to anti-PD1 and 1-MT inhibition in the absence of the virus.

BRIEF DESCRIPTION OF THE SEQUENCE LISTING

Figure 1:
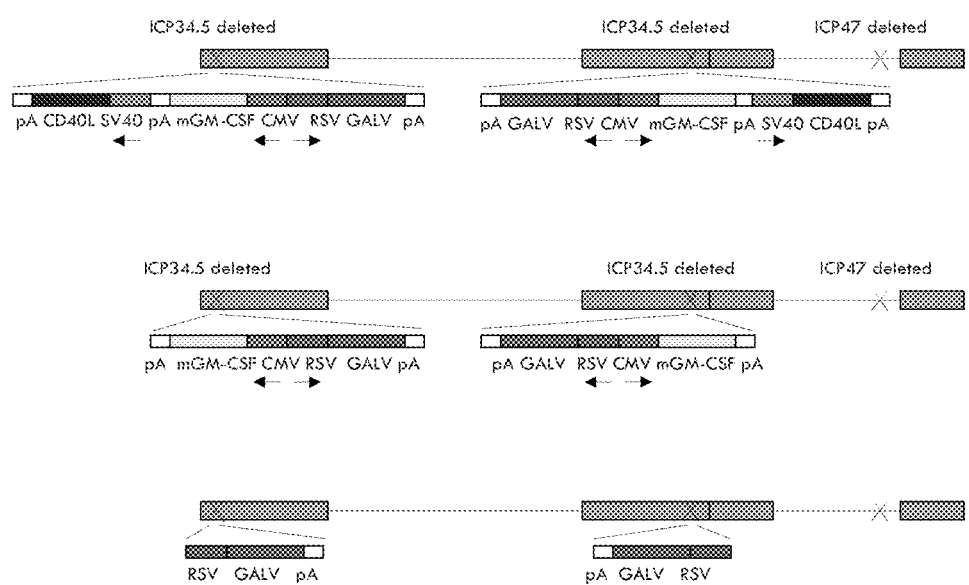
FIG. 1 depicts the structure of an exemplary virus of the invention that comprises a gene encoding GM-CSF and a gene encoding CD40L.

SEQ ID NO: 1 is the nucleotide sequence of mouse GM-CSF.
SEQ ID NO: 2 is the nucleotide sequence of a codon optimized version of mouse GM-CSF.
SEQ ID NO: 3 is the nucleotide sequence of human GM-CSF.
SEQ ID NO: 4 is the nucleotide sequence of a codon optimized version of human GM-CSF.
SEQ ID NO: 5 is the amino acid sequence of mouse GM-CSF.
SEQ ID NO: 6 is the amino acid sequence of human GM-CSF.
SEQ ID NO: 7 is the nucleotide sequence of GALV-R-.
SEQ ID NO: 8 is the nucleotide sequence of a codon optimized version of GALV-R- (the first three nucleotides are optional)
SEQ ID NO: 9 is the amino acid sequence of GALV-R-.
SEQ ID NO: 10 is the nucleotide sequence of a codon optimized version of a human membrane bound version of CD40L.
SEQ ID NO: 11 is the amino acid sequence of a human membrane bound version of CD40L.
SEQ ID NO: 12 is the nucleotide sequence of a codon optimized version of a multimeric secreted version of human CD40L.
SEQ ID NO: 13 is the amino acid sequence of a multimeric secreted version of human CD40L.
SEQ ID NO: 14 is the nucleotide sequence of a codon optimized version of a multimeric secreted version of mouse CD40L.
SEQ ID NO: 15 is the amino acid sequence of a multimeric secreted version of mouse CD40L.
SEQ ID NO: 16 is a codon optimized version of the nucleotide sequence of wild-type human CD40L.
SEQ ID NO: 17 is the amino acid sequence of wild-type human CD40L.
SEQ ID NO: 18 is a codon optimized version of the nucleotide sequence of wild-type mouse CD40L.
SEQ ID NO: 19 is the amino acid sequence of wild-type mouse CD40L.
SEQ ID NO: 20 is the nucleotide sequence of a codon optimized version of murine 4-1BBL.
SEQ ID NO: 21 is the nucleotide sequence of a codon optimized version of human 4-1BBL.
SEQ ID NO: 22 is the nucleotide sequence of a codon optimized version of secreted mouse 4-1BBL.
SEQ ID NO: 23 is the nucleotide sequence of a codon optimized version of human secreted 4-1BBL.
SEQ ID NO: 24 is the nucleotide sequence of a codon optimized version of murine GITRL.
SEQ ID NO: 25 is the nucleotide sequence of a codon optimized version of human GITRL.
SEQ ID NO: 26 is the nucleotide sequence of a codon optimized version of secreted murine GITRL.
SEQ ID NO: 27 is the nucleotide sequence of a codon optimized version of secreted human GITRL.
SEQ ID NO: 28 is the nucleotide sequence of a codon optimized version of murine OX40L.
SEQ ID NO: 29 is the nucleotide sequence of a codon optimized version of human OX40L.
SEQ ID NO: 30 is the nucleotide sequence of a codon optimized version of secreted murine OX40L.
SEQ ID NO: 31 is the nucleotide sequence of a codon optimized version of secreted human OX40L.
SEQ ID NO: 32 is the nucleotide sequence of a codon optimized version of murine ICOSL.
SEQ ID NO: 33 is the nucleotide sequence of a codon optimized version of human ICOSL.
SEQ ID NO: 34 is the nucleotide sequence of a murine scFv CTLA-4 antibody. The first six and last eight nucleotides are restriction sites added for cloning purposes.
SEQ ID NO: 35 is the nucleotide sequence of a murine scFv CTLA-4 antibody. The first six and last eight nucleotides are restriction sites added for cloning purposes.
SEQ ID NO: 36 is the nucleotide sequence of the CMV promoter.
SEQ ID NO: 37 is the nucleotide sequence of the RSV promoter.
SEQ ID NO: 38 is the nucleotide sequence of BGH polyA.
SEQ ID NO: 39 is the nucleotide sequence of SV40 late polyA.
SEQ ID NO: 40 is the nucleotide sequence of the SV40 enhancer promoter.
SEQ ID NO: 41 is the nucleotide sequence of rabbit beta-globulin (RBG) polyA.
SEQ ID NO: 42 is the nucleotide sequence of GFP.
SEQ ID NO: 43 is the nucleotide sequence of the MoMuLV LTR promoter.

SEQ ID NO: 44 is the nucleotide sequence of the EF1a promoter.

SEQ ID NO: 45 is the nucleotide sequence of HGH polyA.

DETAILED DESCRIPTION OF THE INVENTION

Oncolytic Virus

The virus of the invention is oncolytic. An oncolytic virus is a virus that infects and replicates in tumor cells, such that the tumor cells are killed. Therefore, the virus of the invention is replication competent. Preferably, the virus is selectively replication competent in tumor tissue. A virus is selectively replication competent in tumor tissue if it replicates more effectively in tumor tissue than in non-tumor tissue. The ability of a virus to replicate in different tissue types can be determined using standard techniques in the art.

The virus of the invention may be any virus which has these properties, including a herpes virus, pox virus, adenovirus, retrovirus, rhabdovirus, paramyxovirus or reovirus, or any species or strain within these larger groups. Viruses of the invention may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. In particularly preferred embodiments the virus of the invention is based on a clinical isolate of the virus species to be used. The clinical isolate may have been selected on the basis of it having particular advantageous properties for the treatment of cancer.

The clinical isolate may have surprisingly good anti-tumor effects compared to other strains of the same virus isolated from other patients, wherein a patient is an individual harbouring the virus species to be tested. The virus strains used for comparison to identify viruses of the invention may be isolated from a patient or an otherwise healthy (i.e. other than harboring the virus species to be tested) volunteer, preferably an otherwise healthy volunteer. HSV1 strains used to identify a virus of the invention are typically isolated from cold sores of individuals harboring HSV1, typically by taking a swab using e.g. Virocult (Sigma) brand swab/container containing transport media followed by transport to the facility to be used for further testing.

After isolation of viruses to be compared from individuals, stocks of the viruses are typically prepared, for example by growing the isolated viruses on BHK or vero cells. Preferably, this is done following no more than 3 cycles of freeze thaw between taking the sample and it being grown on, for example, BHK or vero cells to prepare the virus stock for further use. More preferably the virus sample has undergone 2 or less than 2 cycles of freeze thaw prior to preparation of the stock for further use, more preferably one cycle of freeze thaw, most preferably no cycles of freeze thaw. Lysates from the cell lines infected with the viruses prepared in this way after isolation are compared, typically by testing for the ability of the virus to kill tumor cell lines in vitro. Alternatively, the viral stocks may be stored under suitable conditions, for example by freezing, prior to testing. Viruses of the invention have surprisingly good anti-tumor effects compared to other strains of the same virus isolated from other individuals, preferably when compared to those isolated from >5 individuals, more preferably >10 other individuals, most preferably >20 other individuals.

The stocks of the clinical isolates identified for modification to produce viruses of the invention (i.e. having surprisingly good properties for the killing of tumor cells as compared to other viral strains to which they were compared) may be stored under suitable conditions, before or after modification, and used to generate further stocks as appropriate.

A clinical isolate is a strain of a virus species which has been isolated from its natural host. The clinical isolate has preferably been isolated for the purposes of testing and comparing the clinical isolate with other clinical isolates of that virus species for a desired property, in the case of viruses of the invention that being the ability to kill human tumor cells. Clinical isolates which may be used for comparison also include those from clinical samples present in clinical repositories, i.e. previously collected for clinical diagnostic or other purposes. In either case the clinical isolates used for comparison and identification of viruses of the invention will preferably have undergone minimal culture in vitro prior to being tested for the desired property, preferably having only undergone sufficient culture to enable generation of sufficient stocks for comparative testing purposes. As such, the viruses used for comparison to identify viruses of the invention may also include deposited strains, wherein the deposited strain has been isolated from a patient, preferably an HSV1 strain isolated from the cold sore of a patient.

The virus may be a modified clinical isolate, wherein the clinical isolate kills two or more tumor cell lines more rapidly and/or at a lower dose in vitro than one or more reference clinical isolate of the same species of virus. Typically, the clinical isolate will kill two or more tumor cell lines within 72 hours, preferably within 48 hours, more preferably within 24 hours, of infection at multiplicities of infection (MOI) of less than or equal to 0.1, preferably less than or equal to an MOI of 0.01, more preferably less than or equal to an MOI of 0.001. Preferably the clinical isolate will kill a broad range of tumor cell lines, such as 2, 3, 4, 5, 6, 7, 8, 9, 10 or, for example, all of the following human tumor cell lines: U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), HT1080 (fibrosarcoma).

Thus, the virus of the invention may be capable of killing cells from two or more, such as 3, 4, 5, 6, 7 or more, different types of tumor such as two or more, such as 3, 4, 5, 6, 7 or more, solid tumors, including but not limited to colorectal tumor cells, prostate tumor cells, breast tumor cells, ovarian tumor cells, melanoma cells, squamous cell carcinoma cells, lung tumor cells, pancreatic tumor cells, sarcoma cells and/or fibrosarcoma cells.

Tumor cell line killing can be determined by any suitable method. Typically, a sample is first isolated from a patient, preferably, in the case of HSV1, from a cold sore, is used to infect BHK cells, or another suitable cell line such as vero cells. Positive samples are typically identified by the presence of a cytopathic effect (CPE) 24-72 hours post infection, such as 48 hours post infection, and confirmed to be the target viral species by, for example, immunohistochemistry or PCR. Viral stocks are then generated from the positive samples. A sample from the viral stock is typically tested and compared to other samples generated in the same way using swabs from different patients. Testing may be carried out by determining the level of CPE achieved at a range of multiplicity of infection (MOI) and at various times post infection.

For example, cell lines at 80% confluency may be infected with the viral sample at MOI of 1, 0.1, 0.01 and 0.001 and duplicate plates incubated for 24 and 48 hours at 37° C., 5% $CO_2$ prior to determination of the extent of viral cell killing. This may be determined by, for example, fixing the cells with glutaraldehyde and staining with crystal violet using standard methods. The level of cell lysis may then be assessed by standard methods such as gross observation, microscopy (cell counts) and photography. The method may be repeated with the cells being incubated for shorter time periods, such as 8, 12 or 16 hours, or longer time periods, such as 72 hours, before cell killing is determined, or at additional MOIs such as 0.0001 or less.

Growth curve experiments may also be conducted to assess the abilities of different clinical isolates to replicate in tumor cell lines in vitro. For example, cell lines at 80% confluency may be infected with the viral sample at MOI of 1, 0.1, 0.01 and 0.001 are incubated at 37° C., 5% $CO_2$ and the cells lysed, typically by freeze/thawing, at 0, 8, 16, 24 and 48 hours post infection prior to determination of the extent of viral cell killing. This may be determined by, for example, assessing viral titres by a standard plaque assay.

A clinical isolate of the invention can kill infected tumor cell lines more rapidly and/or at a lower MOI than the other clinical isolates to which it is compared, preferably 2, 3, 4, 5 or 10 or more, other clinical isolates of the same virus species. The clinical isolate of the invention typically kills a 10%, 25% or 50% greater proportion of the tumor cells present at a particular MOI and time point than at least one, preferably 2, 3, 4, 5 or 10 or more, other clinical isolates of the same virus type at the same MOI and time point to which it was compared. The clinical isolate of the invention typically kills the same or a greater proportion of tumor cells at a MOI that is half or less than half that of the MOI at which one or more, preferably 2, 3, 4, 5, 10 or 15 or more, other clinical isolates of the same virus species used for the comparison at the same time point, typically at 12, 24 and/or 48 hours, kills the same proportion of tumor cells. Preferably, a clinical isolate of the invention typically kills the same or a greater proportion of tumor cells at a MOI that is 5 or 10 times lower than the MOI at which one or more, preferably 2, 3, 4, 5, 10 or 15 or more, other clinical isolates of the same virus used for the comparison at the same time point, typically at 12, 24 and/or 48 hours kills the same proportion of tumor cells. The improved tumor cell killing abilities of a virus of the invention are typically achieved compared to at least 50%, 75% or 90% of the other clinical isolates of the same viral species used for the comparison. The virus is preferably compared to at least 4 other virus strains, such as, for example, 7, 9, 19, 39 or 49 other virus strains of the same species.

The isolated strains may be tested in batches, for example of 4-8 viral strains at a time, on, for example, 4-8 of the tumor cell lines at a time. For each batch of experiments, the degree of killing achieved is ranked on each cell line for the best (i.e. least surviving cells at each time point/MOI) to the worst (i.e. most surviving cells for each time point/MOI) for the viruses being compared in that experiment. The virus strains from each experiment which perform the best across the range of tumor cell line tested (i.e. that consistently ranked as one of the best at killing the cell lines) may then be compared head to head in further experiments using other clinical isolates and/ore other tumor cell lines to identify the best virus strains in the total of, for example, >20 virus strains sampled. Those ranked as the best overall are the viruses of the invention.

In a preferred embodiment, the virus of the invention is a strain selected from:
  strain RH018A having the provisional accession number ECCAC 16121904;
  strain RH004A having the provisional accession number ECCAC 16121902;
  strain RH031A having the provisional accession number ECCAC 16121907;
  strain RH040B having the provisional accession number ECCAC 16121908;
  strain RH015A having the provisional accession number ECCAC 16121903;
  strain RH021A having the provisional accession number ECCAC 16121905;
  strain RH023A having the provisional accession number ECCAC 16121906; and
  strain RH047A having the provisional accession number ECCAC 16121909.

More preferably, the virus of the invention is a strain selected from:
  strain RH018A having the provisional accession number ECCAC 16121904;
  strain RH004A having the provisional accession number ECCAC 16121902;
  strain RH031A having the provisional accession number ECCAC 16121907;
  strain RH040B having the provisional accession number ECCAC 16121908; and
  strain RH015A having the provisional accession number ECCAC 16121903;

Most preferably, the virus of the invention is strain RH018A having the accession number EACC 16121904.

An HSV of the invention is capable of replicating selectively in tumors, such as human tumors. Typically, the HSV replicates efficiently in target tumors but does not replicate efficiently in non-tumor tissue. This HSV may comprise one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5—encoding genes are mutated to confer selective oncolytic activity on the HSV. Mutations of the ICP34.5—encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, in the case of viruses of the invention genes encoding GM-CSF and an immune co-stimulatory pathway activating molecule(s)) gene expression and increases the amount of tumor antigen released as tumor cells die, both of which may also improve the immunogenic properties of the therapy for the treatment of cancer. For example, in a preferred embodiment of the invention, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the invention. Such mutations allow expression of US11 before HSV replication occurs and enhance viral replication in tumors. In particular, such mutations enhance replication of an HSV lacking functional ICP34.5—encoding genes.

Accordingly, in one embodiment the HSV of the invention comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of β-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV IE promoter may be the promoter driving expression of ICP0, ICP4, ICP22, ICP27 or ICP47.

The genes referred to above the functional inactivation of which provides the property of tumor selectivity to the virus may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the invention. Alternatively bacterial artificial chromosome (BAC)-based approaches may be used.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the invention it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5—encoding gene loci.

A virus of the invention is used to express GM-CSF and an immune co-stimulatory pathway activating molecule in tumors. This is typically achieved by inserting a heterologous gene encoding GM-CSF and a heterologous gene encoding the immune co-stimulatory pathway activating molecule in the genome of a selectively replication competent virus wherein each gene is under the control of a promoter sequence. As replication of such a virus will occur selectively in tumor tissue, expression of the GM-CSF and the immune co-stimulatory activating protein by the virus is also enhanced in tumor tissue as compared to non-tumor tissue in the body. Enhanced expression occurs where expression is greater in tumors as compared to other tissues of the body. Proteins expressed by the oncolytic virus would also be expected to be present in oncolytic virus-infected tumor draining lymph nodes, including due to trafficking of expressed protein and of virus in and on antigen presenting cells from the tumor. Accordingly, the invention provides benefits of expression of both GM-CSF and an immune co-stimulatory pathway activating molecule selectively in tumors and tumor draining lymph nodes combined with the anti-tumor effect provided by oncolytic virus replication.

The virus of the invention comprises GM-CSF. The sequence of the gene encoding GM-CSF may be codon optimized so as to increase expression levels of the respective proteins in target cells as compared to if the unaltered sequence is used.

The virus of the invention comprises one or more immune co-stimulatory pathway activating molecules and/or one or more genes encoding an immune co-stimulatory pathway activating molecule Immune co-stimulatory pathway activating molecules include proteins and nucleic acid molecules (e.g. aptamer sequences). Examples of immune co-stimulatory pathway activating molecules include CD40 ligand, GITR ligand, 4-1-BB ligand, OX40 ligand, ICOS ligand, flt3 ligand, TL1A, CD30 ligand, CD70 and single chain antibodies targeting the respective receptors for these molecules (CD40, GITR, 4-1-BB, OX40, ICOS, flt3, DR3, CD30, CD27). The CD40L, GITRL, 4-1-BBL, OX40L, ICOSL, flt3L, TL1A, CD30L or CD70L may be a modified version of any thereof, such as a soluble version.

Activators of immune co-stimulatory pathways include mutant or wild type, soluble, secreted and/or membrane bound ligands, and agonistic antibodies including single chain antibodies. Viruses of the invention preferably encode one or more of CD40L, ICOSL, 4-1-BBL, GITRL or OX40L.

The inhibitor of a co-inhibitory pathway may be a CTLA-4 inhibitor. The CTLA-4 inhibitor is typically a molecule such as a peptide or protein that binds to CTLA-4 and reduces or blocks signaling through CTLA-4, such as by reducing activation by B7. By reducing CTLA-4 signalling, the inhibitor reduces or removes the block of immune stimulatory pathways by CTLA-4.

The CTLA-4 inhibitor is preferably an antibody or an antigen binding fragment thereof. The term "antibody" as referred to herein includes whole antibodies and any antigen binding fragment (i.e., "antigen-binding portion") or single chains thereof. An antibody refers to a glycoprotein comprising at least two heavy (H) chains and two light (kappa) (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (C1q) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')$_2$ fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference. The scFv may be encoded by the nucleotide sequence shown in SEQ ID NO: 34 the nucleotide sequence shown in SEQ ID NO: 35.

Viruses of the invention may encode one or more immune co-stimulatory pathway activating molecules, preferably 1, 2, 3 or 4 immune co-stimulatory pathway activating molecules, more preferably 1 or 2 immune co-stimulatory pathway activating molecules.

For example, the virus may comprise genes encoding:
CD40L and one or more of ICOSL, 4-1-BBL, GITRL, OX40L and a CTLA-4 inhibitor;
ICOSL and one or more of CD40L, 4-1-BBL, GITRL, OX40L and a CTLA-4 inhibitor;
4-1-BBL and one or more of CD40L, ICOSL, GITRL, OX40L and a CTLA-4 inhibitor;
GITRL and one or more of CD40L, ICOSL, 4-1-BBL, OX40L and a CTLA-4 inhibitor;
OX40L and one or more of CD40L, ICOSL, 4-1-BBL, GITRL and a CTLA-4 inhibitor;
a CTLA-4 inhibitor and one or more of CD40L, ICOSL, 4-1-BBL, GITRL and OX40L.

The sequence of the gene encoding the immune co-stimulatory activating molecule may be codon optimized so as to increase expression levels of the respective protein(s) in target cells as compared to if the unaltered sequence is used.

The virus of the invention may comprise one or more further heterologous genes in addition to GM-CSF and an immune co-stimulatory pathway activating molecule, including, in a preferred embodiment, a fusogenic protein such as GALVR-.

The fusogenic protein may be any heterologous protein capable of promoting fusion of a cell infected with the virus of the invention to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R-versions). In a preferred embodiment the fusogenic protein is from GALV and has the R-peptide removed (GALV-R-).

The virus of the invention may optionally comprise multiple copies of the fusogenic protein-encoding gene, preferably 1 or 2 copies. The virus may comprise two or more different fusogenic proteins, including any of the fusogenic proteins listed above.

The fusogenic protein or proteins optionally expressed by a virus of the invention may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

The invention also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV (SEQ ID NO:43), also known as MoMuLV. The heterologous genes may be terminated by poly adenylation sequences. The poly adenylation sequences may be the same or different. Preferably each heterologous gene is terminated by a different poly adenylation sequence, which is preferably selected from the BGH, SV40, HGH and RBG poly adenylation sequences.

The invention also provides a virus, such as a pox virus or a HSV, preferably HSV1, which expresses at least three heterologous genes, wherein each of the three heterologous genes is terminated by a different poly adenylation sequence selected from the BGH, SV40, HGH and RBG poly adenylation sequences. The virus may, for example, express four heterologous genes terminated by each of the BGH, SV40, HGH and RBG poly adenylation sequences, respectively.

Production of Virus

Viruses of the invention are constructed using methods well known in the art. For example plasmids (for smaller viruses and single and multiple genome component RNA viruses) or BACs (for larger DNA viruses including herpes viruses) encoding the viral genome to be packaged, including the genes encoding the fusogenic and immune stimulating molecules under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental virus occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding GM-CSF and the immune co-stimulatory pathway activating molecule. In this case, the parental virus may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

The GM-CSF encoding sequences and immune co-stimulatory pathway activating molecule encoding sequences are inserted into the viral genome under appropriate regulatory control. This may be under the regulatory control of natural promoters of the virus species of the invention used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR, other retroviral LTR promoters, or promoters derived from SV40. Preferably each exogenous gene (e.g. encoding the GM-CSF and immune co-stimulatory pathway activating molecule) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine growth hormone (BGH) poly A sequence, synthetic polyadenylation sequences, the rabbit betaglobin polyadenylation sequence, or viral sequences such as the SV40 early or late polyadenylation sequence).

Pharmaceutical Compositions

The invention provides a pharmaceutical composition comprising the virus and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this invention, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present invention also provides a product of manufacture comprising a virus of the invention in a sterile vial, ampoule or syringe.

Medical Uses/Methods of Treatment

The invention provides the virus of the invention for use in the treatment of the human or animal body by therapy, particularly for use in a method of treating cancer. The cancer is typically in a mammal, preferably in a human. The virus kills infected tumour cells by lysis and by causing infected tumor cells to fuse with one another. The virus of the invention also elicits a systemic anti-tumor immune response, augmented through the expression of GM-CSF and the immune co-stimulatory pathway activating molecule, which also kills cancer cells.

The invention also provides a method of treating cancer, the method comprising administering a therapeutically effective amount of the virus of the invention to an individual in need thereof.

The invention additionally provides the use of the virus of the invention in the manufacture of a medicament for treating cancer.

The virus of the invention is particularly useful in treating any solid tumor including any adenocarcinoma, carcinoma, melanoma or sarcoma. For example, the virus of the invention is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The virus of the invention may be used to treat malignant tumors, including tumors that have metastasised from the site of the original tumor. In this embodiment, the virus may be administered to the primary tumor or to one or more secondary tumors.

The virus of the invention may be administered in combination with other therapeutic agents, including chemotherapy, targeted therapy, immunotherapy (including immune checkpoint blockade, i.e. administration of one or more antagonist of an immune co-inhibitory pathway, and/or one or more agonist of an immune co-stimulatory pathway) and/or in combination with radiotherapy and/or in combination with any combination of these. The therapeutic agent is preferably an anti-cancer agent.

The virus of the invention may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs) or myeloid derived suppressor cells (MDSCs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbaxine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Immunotherapeutic agents may also include bi-specific antibodies, cell based-therapies based on dendritic cells, NK cells or engineered T cells such CAR-T cells or T cells expressing engineered T cell receptors Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the invention may be used: in combination with dacarbazine, a BRAF inhibitor and or CTLA-4, PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyl-tryptophan, Indoximod (1-methyly-D-tryptophan), GDC-0919 or F001287.

The mechanism of action of IDO in suppressing anti-tumor immune responses may also suppress immune responses generated following oncolytic virus therapy. IDO expression is induced by toll like receptor (TLR) activation and interferon-γ both of which may result from oncolytic virus infection. One embodiment of the use of oncolytic virus therapy for cancer treatment includes combination of an oncolytic virus, including a virus expressing GM-CSF and an immune co-stimulatory pathway activating molecule or molecules with an inhibitor of the IDO pathway and optionally one or more antagonist of an immune co-inhibitory pathway and/or one or more agonist of an immune co-stimulatory pathway, including those targeting CTLA-4, PD-1 and/or PD-L1.

The invention also provides a method of treating cancer, which comprises administering a therapeutically effective amount of an oncolytic virus, an inhibitor of the indoleamine 2,3-dioxygenase (IDO) pathway and a further antagonist of an immune co-inhibitory pathway, and/or an agonist of an immune co-stimulatory pathway to a patient in need thereof.

The oncolytic virus is preferably a modified clinical isolate. The oncolytic virus is preferably a pox virus, more preferably a HSV, such as a HSV1 and/or a HSV rendered functionally inactive for ICP34.5 and/or ICP47.

The oncolytic virus may express an immune stimulating molecule, such as GM-CSF and/or a co-stimulatory pathway encoding molecule such as CD40L, GITRL, OX40L, 4-I-BBL or ICO5L, and/or an inhibitor of CTLA-4, and/or a fusogenic protein, such as the GALV fusogenic glycoprotein with the R sequence mutated or deleted.

The further antagonist of an immune co-inhibitory pathway is preferably an antagonist of CTLA-4, an antagonist of PD1 or an antagonist of PD-L1. For example, the further antagonist of an immune co-inhibitory pathway may be an inhibitor of the interaction between PD1 and PD-L1.

Where a therapeutic agent and/or radiotherapy is used in conjunction with a virus of the invention, administration of the virus and the therapeutic agent and/or radiotherapy may be contemporaneous or separated by time. The composition of the invention may be administered before, together with or after the therapeutic agent or radiotherapy. The method of treating cancer may comprise multiple administrations of the virus of the invention and/or of the therapeutic agent and/or radiotherapy. In preferred embodiments, in the case of combination with immune checkpoint blockade or other immune potentiating agents, the virus of the invention is administered once or multiple times prior to the concurrent administration of the immune checkpoint blockade or other immune potentiating agent or agents thereafter, or concurrent with the administration of the immune checkpoint blockade or other immune potentiating agent or agents without prior administration of the virus of the invention.

The virus of the invention may be administered to a subject by any suitable route. Typically, a virus of the invention is administered by direct intra-tumoral injection. Intra-tumoral injection includes direct injection into superficial skin, subcutaneous or nodal tumors, and imaging guided (including CT, MRI or ultrasound) injection into deeper or harder to localize deposits including in visceral organs and elsewhere. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In preferred embodiments, the compositions are administered by intravenous infusion, orally, or directly into a tumor.

The virus and/or therapeutic agent may be administered to a subject in an amount that is compatible with the dosage composition that will be therapeutically effective. The administration of the virus of the invention is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer; an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention (i.e. following recurrence or incomplete removal of tumors following surgery), preferably before any surgical intervention (either for resection of primary or recurrent/metastatic disease), or following recurrence following surgery or following incomplete surgical removal of disease, i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu. In the case of HSV, an initial lower dose (e.g. $10^4$ to $10^7$ pfu) may be given to patients to seroconvert patients who are seronegative for HSV and boost immunity in those who are seropositive, followed by a higher dose then being given thereafter (e.g. $10^6$ to $10^9$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor or into a body cavity. The virus may also be administered by injection into a blood vessel. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention.

EXAMPLE 1

Construction of a Virus of the Invention

The virus species used to exemplify the invention is HSV, specifically HSV1. The strain of HSV1 used for exemplification is identified through the comparison of more than 20 primary clinical isolates of HSV1 for their ability to kill a panel of human tumor-derived cell lines and choosing the virus strain with the greatest ability to kill a broad range of these rapidly, and at low dose. Tumor cell lines used for this comparison include U87MG (glioma), HT29 (colorectal), LNCaP (prostate), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), and/or HT1080 (fibrosarcoma).

Specifically, each primary clinical isolate of HSV is titrated onto each of the cell lines used for screening at MOIs such as 1, 0.1, 0.01 and 0.001 and assessed for the extent of cell death at time points such as 24 and 48 hrs at each dose. The extent of cell killing may be assessed by e.g. microscopic assessment of the proportion of surviving cells at each time point, or e.g. a metabolic assay such as an MTT assay. The exemplary virus of the invention is then constructed by deletion of ICP47 from the viral genome using homologous recombination with a plasmid containing regions flanking HSV1 nucleotides 145300 to 145582 (HSV1 nucleotides 145300 to 145582 being the sequences to be deleted; HSV1 strain 17 sequence Genbank file NC_001806.2) between which are encoded GFP. GFP expressing virus plaques are selected, and GFP then removed by homologous recombination with the empty flanking regions and plaques which do not express GFP are selected. This results in an ICP47 deleted virus in which US11 is expressed as an IE protein as it is now under the control of the ICP47 promoter. ICP34.5 is then deleted using homologous recombination with a plasmid containing regions flanking HSV1 nucleotides 124953 to 125727 (HSV1 nucleotides 124953 to 125727 being the sequences to be deleted; HSV1 strain 17 sequence Genbank file NC_001806.21 between which GFP is encoded. GFP expressing virus plaques are again selected, and GFP then removed by homologous recombination with the same flanking regions but between which are now an expression cassette comprising a codon optimized version of the mouse GM-CSF sequence, a codon optimized version of the GALV R- sequence and codon optimized version of mouse soluble multimeric CD40L driven by a CMV, an RSV and an SV40 promoter. Non-GFP expressing plaques are selected.

The structure of the resulting virus is shown in FIG. 1. The mGM-CSF, CD40L and GALV-R- sequences are shown in SEQ ID NOs 2, 14 and 8 respectively. The structure of the resulting virus is confirmed by restriction digestion and Southern blot, GM-CSF and CD40L expression is confirmed by ELISA, and GALV-R- expression is confirmed by infection of human HT1080 tumor cells and the observation of syncitial plaques.

Viruses are also constructed using similar procedures which only have inserted the gene for GALVR- or mouse GM-CSF and GALV-R-, but without CD40L. The structures of these viruses are also shown in FIG. 1.

For human use, hGM-CSF and hCD40L are used, the sequence for codon optimised versions of which are shown in SEQ ID NO 4 and 13.

EXAMPLE 2

The Effect of the Combined Expression of GM-CSF and an Immune Co-Stimulatory Pathway Activating Molecule from an Oncolytic Virus in Mouse Tumor Models The GALV R- protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells. PiT-1 expression is confirmed by western blotting in untransfected cells and in cells transfected with the PiT-1 expressing lentivirus and by transfection of a plasmid expressing GALV-R- and confirmation that cell fusion occurs.

The utility of the invention is demonstrated by administering CT26/PiT-1 cells into both flanks of Balb/c mice and allowing the CT26/PiT-1 tumors to grow to approximately 0.5 cm in diameter.

The following treatments are then administered to groups of mice (five per group), into one flank of each mouse only 3 times per week for two weeks:
  50 µl of saline (1 group);
  50 µl of $10^5$ pfu/ml, $10^6$ pfu/ml, or $10^7$ pfu/ml of the HSV with only GALVR- inserted (3 groups);
  50 µl of $10^5$ pfu/ml, $10^6$ pfu/ml, or $10^7$ pfu/ml of the HSV with only GALVR- and mouse GM-CSF inserted (3 groups);
  50 µl of $10^5$ pfu/ml, $10^6$ pfu/ml, or $10^7$ pfu/ml of the virus with GALVR- and both mouse GM-CSF and CD40L inserted (3 groups).

Effects on tumor growth are then observed for up to one month. Superior tumor control and shrinkage in both injected and uninjected tumors with the virus expressing GM-CST and CD40L as compared to the other groups is observed, including through an improved dose response curve.

EXAMPLE 3

The Effect of Combined Expression of GM-CSF and an Immune Co-Stimulatory Pathway Activating Molecule from an Oncolytic Virus on the Therapeutic Effect of Immune Checkpoint Blockade in Mouse Tumor Models The experiment in Example 2 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline, (2) HSV with GALVR- inserted as in Example 2, (3) HSV with GM-CSF and GALV-R- inserted as in Example 2, (4) HSV with GM-CSF, CD40L and GALV-R- inserted as in Example 2, (5) PD-1 antibody, (6) CTLA-4 antibody, (7) HSV with GALV-R- inserted plus PD-1 antibody, (8) HSV with GALV-R- inserted gene plus CTLA-4 antibody, (9) HSV with GM-CSF and GALV-R- and PD-1 antibody or (10) HSV with GM-CSF and GALV-R- and CTLA-4 antibody (11) HSV with GM-CSF, CD40L and GALV-R- and PD-1 antibody or (12) HSV with GM-CSF, CD40L and GALV-R- and CTLA-4 antibody. Superior tumor control and shrinkage in both injected and uninjected tumors with the virus expressing GM-CSF and CD40L together with the anti-PD-1 antibody or the anti-CTLA-4 antibody as compared to the other groups is observed, including through an improved dose response curve.

EXAMPLE 4

Collection of Clinical Isolates

The virus species used to exemplify the invention is HSV, specifically HSV1. To exemplify the invention, 181 volunteers were recruited who suffered from recurrent cold sores. These volunteers were given sample collection kits (including Sigma Virovult collection tubes), and used these to swab cold sores when they appeared following which these samples were shipped to Replimune, Oxford UK. From June 2015-February 2016, swabs were received from 72 volunteers. A sample of each swab was used to infect BHK cells. Of these 36 live virus samples were recovered following plating out and growth on PHK cells. These samples are detailed in Table 1.

TABLE 1

Details of Tested Swab Samples & Result

| Sample Number | Virus retrieved |
|---|---|
| RH001A | No |
| RH001B | |
| RH002A | Yes |
| RH003A | No |
| RH004A | Yes |
| RH004B | |
| RH005A | No |
| RH005B | |
| RH006A | No |
| RH006B | |
| RH007A | Yes |
| RH007B | |
| RH007C | |
| RH008A | No |
| RH008B | |
| RH008C | |
| RH009A | No |
| RH009B | |
| RH010A | No |
| RH011A | No |
| RH011B | |
| RH011C | |
| RH012A | No |
| RH013A | No |
| RH014A | Yes |
| RH014B | |
| RH015A | Yes |
| RH016A | No |
| RH016B | |
| RH017A | Yes |
| RH018A | Yes |
| RH018B | |
| RH018C | |
| RH019A | No |
| RH019B | |
| RH019C | |
| RH020A | Yes- RH020A only |
| RH020B | |
| RH020C | |
| RH021A | Yes |
| RH021B | |
| RH022A | Yes |
| RH022B | |
| RH023A | Yes |
| RH024A | No |
| RH025A | Yes -RH025B only |
| RH025B | |
| RH026A | Yes |
| RH027A | No |
| RH027B | |
| RH027C | |
| RH028A | No |
| RH028B | |
| RH028C | |
| RH029A | No |

TABLE 1-continued

Details of Tested Swab Samples & Result

| Sample Number | Virus retrieved |
|---|---|
| RH030A | No |
| RH031A | Yes - RH031A to RH031D |
| RH031B | |
| RH031C | |
| RH031D | |
| RH031E | |
| RH031F | |
| RH032A | No |
| RH033A | No |
| RH033B | |
| RH033C | |
| RH034A | No |
| RH034B | |
| RH034C | |
| RH035A | No |
| RH036A | Yes |
| RH037A | Yes |
| RH038A | Yes |
| RH039A | No |
| RH039B | |
| RH039C | |
| RH040A | Yes |
| RH040B | |
| RH040C | |
| RH041A | Yes |
| RH042A | Yes |
| RH043A | No |
| RH043B | |
| RH043C | |
| RH044A | No |
| RH045A | No |
| RH046A | Yes |
| RH047A | Yes- RH047A and RH047C |
| RH047B | |
| RH047C | |
| RH048A | No |
| RH049A | No |
| RH049B | |
| RH049C | |
| RH050A | No |
| RH051A | Yes |
| RH051B | |
| RH052A | Yes - RH052A only |
| RH052B | |
| RH053A | No |
| RH054A | No |
| RH055A | No |
| RH055B | |
| RH056A | Yes |
| RH057A | No |
| RH058A | Yes |
| RH058B | |
| RH059A | No |
| RH060A | No |
| RH061A | Yes |
| RH062A | No |
| RH063A | No |
| RH064A | Yes |
| RH065A | Yes |
| RH065B | |
| RH066A | No |
| RH067A | No |
| RH067B | |
| RH068A | No - contaminated |
| RH069A | No |
| RH069A | |
| RH070A | Yes |
| RH071A | Yes |
| RH072A | No |
| RH073A | Yes |
| RH073B | |
| RH074A | No |
| RH074B | |
| RH075A | No |
| RH076A | No |
| RH078A | No |
| RH078B | |
| RH079B | Yes |
| RH079B | |
| RH080A | No |
| RH081A | Yes |
| RH082A | No |
| RH082B | |
| RH083A | Yes |
| RH083B | |
| RH084A | Yes |
| RH084B | |
| RH084C | |
| RH085A | No |
| RH086A | No |
| RH087A | Yes - RH078B only |
| RH087B | |

Designations A, B, C etc. indicate multiple swabs from the same volunteer.

EXAMPLE 5

Identification of Clinical Isolates with Improved Anti-Tumor Effects

The abilities of the primary clinical isolates of HSV1 to kill a panel of human tumor-derived cell lines was tested. The tumor cell lines used for this comparison were HT29 (colorectal), MDA-MB-231 (breast), SK-MEL-28 (melanoma), Fadu (squamous cell carcinoma), MCF7 (breast), A549 (lung), MIAPACA-2 (pancreas) and HT1080 (fibrosarcoma). The cell lines were used to test for the level of CPE achieved at a range of MOI and times post infection for each of the primary clinical isolates.

Experiments were conducted in parallel using 5 to 8 of the new viruses strains at the same time. The virus strains were plated out in duplicate at a range of MOIs (0.001-1), and the extent of CPE following crystal violet staining was assessed at 24 and 48 hours following infection. The viral strains which were most effective at killing the tumor cell lines were scored, and the most effective two or three strains from each screen of 5-8 strains were identified and compared in parallel in a further experiment to identify the top strains for further development.

The initial screens demonstrated substantial variability in the ability of the different strains to kill the different tumor cell lines. Of an initial 29 strains tested, 8 strains of interest were identified in the initial screens for further comparison. These were strains RH004A, RH015A, RH018A, RH021A, RH023A, RH31A, RH040A, and RH047A.

Figure 2:
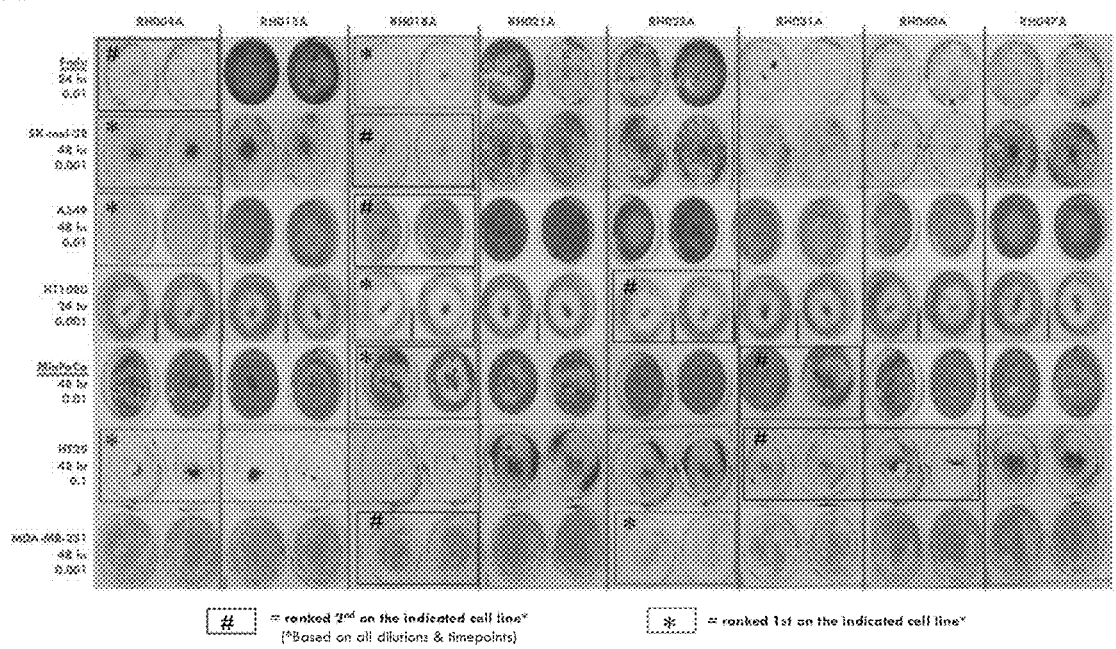
FIG. 2 shows the differential abilities of the eight top ranking HSV1 clinical isolate strains as assessed by crystal violet staining 24 hours or 48 hours after infection with a MOI of 0.1, 0.01 or 0.001 as indicated in the Figure to kill Fadu, SK-mel-28, A549, HT1080, MIA-PA-CA-2, HT29 and MDA-MB-231 human tumor cell lines. The virus strains ranked first and second on each cell line are indicated. The virus RH018A was ranked first on each of the Fadu, HT1080, MIA-PA-CA-2 and HT29 cell lines and second on each of the SK-mel-28, A549 and MDA-MB-231 cell lines. RH004A was ranked joint first with RH018A and RH015A on the HT29 cell line, first on the SK-mel-28 and A549 cell lines and second on the Fadu cell line. RH023A was ranked first on the MDA-MB-231 cell line and second on the HT1080 cell line. RH031A was ranked second on each of the MIA-PA-CA-2 and HT29 cell lines. RH040A was ranked joint second on the HT29 cell line.

The 8 strains for further comparison were tested in parallel on the panel of tumor cell lines, and their relative ability to kill these tumor cell lines was assessed following crystal violet staining and observation for CPE. FIG. 2 shows a representative time point and MOI for these viruses on each of the viruses on each of the cell lines demonstrating the differential ability of the viruses to kill the target tumor cell lines observed.

There was substantial variation amongst the strains, and it was found that while a particular strain may be particularly effective at killing one cell line, it is not necessarily particularly effective at killing other cell lines too, further demonstrating the degree of variability in the ability of clinical strains of HSV to kill tumor cells of different types.

Figure 3:
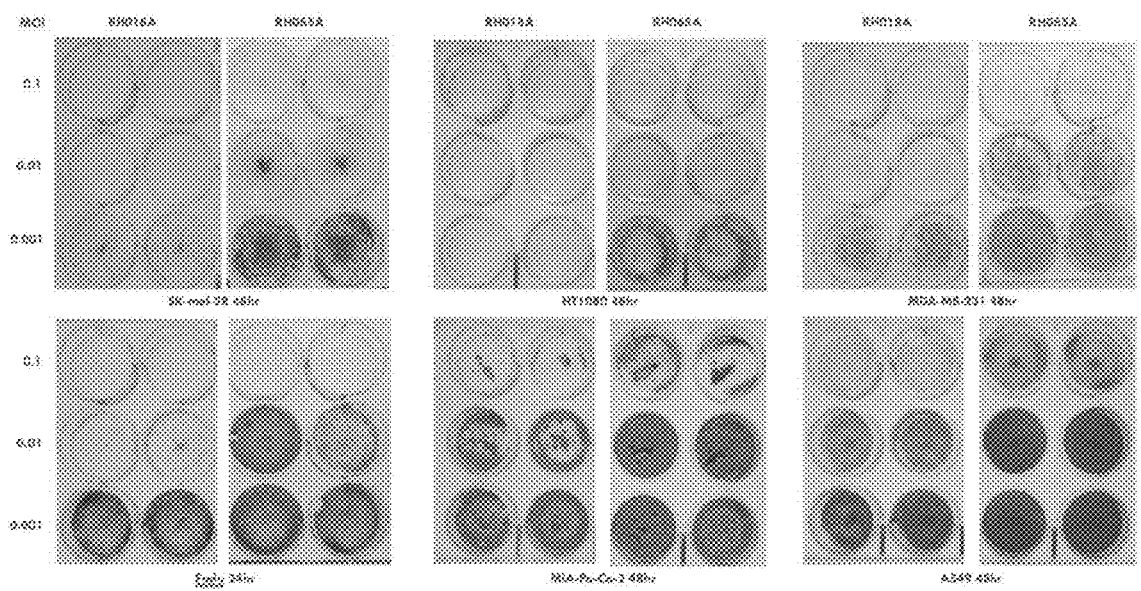
FIG. 3 shows a comparison between strain RH018A, the strain ranked first of all the strains tested, with an 'average' strain from the screen (i.e. strain RH065A). Approximately 10 fold less of strain RH018A was needed to kill an equal proportion of cells than was needed of strain RH065A as shown by crystal violet staining 24 or 48 hours post infection with MOIs of 0.1, 0.01 and 0.001 in SK-mel-28, HT1080, MDA-MB-231, Fadu, MIA-PA-CA-2 and A549 cell lines.
Figure 4A:
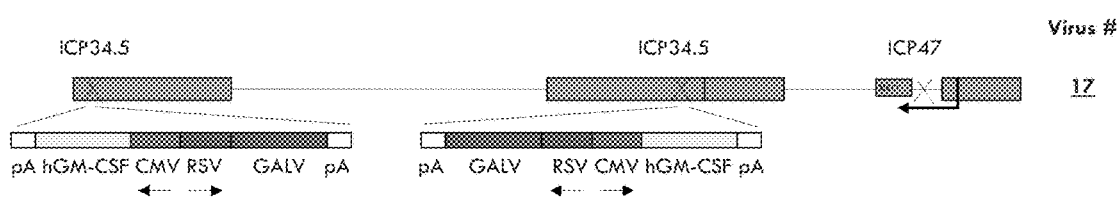
FIGS. 4 and 5 depict structures of HSV1 viruses modified by the deletion of ICP34.5 and ICP47 such that the US11 gene is under control of the ICP457 immediate early promoter and containing heterologous genes in the ICP34.5 locus. The viruses were constructed using the RH018A strain unless otherwise stated in the Figure.
Figure 4B:
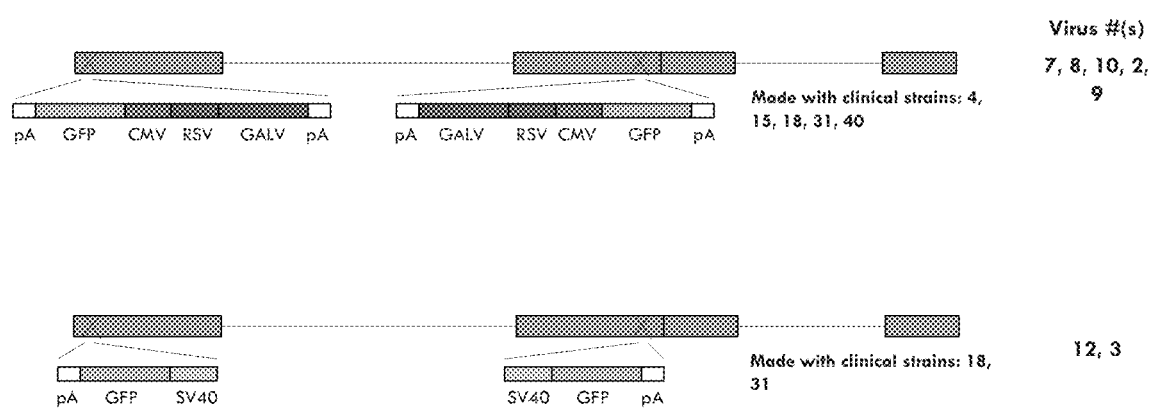
Figure 4C:
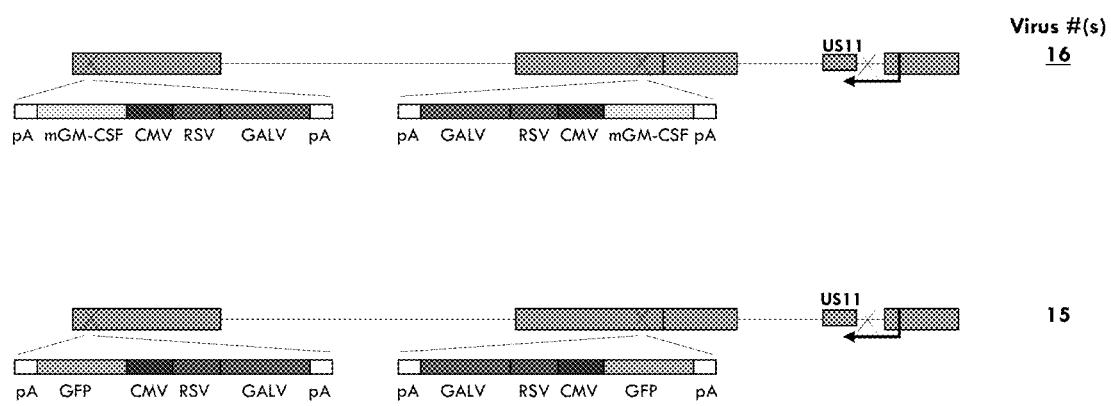
Figure 4D:
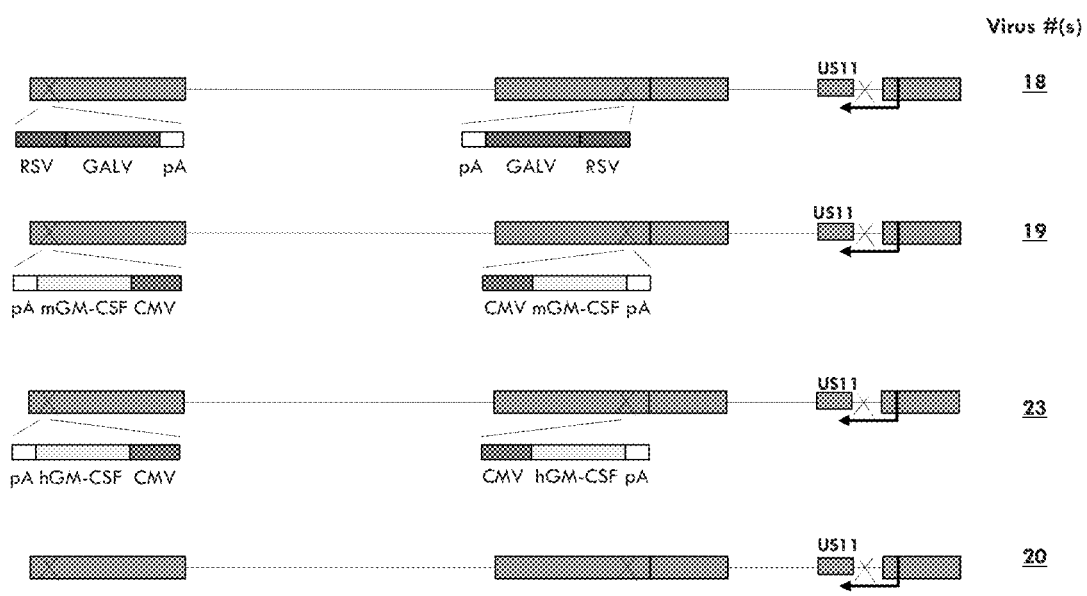
Figure 4E:
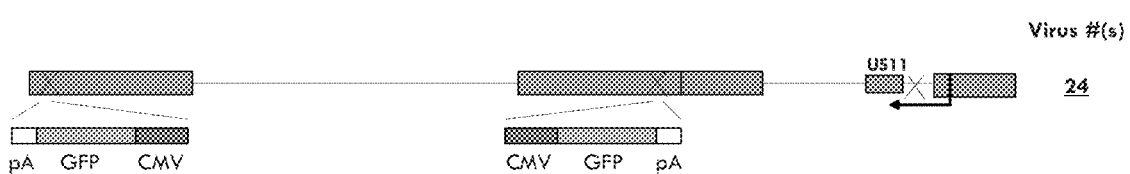
Figure 4F:
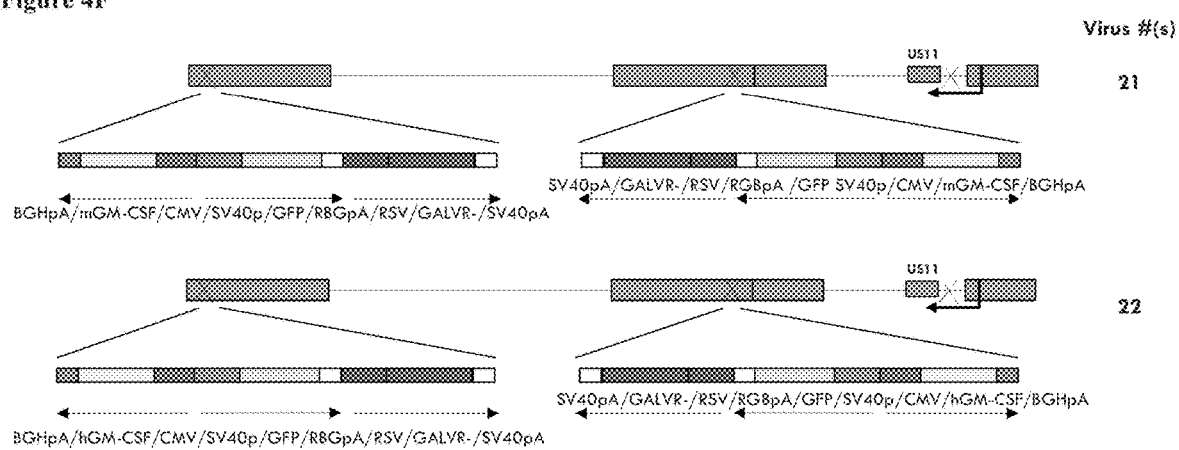
Figure 5A:
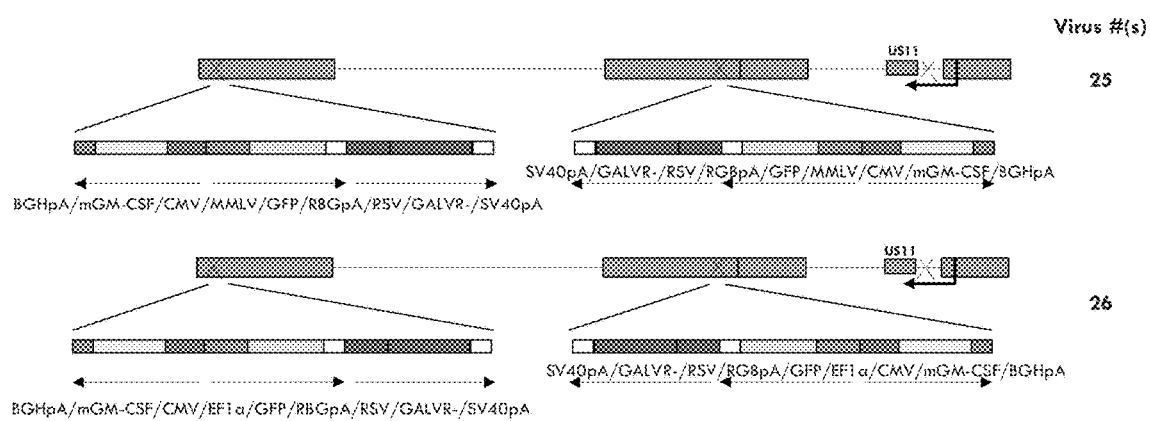
Figure 5B:
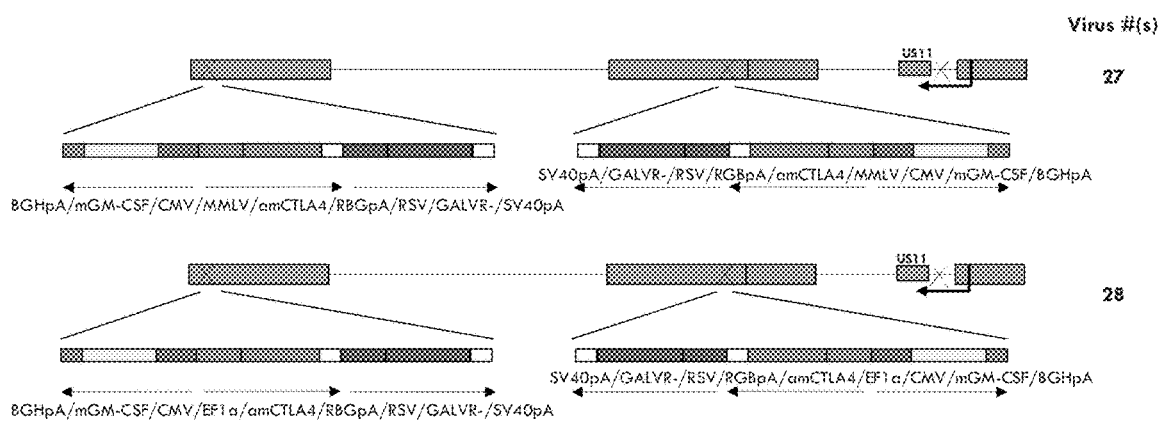
Figure 5C:
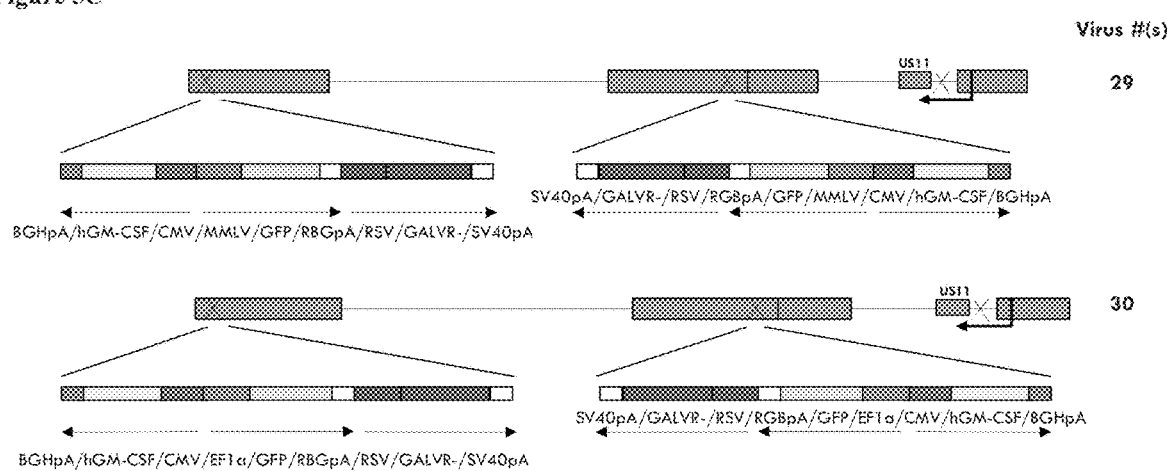
Figure 5D:
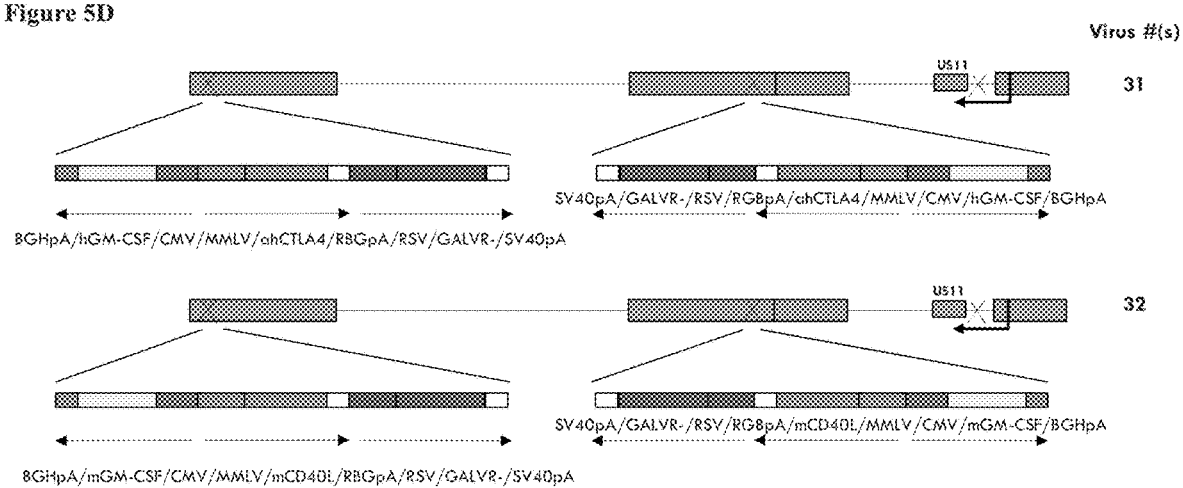
Figure 5E:
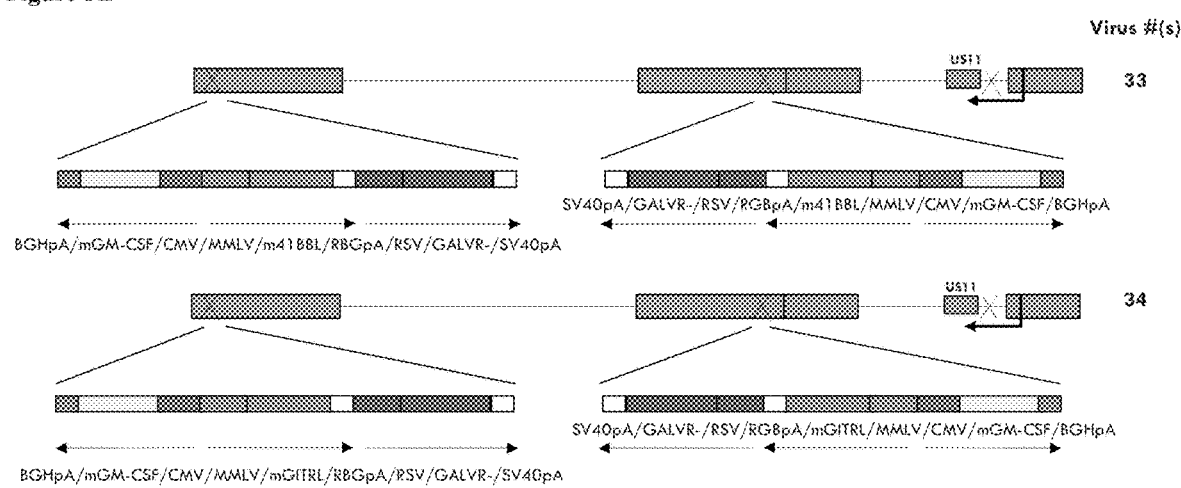
Figure 5F:
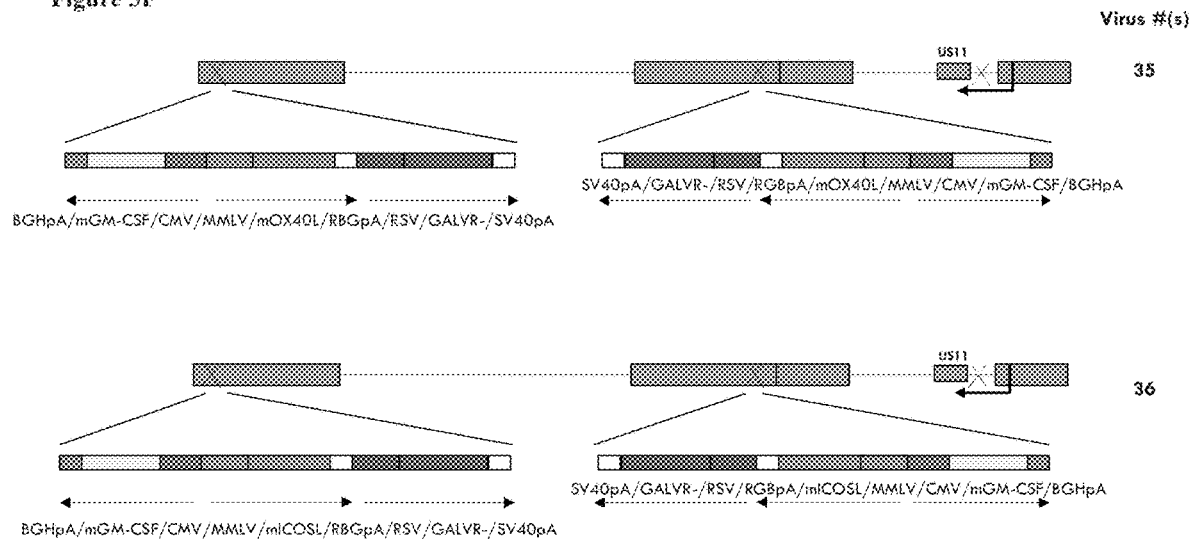

FIG. 3 also indicates which of the virus strains was both best and second best at killing each of the cell lines, enabling the virus strains to be rank ordered as to their overall relative ability to kill the panel of cell lines as a whole. This analysis demonstrated that strains RH004A, RH015A, RH018A, RH031A and RH040A were relatively more effective than the other strains, and these five strains were chosen for potential further development as oncolytic agents. Of these top five strains, the relative rank order based on their abilities to kill across the panel of cell lines was RH018A>RH004A>RH031A>RH040A>RH015A.

More specifically, in these experiments, the tumor cell lines were used to seed multi-well tissue culture plates so that they were about 80% confluent on the day of infection. Representative wells from each tumor cell line were trypsinised and the number of cells in the well determined. These cell counts are used to determine the volume of each clinical isolate required to give an MOI of 1, 0.1, 0.01 and 0.001. Separate wells of a tumor cell line were infected with the clinical isolate at these MOI. All infections are carried out in quadruplicate. Duplicate wells were incubated for 24 hours and duplicate wells were incubated for 48 hours, both at 37° C., 5% $CO_2$, prior to fixation of the cells with glutaraldehyde and staining with crystal violet. The level of cell lysis was then assessed by gross observation, microscopy (cell counts) and photography.

Strain RH018A, the strain ranked first of all the strains tested was compared to an 'average' strain from the screen (i.e. a strain which was not in the top 8, but was also not in the group of strains which were least effective and killing the panel of tumor cell lines). This comparison showed that Strain RH018A was approximately 10 fold more effective than this average strain (Strain RH065A) at killing the tumor cell lines (i.e. approximately 10 fold less of Strain RH018A was needed to kill an equal proportion of cells than was needed of Strain RH065A). This is shown in FIG. 3.

EXAMPLE 6

Modification of Clinical Isolates

In this Example the clinical isolates selected in Example 5 were modified by deletion of ICP34.5 from the viral genome using homologous recombination with a plasmid containing regions flanking the ICP34.5 encoding gene (nucleotides 143680-145300 and 145,582-147,083; HSV1 strain 17 sequence Genbank file NC_001806.2) between which are encoded GFP and the GALV-R-fusogenic glycoprotein. The structure of this virus, (Virus 10) is shown in FIG. 4.

Additional viruses based on Strain RH018A were also constructed in which both ICP34.5 and ICP47 (using flanking regions containing nucleotides 123464-124953 and 125727-126781; HSV1 strain 17 sequence Genbank file NC_001806.2) were deleted (resulting in placement of US11 under the control of the ICP47 promoter). To construct these viruses, GFP expressing virus plaques, with GFP expressed in place of ICP47 were first selected. GFP was then removed by homologous recombination with the empty flanking regions, and plaques not expressing GFP were selected. This resulted in an ICP47 deleted virus in which US11 is expressed as an IE protein as it is now under the control of the ICP47 promoter. ICP34.5 was then deleted using homologous recombination with a plasmid containing regions flanking HSV1 nucleotides 143680-145300 and 145,582-147,083; HSV1 strain 17 sequence Genbank file NC_001806.2) between which GFP is encoded. GFP expressing virus plaques were again selected, and GFP then removed by homologous recombination with the same flanking regions but between which are now an expression cassette comprising the genes to be inserted. The viruses that were constructed are shown in FIGS. 1, 4 and 5. These included a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction was performed using methods which are standard in the art.

The mGM-CSF and GALV-R- sequences are shown in SEQ ID NOs 2 and 8 respectively. The structure of the resulting virus was confirmed by PCR, GM-CSF expression was confirmed by ELISA, and GALV-R- expression was confirmed by infection of human HT1080 tumor cells and the observation of syncitial plaques.

Figure 6:
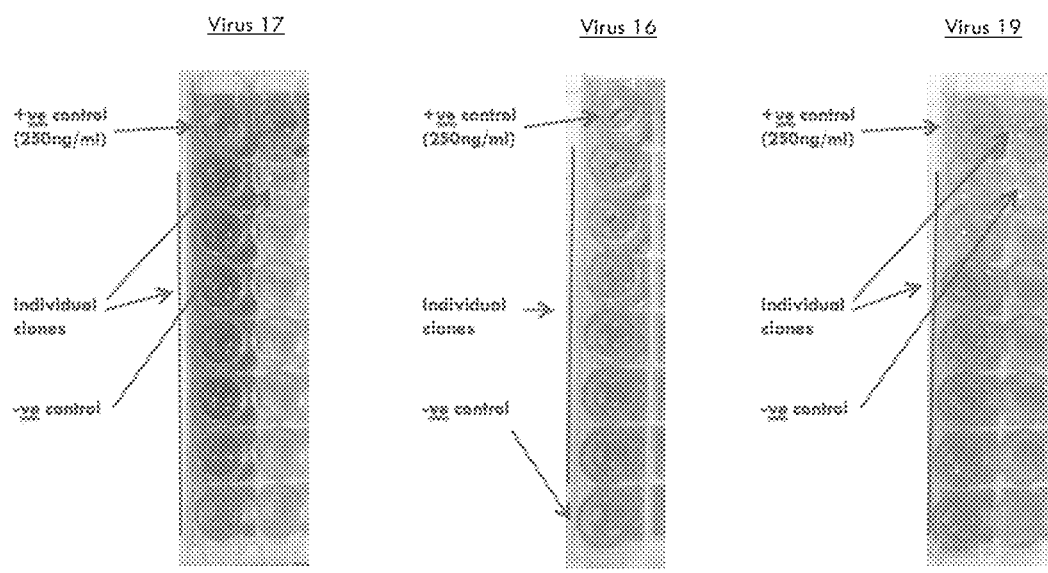
FIG. 6 shows the results of an ELISA to detect expression of human or mouse GM-CSF in supernatants from BHK cells infected with virus 16 (mGM-CSF and GALVR-), virus 17 (hGM-CSF and GALVR-) and virus 19 (mGM-CSF).

For human use, hGM-CSF is used, the sequence for a codon optimised version of which is shown in SEQ ID NO 4. The structure of this virus is shown in FIG. 4. Expression of mouse or human GM-CSF from viruses 16, 17 and 19 is shown in FIG. 6.

EXAMPLE 7

Figure 7A:
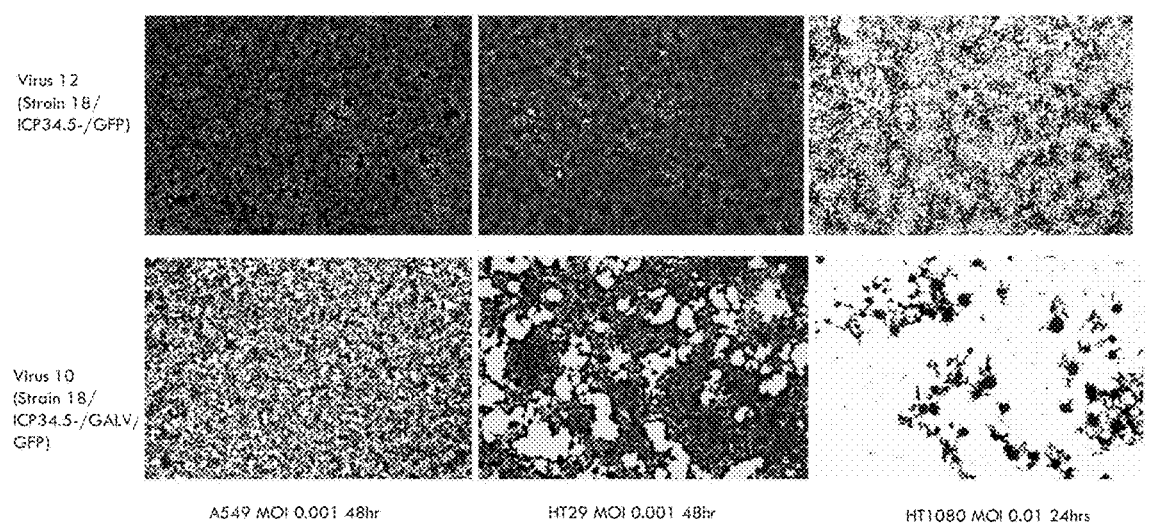
FIG. 7 is a comparison between the cell-killing abilities of strain RH018A in which ICP34.5 is deleted and which expresses GALVR- and GFP (virus 10) with a virus that expresses only GFP (virus 12) as determined by crystal violet staining in three cell lines at low magnification.
Figure 7B:
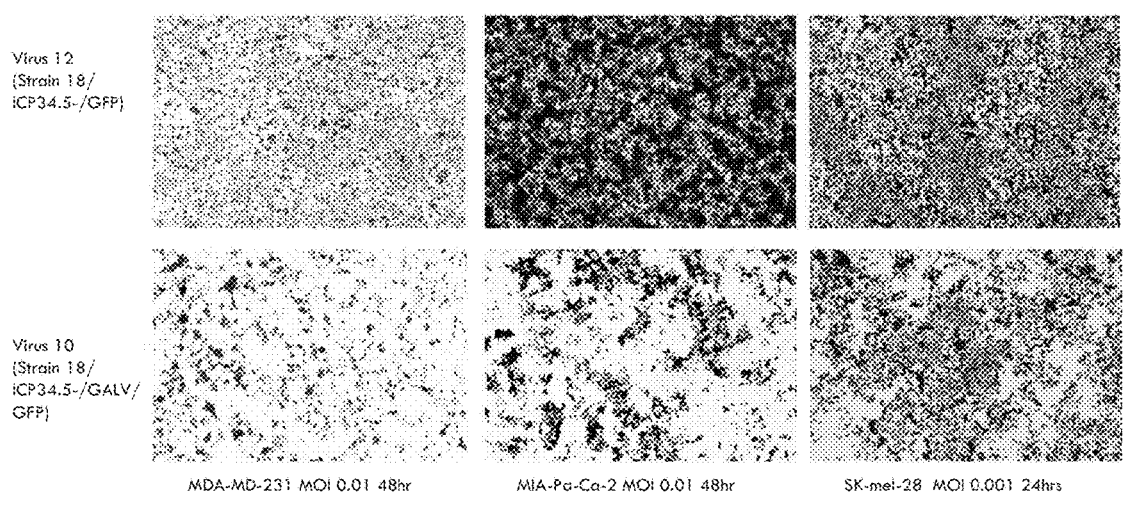

A Virus of the Invention Modified for Oncolytic Use and Expressing a Fusogenic Glycoprotein Shows Enhanced Tumor Cell Killing In Vitro as Compared to a Virus which Does Not Express a Fusogenic Glycoprotein Virus 10 (see FIG. 4), based on clinical Strain RH018A in which ICP34.5 is deleted and which expresses GALVR- and GFP, was compared in vitro to a virus which expresses only GFP (Virus 12). Virus 10 showed enhanced killing on a panel of human tumor cell lines as compared to Virus 12, as shown in FIG. 7.

EXAMPLE 8

Figure 8A:
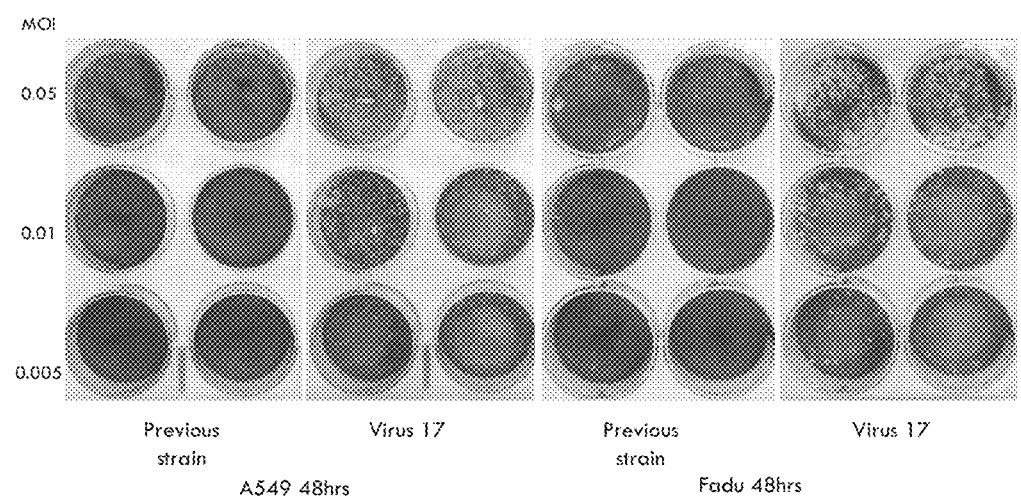
FIG. 8 is a comparison between the cell-killing abilities of strain RH018A in which ICP34.5 and ICP47 are deleted and which expresses GALVR- and GM-CSF (virus 17) with a prior art strain with the same modifications as determined by crystal violet staining in four cell lines.
Figure 8B:
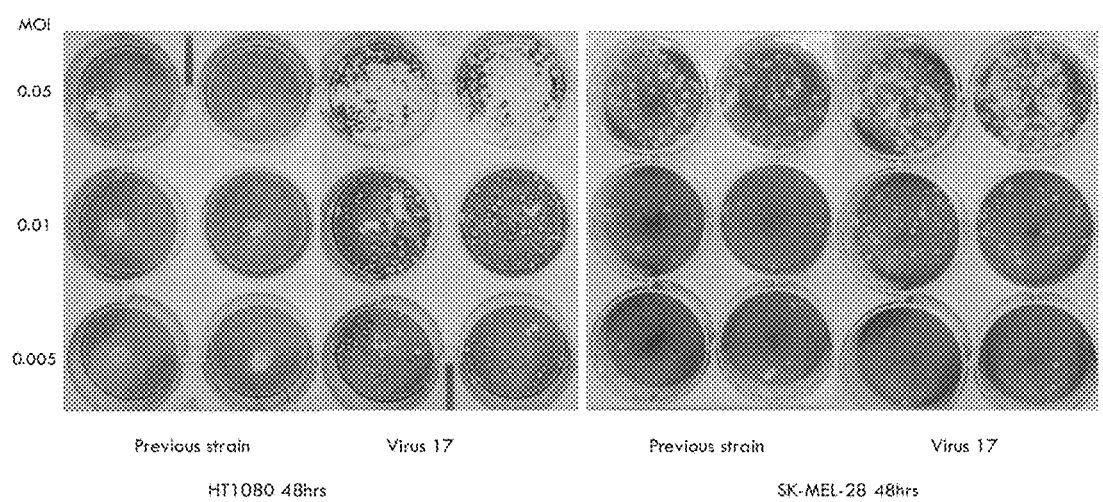

A Virus of the Invention Modified for Oncolytic Use Shows Enhanced Tumor Cell Killing as Compared to a Similarly Modified Virus which is Not of the Invention Virus 17 (see FIG. 4), based on clinical Strain RH018A in which ICP34.5 and ICP47 are deleted and which expresses GALVR- and GM-CSF, was compared in vitro to a known virus which was also deleted for ICP34.5 and ICP47 but which was not derived from a strain of the invention and which expresses only GM-CSF. Virus 17 showed enhanced killing on a panel of human tumor cell lines as compared to the previous virus, as shown in FIG. 8.

EXAMPLE 9

Figure 9:
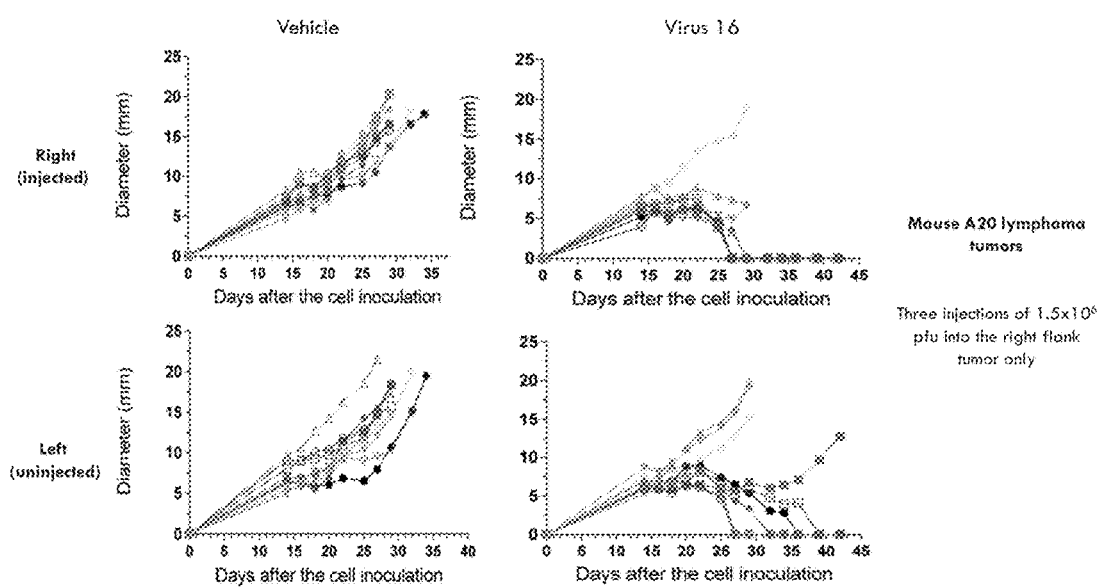
FIG. 9 shows the effectiveness of Virus 16 (ICP34.5 and ICP47 deleted expressing GALVR- and mGM-CSF) in treating mice harbouring A20 lymphoma tumors in both flanks. Tumors on the right flanks were injected with the virus or vehicle and the effects on tumor size was observed for 30 days. The virus was effective against both injected tumors and non-injected tumors.

A Virus of the Invention Modified for Oncolytic Use Effectively Treats Mouse Tumors In Vivo Virus 16 was tested in mice harboring A20 lymphoma tumors in the left and right flanks. One million tumor cells were first implanted in both flanks of Balb/c mice and tumors allowed to grow to 0.5-0.7 cm in diameter. Tumors on the right flank were then injected 3 times (every other day) with either vehicle (10 mice) or 5×10exp6 pfu of Virus 16 (10 mice), and effects on tumor size observed for a further 30 days. This demonstrated that both injected and uninjected tumors were effectively treated with Virus 16 (see FIG. 9).

EXAMPLE 10

The Effect of the Combined Expression of a Fusogenic Protein and an Immune Stimulatory Molecule from an Oncolytic Virus of the Invention in a Rat Tumor Model The GALV R- protein causes cell to cell fusion in human cells but not in mouse cells. However, GALV R- does cause fusion in rat cells.

The utility of the invention was further demonstrated by administering 9 L cells into the flanks of Fischer 344 rats and allowing the 9 L tumors to grow to approximately 0.5 cm in diameter.

The following treatments were then administered to groups of rats (ten per group), into one flank only of each rat three times per week for three weeks:
 50 µl of vehicle;
 50 µl of $10^7$ pfu/ml of Virus 19 (expresses mGM-CSF but not GALV R-);
 50 µl of $10^7$ pfu/ml of Virus 16 (expresses both mouse GM-CSF and GALV-R-).

Figure 10:
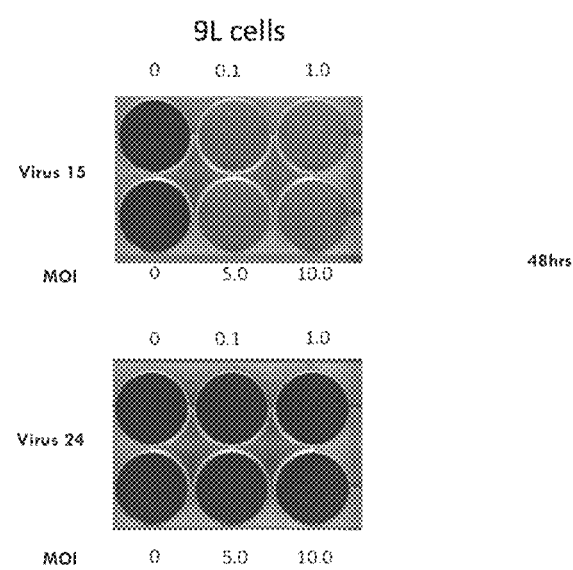
FIG. 10 demonstrates the effects of Virus 15 (ICP34.5 and ICP47 deleted expressing GALVR- and GFP) and Virus 24 (ICP34.5 and ICP47 deleted expressing GFP) on rat 9 L cells in vitro as assessed by crystal violet staining. The virus expressing GALV (Virus 15) showed enhanced killing of rat 9 L cells in vitro as compared to a virus which does not express GALV (Virus 24).
Figure 15:
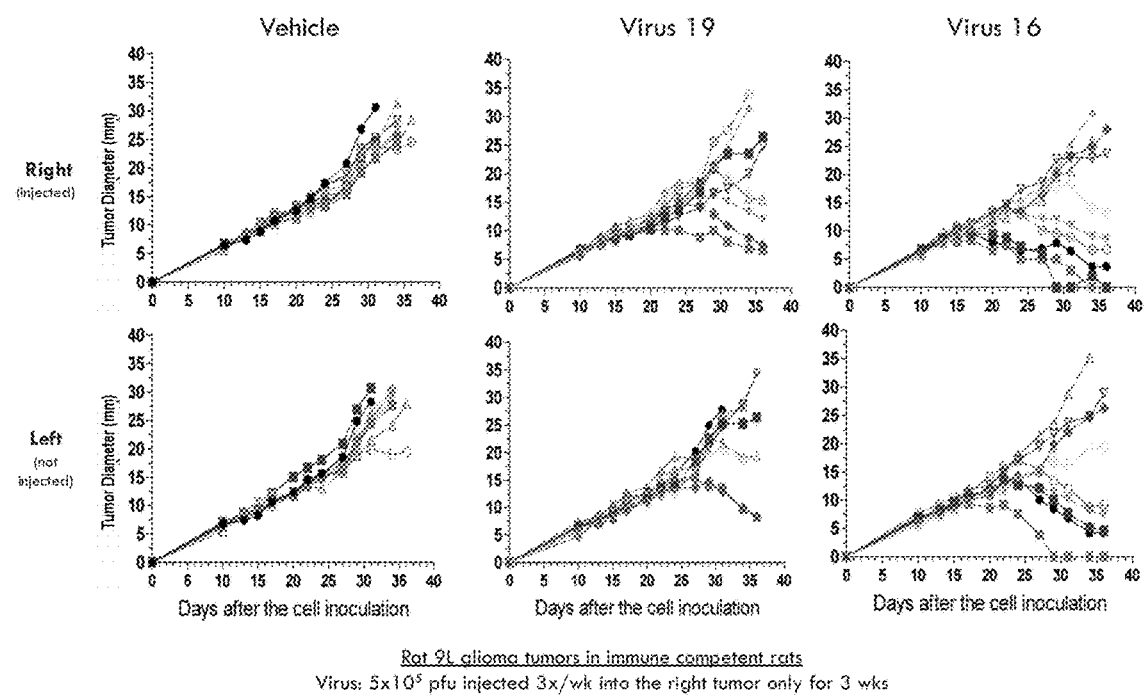
FIG. 15 demonstrates the effects of viruses of the invention expressing GALVR- on 9 L cells in the flanks of Fischer 344 rats. The following treatments were administered to groups of rats (ten per group), into one flank of each rat only three times per week for three weeks: 50 µl of vehicle; 50 µl of 10$^7$ pfu/ml of Virus 19 (expresses mGM-CSF but not GALV R-); or 50 µl of 10$^7$ pfu/ml of Virus 16 (expresses both mouse GM-CSF and GALV-R-). Effects on tumor growth were then observed for a further 30 days. Superior tumor control and shrinkage was observed with the virus expressing GM-CSF and GALV-R- as compared to the virus expressing GM-CSF alone.

Effects on tumor growth were then observed for a further ≈30 days. This demonstrated superior tumor control and shrinkage with the virus expressing GALV-R- in both injected and uninjected tumors, demonstrating improved systemic effects. This is shown in FIG. 15. FIG. 10 shows that a virus expressing GALV (Virus 15) also shows enhanced killing of rat 91 cells in vitro as compared to a virus which does not express GALV (Virus 24).

EXAMPLE 11

A Virus of the Invention Modified for Oncolytic Use is Synergistic with Immune Checkpoint Blockade in Mouse Tumor Models Virus 16 was tested in mice harboring CT26 tumors in the left and right flanks. One million tumor cells were first implanted in both flanks of Balb/c mice and tumors allowed to grow to 0.5-0.6 cm in diameter.

Figure 11A:
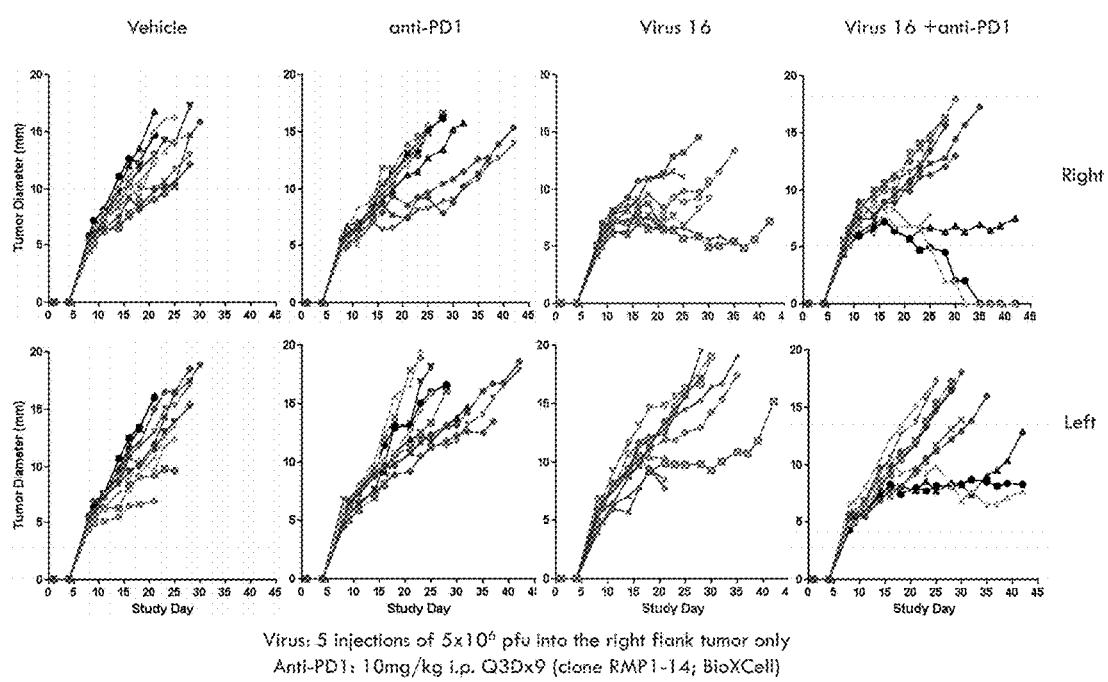
FIG. 11A shows that using Virus 16 and anti-PD1 in combination has a better anti-tumor effect than using either anti-PD1 or the virus alone.
Figure 11B:
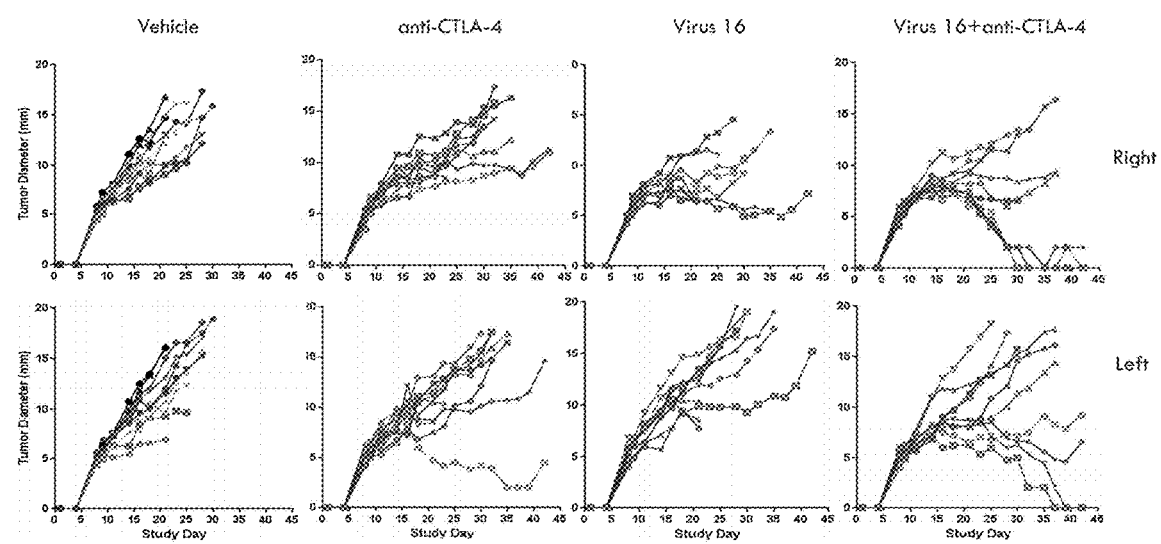
FIG. 11B shows that the anti-tumor effect of Virus 16 in combination with anti-CTLA-4 was better than the anti-tumor effect of either Virus 16 or anti-CTLA-4 alone.
Figure 12A:
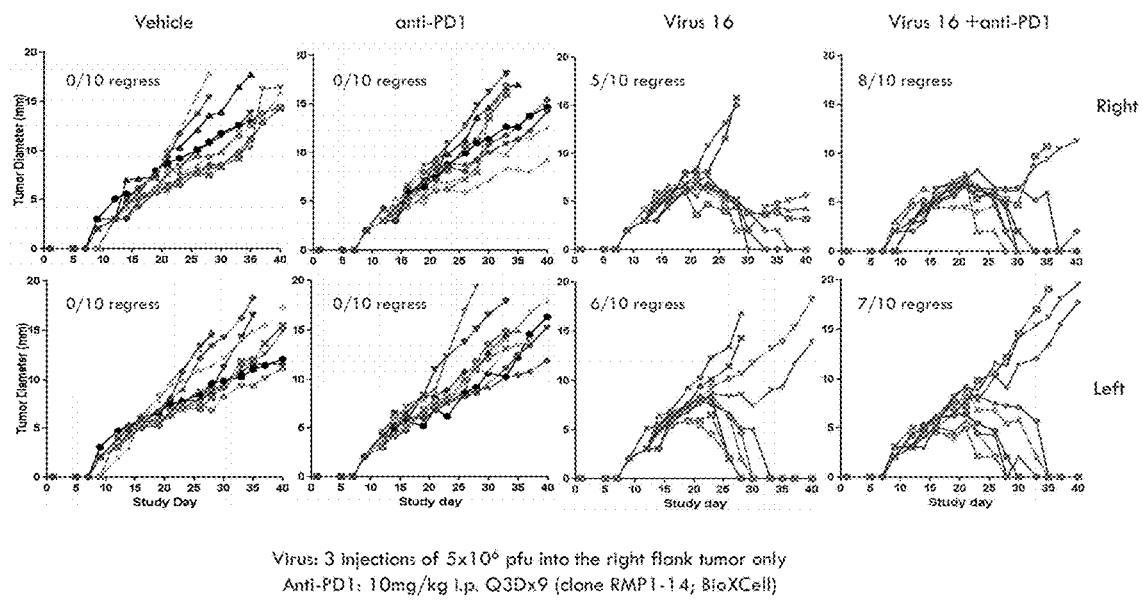
FIG. 12 shows the enhanced anti-tumor activity of Virus 16 in combination with immune checkpoint blockade in mouse A20 tumors in both flanks of Balb/c mice as compared to either virus alone or checkpoint blockade alone (anti-PD1).
Figure 12B:
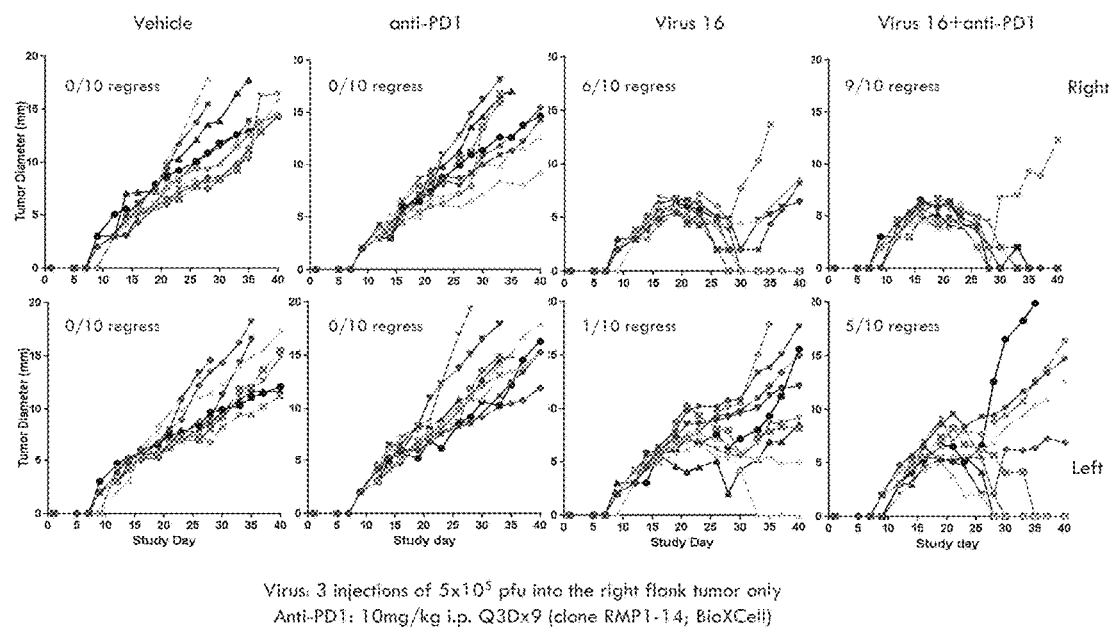
Figure 12C:
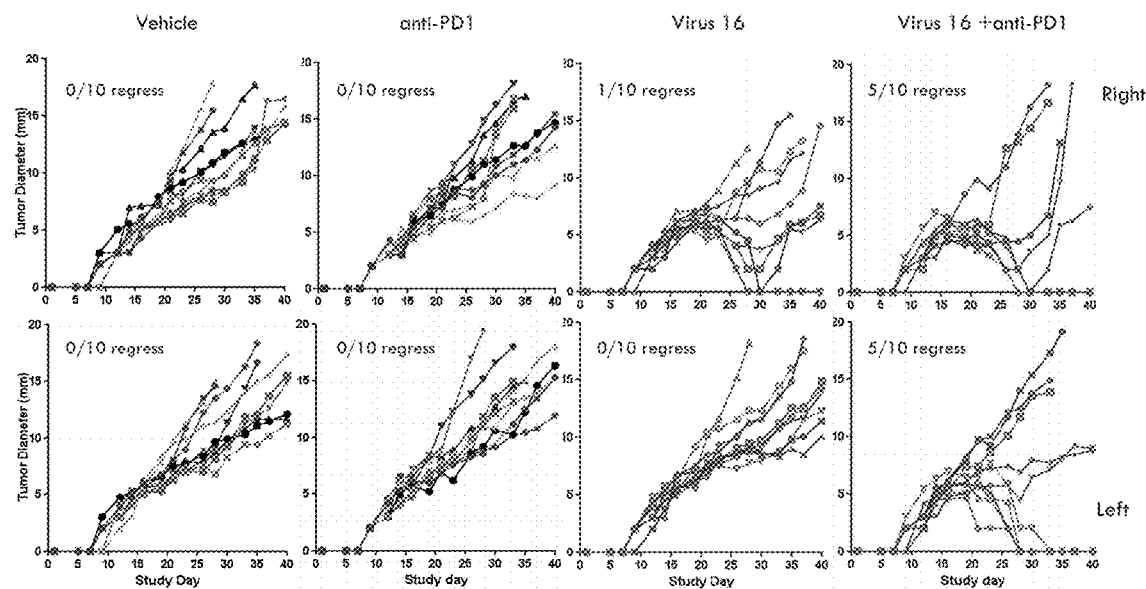
Figure 12D:
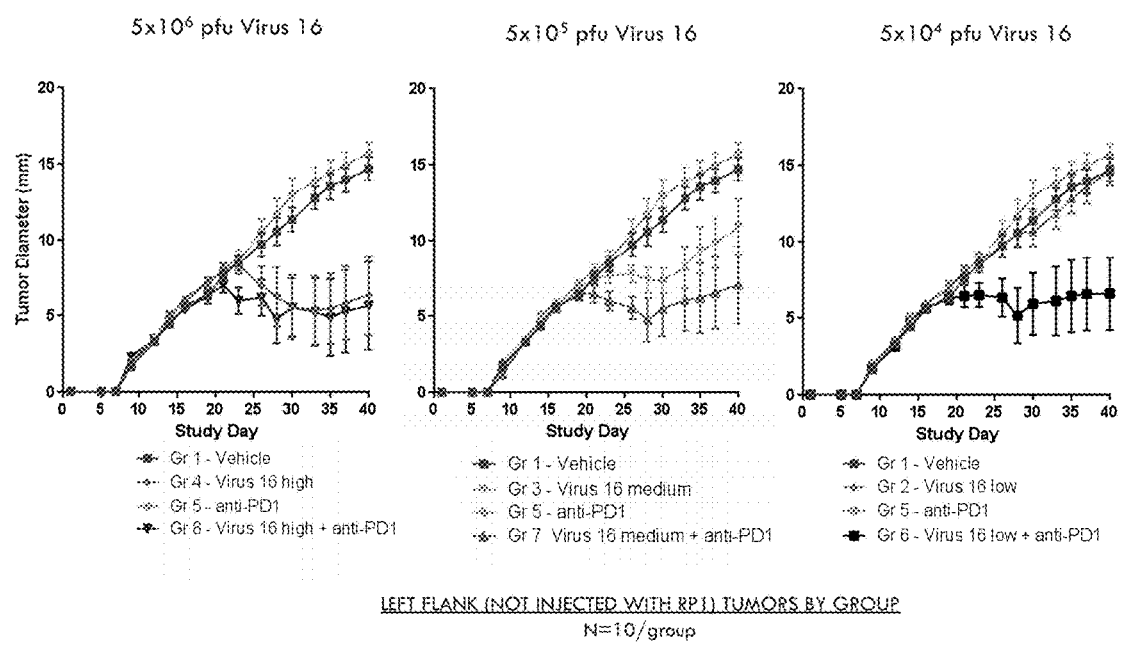

Groups of 10 mice were then treated with:
 Vehicle (3 injections into right flank tumors every other day);
 5×10exp6 pfu of Virus 16 injected in the right flank tumor every other day;
 anti-mouse PD1 alone (10 mg/kg i.p. every three days, BioXCell clone RMP1-14);
 anti-mouse CTLA-4 (3 mg/Kg i.p every three days, BioXCell clone 9D9);
 anti-mouse PD1 together with Virus 16;
 anti-mouse CTLA4 together with Virus 16;
 1-methyl trypotophan (IDO inhibitor (5 mg/ml in drinking water));
 anti-mouse PD1 together with 1-methyl trypotophan;
 anti-mouse PD1 together with 1-methyl trypotophan and Virus 16;

Effects on tumor size were observed for a further 30 days. A greater tumor reduction in animals treated with combinations of virus and checkpoint blockade was demonstrated than in animals treated with the single treatment groups (see FIG. 11). Enhanced tumor reduction with Virus 16 together with both anti-PD1 and IDO inhibition was also demonstrated as compared to Virus 16 together with only anti-PD1 (see FIG. 11).

Enhanced activity of Virus 16 in combination with immune checkpoint blockade was also seen in A20 tumors (FIG. 12).

EXAMPLE 12

The Effect of the Expression of a Fusogenic Protein from an Oncolytic Virus of the Invention in Human Xenograft Models in Immune Deficient Mice The GALV R- protein causes cell to cell fusion in human cells but not in mouse cells. However, human xenograft tumors grown in immune deficient mice can be used to assess the effects of GALV expression on anti-tumor efficacy.

The utility of the invention was therefore further demonstrated by administering A549 human lung cancer cells into the flanks of nude mice and allowing the tumors to grow to approximately 0.5 cm in diameter.

The following treatments were then administered to groups of mice (ten per group), into tumor containing flank of each mouse three times over one week:
 50 µl of vehicle;
 50 µl of $10^7$ pfu/ml of Virus 16 (expresses both mouse GM-CSF and GALV-R-);
 50 µl of $10^6$ pfu/ml of Virus 16;
 50 µl of $10^5$ pfu/ml of Virus 16;
 50 µl of $10^7$ pfu/ml of Virus 19 (expresses only mouse GM-CSF);
 50 µl of $10^6$ pfu/ml of Virus 19;
 50 µl of $10^5$ pfu/ml of Virus 19.

Figure 14:
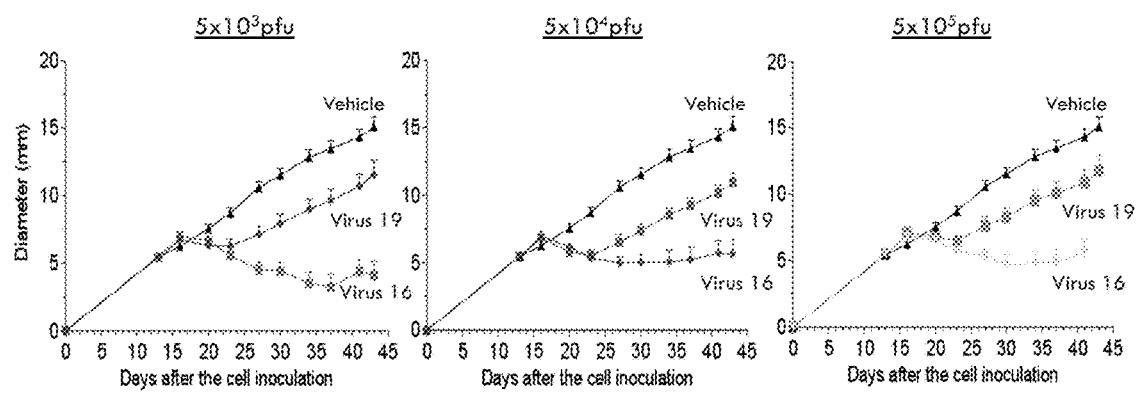
FIG. 14 shows anti-tumor effects of Virus 16 and Virus 19 in a human xenograft model (A549). There were three injections of Virus 16, Virus 19 or of vehicle over one week at three different dose levels (N=10/group). The doses of the viruses used is indicated. The anti-tumor effects of Virus 16 which expresses GALV were better than those of Virus 19 which does not express GALV.

Effects on tumor growth were then observed for a further ≈30 days. This experiment demonstrated superior tumor control and shrinkage with the virus expressing GALV-R- in both tumor models (see FIG. 14).

EXAMPLE 13

Figure 13:
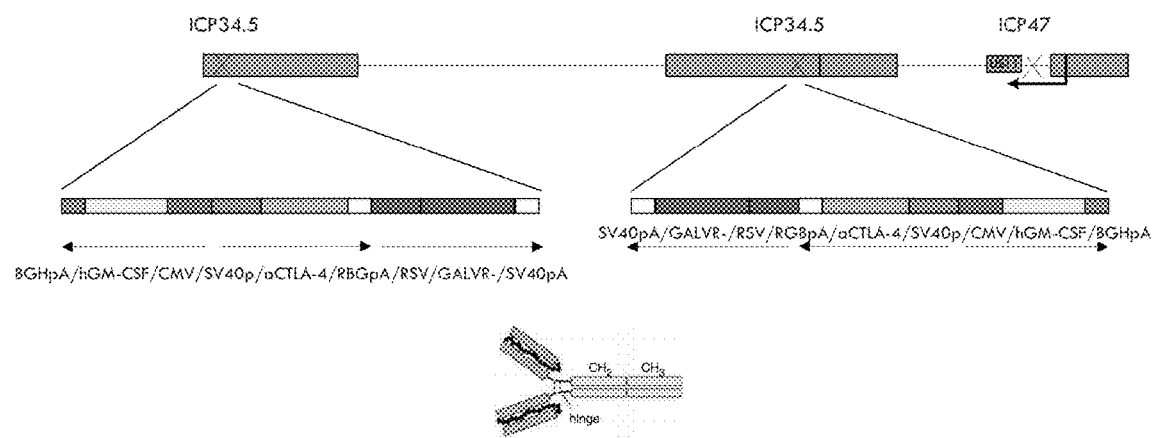
FIG. 13 shows the structure of ICP34.5 and ICP47 deleted viruses expressing GALVR-, GM-CSF and codon optimized anti-mouse or anti-human CTLA-4 antibody constructs (secreted scFv molecules linked to human or mouse IgG1 Fc regions). The scFvs contain the linked ([G$_4$S]$_3$) light and heavy variable chains from antibody 9D9 (US2011044953: mouse version) and from ipilimumab (US20150283234; human version). The resulting structure of the CTLA-4 inhibitor is also shown.
Figure 16:
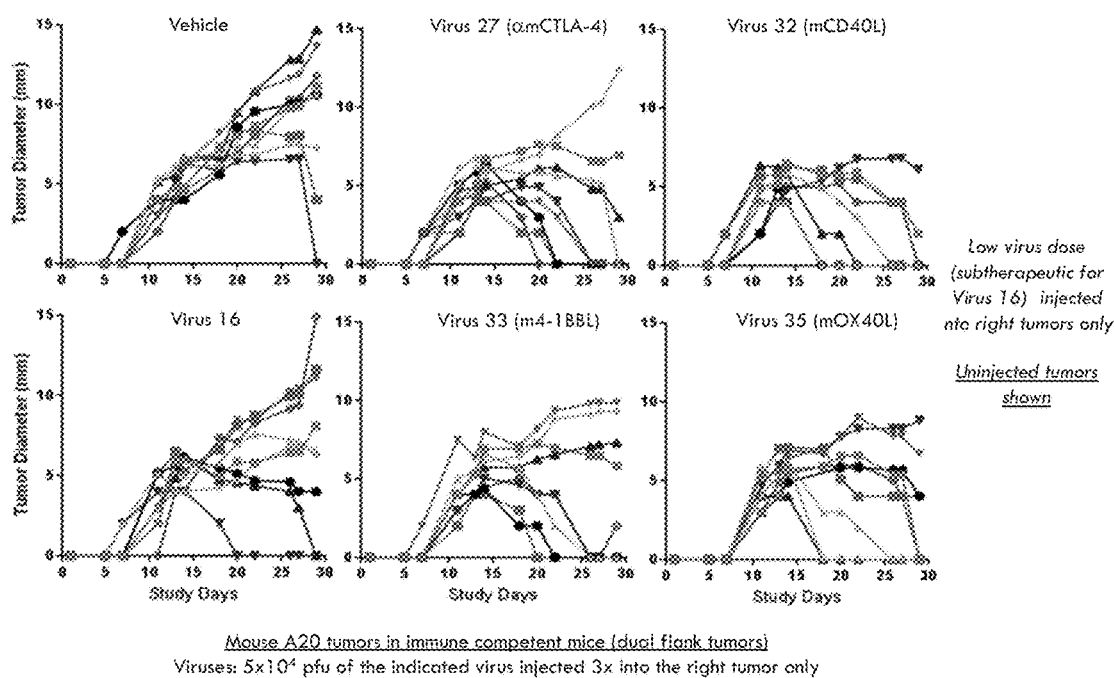
FIG. 16 shows the anti-tumor effects of viruses expressing anti-mCTLA-4 (virus 27), mCD40L (virus 32), mOX40L (virus 35), m4-2BBL (virus 33), each also with mGM-CSF and GALV-R- compared to virus 16 (expresses GALV and mGM-CSF).

Expression of Two Immune Stimulatory Molecules from a Virus Expressing a Fusogenic Protein Viruses similar to the GALV-R- and mGM-CSF expressing virus described above (Virus 16) were constructed, but additionally expressing mouse versions of CD40L (virus 32), ICOSL (virus 36), OX40L (virus 35), 4-1BBL (virus 33) and GITRL (virus 34). Here, instead of using a plasmid containing ICP34.5 flanking regions and an expression cassette comprising GM-CSF and GALV-R- driven by a CMV and an RSV promoter, a plasmid containing ICP34.5 flanking regions and an expression cassette comprising GM-CSF, GALV and the additional proteins driven by a CMV, an RSV and an MMLV promoter respectively were used for recombination with a virus containing GM-CSF, GALV and GFP inserted into ICP34.5. Non-GFP expressing plaques were again selected. Correct insertion was confirmed by PCR, and expression by western blotting and/or ELISA for the additional inserted gene. These viruses are shown in FIG. 5. Similarly, viruses expressing anti-mouse and anti-human CTLA-4 in addition to GALV and mGM-CSF were also constructed (Viruses 27 and 31 in FIG. 5 and see also FIG. 13). Effects of viruses expressing anti-mouse CTLA-4 (virus 27), mCD40L (virus 32), m4-1BBL (virus 33) or mOX40L (virus 35) in addition to mGM-CSF and GALVR- in vivo is shown in FIG. 16 which showed enhanced activity in A20 tumors as compared to virus 16 (expresses mGM-CSF and GALVR-). In these experiments tumors were induced in both flanks of mice, and virus or vehicle injected only into the right flank tumor. The dose of virus used was 5×10$^4$ pfu (50 ul of 1×10$^6$ pfu/ml in each case), given three times over one week. This dose level of virus is subtherapeutic for uninjected tumors for virus 16, which allows the benefits of the delivery of the additional molecules encoded by viruses 27, 32, 33 and 35 to clearly be seen.

Deposit Information

The following HSV1 strains were deposited at the ECACC, Culture Collections, Public Health England, Porton Down, Salisbury, SP4 0JG, United Kingdom on 19 Dec. 2016 by Replimune Limited and were allocated the indicated provisional accession numbers:

RH004A—Provisional Accession Number 16121902
RH015A—Provisional Accession Number 16121903
RH018A—Provisional Accession Number 16121904
RH021A—Provisional Accession Number 16121905
RH023A—Provisional Accession Number 16121906
RH031A—Provisional Accession Number 16121907
RH040B—Provisional Accession Number 16121908
RH047A—Provisional Accession Number 16121909.

The invention claimed is:

1. An oncolytic virus comprising: (i) a heterologous GM-CSF-encoding gene; and (ii) a heterologous CTLA-4 inhibitor encoding gene, wherein both heterologous genes are inserted into the genome of the virus.

2. The virus of claim 1, wherein the CTLA-4 inhibitor is a CTLA-4 antibody or fragment thereof.

3. The virus of claim 1, further comprising a fusogenic protein-encoding gene.

4. The virus of claim 3 where the fusogenic protein is selected from the group consisting of vesicular stomatitis virus (VSV) G-protein, syncitin-1, syncitin-2, simian virus 5 (SV5) F-protein, measles virus (MV) H-protein, MV F-protein, respiratory syncytial virus (RSV) F-protein and a glycoprotein from gibbon ape leukemia virus (GALV), murine leukemia virus (MLV), Mason-Pfizer monkey virus (MPMV) and equine infectious anaemia virus (EIAV) from which the R peptide has been deleted.

5. The virus of claim 3, wherein the fusogenic protein is the glycoprotein from gibbon ape leukemia virus (GALV) and has the R transmembrane peptide mutated or removed (GALV-R-).

6. The virus of claim 1, which encodes more than one immune co-stimulatory pathway activating molecule.

7. The virus of claim 1, which is a modified clinical isolate of a virus.

8. The virus of claim 1, which is a modified clinical isolate of a virus, wherein the clinical isolate kills two or more tumor cell lines more rapidly and/or at a lower dose in vitro than one or more reference clinical isolates of the same species of virus.

9. The virus of claim 7, wherein the clinical isolate is
strain RH018A having the accession number ECCAC 16121904;
strain RH004A having the accession number ECCAC 16121902;

strain RH031A having the accession number ECCAC 16121907;

strain RH040B having the accession number ECCAC 16121908;

strain RH015A having the accession number ECCAC 16121903;

strain RH021A having the accession number ECCAC 16121905;

strain RH023A having the accession number ECCAC 16121906; or strain RH047A having the accession number ECCAC 16121909.

10. The virus of claim 1, which is selected from the group consisting of herpes viruses, pox viruses, adenoviruses, retroviruses, rhabdoviruses, paramyxoviruses and reoviruses.

11. The virus of claim 1, which is a herpes simplex virus (HSV).

12. The virus of claim 11 which is a HSV1.

13. The virus of claim 11, wherein the GM-CSF-encoding gene and the CTLA-4 inhibitor encoding gene are inserted into the ICP34.5 encoding locus, either by insertion, or partial or complete deletion, in a back to back orientation in relation to each other, each under separate regulatory control.

14. The virus of claim 12, wherein the HSV:
(a) does not express functional ICP34.5;
(b) does not express functional ICP47; and/or
(c) expresses the US11 gene as an immediate early gene.

15. The virus of claim 1, wherein the sequence of a gene encoding GM-CSF and/or the sequence of the gene encoding a CTLA-4 inhibitor is codon optimized so as to increase expression levels in target cells.

16. A pharmaceutical composition comprising the virus of claim 1 and a pharmaceutically acceptable carrier or diluent.

17. A product of manufacture comprising a virus according to claim 1 in a sterile vial, ampoule or syringe.

18. A method of treating cancer, which comprises administering a therapeutically effective amount of the virus of claim 1 to a patient in need thereof.

19. The method of claim 18, which further comprises administering a therapeutically effective amount of a further anti-cancer agent to a patient in need thereof.

20. The method of claim 19, wherein the further anti-cancer agent is selected from the group consisting of an agent targeting an immune co-inhibitory or immune co-stimulatory pathway, radiation and/or chemotherapy, an agent that targets a specific genetic mutation which occurs in tumors, an agent intended to induce an immune response to one or more tumor antigen(s) or neoantigen(s), a cellular product derived from T cells or NK cells, an agent intended to stimulate the STING, cGAS, TLR or other innate immune response and/or inflammatory pathway, a second virus optionally an oncolytic virus, and combinations thereof.

21. The method of claim 19, wherein the virus and the further anti-cancer agent(s) are administered separately.

22. The method of claim 19, wherein the virus and the further anti-cancer agent(s) are administered concurrently.

23. The method of claim 19, wherein the cancer is a solid tumor.

24. The method of claim 20, wherein the further anti-cancer agent comprises an antibody.

25. The method of claim 20, wherein the further anti-cancer agent is a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a KIR inhibitor, a SLAMF7 inhibitor, a CEACAM1 inhibitor or a CD47 inhibitor.

26. The method of claim 20, wherein the further anti-cancer agent is a GITR agonist, a 4-1-BB agonist, an OX40 agonist, a CD40 agonist or an ICOS agonist.

* * * * *

Disclaimer

10,947,513 B2 - Robert Coffin, Oxford (GB). ENGINEERED VIRUS Patent dated March 16, 2021. Disclaimer filed March 15, 2022, by the assignee, Replimune limited.

I hereby disclaim the following complete claims 1, 2, 3, 4, 5, 6, 7, 8, 10, 11, 12, 14, 15, 16, 17, 18, 19, 20, 21, 22, 23, 24, 25 and 26 of said patent.

*(Official Gazette, September 6, 2022)*

SEQUENCE LISTING

```
<160> NUMBER OF SEQ ID NOS: 45

<210> SEQ ID NO 1
<211> LENGTH: 426
<212> TYPE: DNA
<213> ORGANISM: Mus musculus

<400> SEQUENCE: 1
atgtggctgc agaatttact tttcctgggc attgtggtct acagcctctc agcacccacc        60
cgctcaccca tcactgtcac ccggccttgg aagcatgtag aggccatcaa agaagccctg       120
aacctcctgg atgacatgcc tgtcacattg aatgaagagg tagaagtcgt ctctaacgag       180
ttctccttca agaagctaac atgtgtgcag acccgcctga agatattcga gcagggtcta       240
cggggcaatt tcaccaaact caagggcgcc ttgaacatga cagccagcta ctaccagaca       300
tactgccccc caactccgga aacggactgt gaaacacaag ttaccaccta tgcggatttc       360
atagacagcc ttaaaacctt tctgactgat atcccctttg aatgcaaaaa accagtccaa       420
aaatga                                                                  426

<210> SEQ ID NO 2
<211> LENGTH: 426
<212> TYPE: DNA
<213> ORGANISM: Mus musculus

<400> SEQUENCE: 2
atgtggctcc agaacctcct cttcctcggt atcgtcgtgt attcactctc cgcacctact        60
cgctcaccta tcactgtcac cagaccctgg aagcacgtgg aggccatcaa ggaggctctg       120
aacctgctgg acgatatgcc agtgaccctg aacgaggagg tggaggtggt gagcaacgag       180
ttctccttta agaagctgac ctgcgtgcag acaaggctga agatcttcga gcagggcctg       240
agaggaaact ttaccaagct gaagggcgcc ctgaacatga ccgcttctta ctaccagaca       300
tactgccccc ctacccccga cagactgt gagacacagg tgaccacata cgccgacttc       360
attgatagcc tgaaaacatt cctgaccgac attccatttg agtgtaagaa gcccgtccag       420
aagtaa                                                                  426

<210> SEQ ID NO 3
<211> LENGTH: 435
<212> TYPE: DNA
<213> ORGANISM: Homo sapiens

<400> SEQUENCE: 3
atgtggctgc agagcctgct gctcttgggc actgtggcct gcagcatctc tgcacccgcc        60
cgctcgccca gccccagcac gcagccctgg gagcatgtga atgccatcca ggaggcccgg       120
```

```
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaagcagc actgccctcc aaccccggaa acttcctgtg caacccagat tatcaccttt    360
gaaagtttca agagaacct gaaggacttt ctgcttgtca tcccctttga ctgctgggag    420
ccagtccagg agtga                                                     435
```

<210> SEQ ID NO 4
<211> LENGTH: 435
<212> TYPE: DNA
<213> ORGANISM: Homo sapiens

<400> SEQUENCE: 4

```
atgtggctgc agtccctgct gctgctgggc accgtcgcct gttctatttc cgcacccgca     60
aggtcaccaa gtccatctac tcagccttgg gagcacgtga acgcaatcca ggaggcacgg    120
cggctgctga acctgagccg ggacaccgcc gccgagatga acgagacagt ggaagtgatc    180
agcgagatgt tcgatctgca ggagcccacc tgcctgcaga caaggctgga gctgtacaag    240
cagggcctgc gcggctctct gaccaagctg aagggcccac tgacaatgat ggccagccac    300
tataagcagc actgcccccc tacccccgag acaagctgtg ccacccagat catcacattc    360
gagtccttta aggagaacct gaaggatttt ctgctggtca ttccatttga ttgttgggag    420
cccgtccagg agtaa                                                     435
```

<210> SEQ ID NO 5
<211> LENGTH: 141
<212> TYPE: PRT
<213> ORGANISM: Mus musculus

<400> SEQUENCE: 5

```
Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140
```

<210> SEQ ID NO 6
<211> LENGTH: 144
<212> TYPE: PRT
<213> ORGANISM: Homo sapiens

<400> SEQUENCE: 6

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 7
<211> LENGTH: 2010
<212> TYPE: DNA
<213> ORGANISM: Gibbon leukemia virus

<400> SEQUENCE: 7
atggtattgc tgcctgggtc catgcttctc acctcaaacc tgcaccacct tcggcaccag      60
atgagtcctg ggagctggaa aagactgatc atcctcttaa gctgcgtatt cggcggcggc     120
gggacgagtc tgcaaaataa gaaccccac cagcccatga ccctcacttg gcaggtactg      180
tcccaaactg agacgttgt ctgggataca aaggcagtcc agccccttg gacttggtgg       240 cccacactta aacctgatgt atgtgccttg cggctagtc ttgagtcctg ggatatcccg      300
ggaaccgatg tctcgtcctc taaacgagtc agacctccgg actcagacta tactgccgct    360
tataagcaaa tcacctgggg agccataggg tgcagctacc ctcgggctag gactagaatg    420
gcaagctcta ccttctacgt atgtccccgg gatggccgga ccctttcaga agctagaagg    480 tgcgggggc tagaatccct atactgtaaa gaatgggatt gtgagaccac ggggaccggt     540
tattggctat ctaaatcctc aaaagacctc ataactgtaa atgggaccac aaatagcgaa    600
tggactcaaa aatttcaaca gtgtcaccag accggctggt gtaacccct aaaatagat     660 ttcacagaca aaggaaaatt atccaaggac tggataacgg gaaaaacctg gggattaaga   720
ttctatgtgt ctggacatcc aggcgtacag ttcaccattc gcttaaaaat caccaacatg   780
ccagctgtgg cagtaggtcc tgacctcgtc cttgtggaac aaggaccctcc tagaacgtcc  840 ctcgctctcc cacctcctct tccccccaagg gaagcgccac cgccatctct ccccgactct  900
aactccacag ccctggcgac tagtgcacaa actcccacgg tgagaaaaac aattgttacc  960
ctaaacactc cgcctcccac cacaggcgac agacttttg atcttgtgca gggggccttc   1020
ctaaccttaa atgctaccaa cccaggggcc actgagtctt gctggctttg tttggccatg  1080
ggcccccctt attatgaagc aatagcctca tcaggagagg tcgcctactc caccgacctt 1140
gaccggtgcc gctggggac caaggaaag ctcacccctca ctgaggtctc aggacacggg    1200
ttgtgcatag gaaaggtgcc ctttacccat cagcatctct gcaatcagac ctatctcatc 1260
aattcctccg gagaccatca gtatctgctc ccctccaacc atagctggtg ggcttgcagc 1320

```
actggcctca cccttgcct ctccacctca gttttaatc agactagaga tttctgtatc    1380
caggtccagc tgattcctcg catctattac tatcctgaag aagttttgtt acaggcctat    1440
gacaattctc accccaggac taaaagagag gctgtctcac ttaccctagc tgttttactg    1500
gggttgggaa tcacggcggg aataggtact ggttcaactg ccttaattaa aggacctata    1560
gacctccagc aaggcctgac aagcctccag atcgccatag atgctgacct ccgggccctc    1620
caagactcag tcagcaagtt agaggactca ctgacttccc tgtccgaggt agtgctccaa    1680
aataggagag gccttgactt gctgtttcta aaagaaggtg gcctctgtgc ggccctaaag    1740
gaagagtgct gttttacat agaccactca ggtgcagtac gggactccat gaaaaaactc    1800
aaagaaaaac tggataaaag acagttagag cgccagaaaa gccaaaactg gtatgaagga    1860
tggttcaata actcccttg gttcactacc ctgctatcaa ccatcgctgg gcccctatta    1920
ctcctccttc tgttgctcat cctcgggcca tgcatcatca ataagttagt tcaattcatc    1980
aatgatagga taagtgcagt taaaatttaa                                    2010

<210> SEQ ID NO 8
<211> LENGTH: 2013
<212> TYPE: DNA
<213> ORGANISM: Gibbon leukemia virus

<400> SEQUENCE: 8
accatggtcc tgctgcctgg gtctatgctg ctgacttcta acctgcacca cctgcgacac      60
cagatgtctc ccggctcatg gaaacggctg atcatcctgc tgagctgcgt gttcggagga     120
ggaggcacct ccctgcagaa caagaatcct caccagccaa tgaccctgac atggcaggtg     180
ctgtcccaga caggcgacgt ggtgtgggat accaaggcag tgcagccacc ttggacatgg     240
tggcccaccc tgaagcctga cgtgtgcgcc ctggccgcct ccctggagtc ttgggacatc     300
cccggcacag acgtgagcag cagcaagagg gtgagaccac ccgactctga ttatacagcc     360
gcctacaagc agatcacctg ggcgccatc ggctgtagct atcctcgggc ccgcacaagg      420
atggccagct ccaccttta cgtgtgccca cgcgacggaa ggaccctgtc tgaggcaagg     480
agatgtggcg gcctggagag cctgtattgc aaggagtggg attgtgagac cacaggcaca     540
ggctactggc tgtctaagtc tagcaaggac ctgatcaccg tgaagtggga tcagaacagc     600
gagtggacac agaagttcca gcagtgccac cagaccggct ggtgtaatcc cctgaagatc     660
gactttacag ataagggcaa gctgtccaag gactggatca ccggcaagac atggggcctg     720
agattctacg tgtctggcca ccctggcgtg cagtttacaa tccggctgaa gatcaccaac     780
atgccagcag tggcagtggg accagacctg gtgctggtgg agcagggacc tccacgcacc     840
tccctggccc tgccccctcc actgccccct agggaggccc caccccctag cctgcccgat     900
tctaacagca cagccctggc cacctccgcc cagaccccta cagtgcgcaa gaccatcgtg     960
acactgaata ccccaccccc taccacaggc gacaggctgt cgatctggt gcagggcgcc    1020 tttctgacac tgaacgccac caatcctggc gcaaccgaga gctgctggct gtgcctggct    1080
atgggcccac cctactatga ggcaatcgcc tcctctggag aggtggcata ttccacagac    1140
ctggatagat gcagatgggg caccccagggc aagctgaccc tgacagaggt gtctggccac    1200
ggcctgtgca tcggcaaggt gccattcaca caccagcacc tgtgcaacca gaccctgagc    1260
atcaatagct ccggcgacca ccagtacctg ctgccaagca accactcctg gtgggcatgc    1320
tccacaggac tgacccatg tctgagcacc agcgtgttca accagaccag agacttttgt    1380
```

-continued

```
atccaggtgc agctgatccc tcggatctac tattacccag aggaggtgct gctgcaggcc    1440
tatgataatt cccacccaag aacaaagagg gaggccgtgt ctctgaccct ggccgtgctg    1500
ctgggactgg aatcacagc aggaatcggc acaggcagca ccgccctgat caagggacca    1560
atcgacctgc agcagggact gacctccctg cagatcgcca tcgacgccga tctgagagcc    1620
ctgcaggaca gcgtgtccaa gctggaggat tctctgacct ctctgagcga ggtggtgctg    1680
cagaacagga ggggcctgga cctgctgttc ctgaaggagg gaggactgtg cgccgccctg    1740
aaggaggagt gctgtttta tatcgaccac tctggcgccg tgcggatag catgaagaag    1800 ctgaaggaga agctggataa cgccagctg gagaggcaga gagccagaa ttggtacgag    1860 ggctggttca acaattcccc ctggtttacc acactgctgt ctaccatcgc aggacctctg    1920
ttattactgc tgctgctgct gatcctgggc ccatgtatca tcaacaagct ggtgcagttt    1980
atcaacgacc gaatctccgc agtgaaaatc taa                                  2013
```

<210> SEQ ID NO 9
<211> LENGTH: 669
<212> TYPE: PRT
<213> ORGANISM: Gibbon leukemia virus

<400> SEQUENCE: 9

```
Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
                20                  25                  30

Leu Ser Cys Val Phe Gly Gly Gly Thr Ser Leu Gln Asn Lys Asn
            35                  40                  45

Pro His Gln Pro Met Thr Leu Thr Trp Gln Val Leu Ser Gln Thr Gly
        50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Ser Lys Arg Val Arg Pro
                100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
        130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
```

260                 265                 270
    Glu Gln Gly Pro Pro Arg Thr Ser Leu Ala Leu Pro Pro Leu Pro
                275                 280                 285

Pro Arg Glu Ala Pro Pro Ser Leu Pro Asp Ser Asn Ser Thr Ala
            290                 295                 300

Leu Ala Thr Ser Ala Gln Thr Pro Thr Val Arg Lys Thr Ile Val Thr
    305                 310                 315                 320

Leu Asn Thr Pro Pro Thr Thr Gly Asp Arg Leu Phe Asp Leu Val
                    325                 330                 335

Gln Gly Ala Phe Leu Thr Leu Asn Ala Thr Asn Pro Gly Ala Thr Glu
                340                 345                 350

Ser Cys Trp Leu Cys Leu Ala Met Gly Pro Pro Tyr Tyr Glu Ala Ile
                355                 360                 365

Ala Ser Ser Gly Glu Val Ala Tyr Ser Thr Asp Leu Asp Arg Cys Arg
            370                 375                 380

Trp Gly Thr Gln Gly Lys Leu Thr Leu Thr Glu Val Ser Gly His Gly
    385                 390                 395                 400

Leu Cys Ile Gly Lys Val Pro Phe Thr His Gln His Leu Cys Asn Gln
                    405                 410                 415

Thr Leu Ser Ile Asn Ser Ser Gly Asp His Gln Tyr Leu Leu Pro Ser
                420                 425                 430

Asn His Ser Trp Trp Ala Cys Ser Thr Gly Leu Thr Pro Cys Leu Ser
                435                 440                 445

Thr Ser Val Phe Asn Gln Thr Arg Asp Phe Cys Ile Gln Val Gln Leu
    450                 455                 460

Ile Pro Arg Ile Tyr Tyr Tyr Pro Glu Glu Val Leu Leu Gln Ala Tyr
    465                 470                 475                 480

Asp Asn Ser His Pro Arg Thr Lys Arg Glu Ala Val Ser Leu Thr Leu
                    485                 490                 495

Ala Val Leu Leu Gly Leu Gly Ile Thr Ala Gly Ile Gly Thr Gly Ser
                500                 505                 510

Thr Ala Leu Ile Lys Gly Pro Ile Asp Leu Gln Gln Gly Leu Thr Ser
                515                 520                 525

Leu Gln Ile Ala Ile Asp Ala Asp Leu Arg Ala Leu Gln Asp Ser Val
            530                 535                 540

Ser Lys Leu Glu Asp Ser Leu Thr Ser Leu Ser Glu Val Val Leu Gln
    545                 550                 555                 560

Asn Arg Arg Gly Leu Asp Leu Leu Phe Leu Lys Glu Gly Gly Leu Cys
                    565                 570                 575

Ala Ala Leu Lys Glu Glu Cys Cys Phe Tyr Ile Asp His Ser Gly Ala
                580                 585                 590

Val Arg Asp Ser Met Lys Lys Leu Lys Glu Lys Leu Asp Lys Arg Gln
                595                 600                 605

Leu Glu Arg Gln Lys Ser Gln Asn Trp Tyr Glu Gly Trp Phe Asn Asn
            610                 615                 620

Ser Pro Trp Phe Thr Thr Leu Leu Ser Thr Ile Ala Gly Pro Leu Leu
    625                 630                 635                 640

Leu Leu Leu Leu Leu Leu Ile Leu Gly Pro Cys Ile Ile Asn Lys Leu
                    645                 650                 655

Val Gln Phe Ile Asn Asp Arg Ile Ser Ala Val Lys Ile
                660                 665

<210> SEQ ID NO 10

<211> LENGTH: 759
<212> TYPE: DNA
<213> ORGANISM: Artificial Sequence
<220> FEATURE:
<223> OTHER INFORMATION: Homo sapiens

<400> SEQUENCE: 10

```
atgatcgaga cctacaatca gacaagccca cggtccgccg caaccggact gcctatcagc      60
atgaagatct tcatgtacct gctgaccgtg tttctgatca cacagatgat cggctccgcc     120
ctgttcgccg tgtatctgca caggagactg acaagatcg aggatgagcg caatctgcac      180
gaggacttcg tgtttatgaa gaccatccag cggtgcaaca caggcgagag gagcctgtct     240
ctgctgaatt gtgaggagat caagtcccag ttcgagggct tgtgaagga tatcatgctg      300
aacaaggagg agacaaagaa ggacgaggat ccacagatcg cagcacacgt ggtgtccgag     360
gcaaactcta atgccgccag cgtgctgcag tgggccaaga agggctacta taccatgaag     420
tctaacctgg tgacactgga aatggcaag cagctgaccg tgaagaggca gggcctgtac      480
tatatctatg cccaggtgac attctgctct aacagagagg caagctccca ggcacccttc     540
atcgtgggac tgtggctgaa gccctctagc ggcagcgaga ggatcctgct gaaggccgcc     600
aatacccact cctctagcca gctgtgcgag cagcagtcca tccacctggg aggcgtgttc     660
gagctgcagc ctggagccag cgtgttcgtg aacgtgacag acccatctca ggtgagccac     720
ggcaccggct tcacaagctt tggcctgctg aagctgtga                            759
```

<210> SEQ ID NO 11
<211> LENGTH: 252
<212> TYPE: PRT
<213> ORGANISM: Artificial Sequence
<220> FEATURE:
<223> OTHER INFORMATION: Homo sapiens

<400> SEQUENCE: 11

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Asp Glu Asp Pro Gln
            100                 105                 110

Ile Ala Ala His Val Val Ser Glu Ala Asn Ser Asn Ala Ala Ser Val
        115                 120                 125

Leu Gln Trp Ala Lys Lys Gly Tyr Tyr Thr Met Lys Ser Asn Leu Val
    130                 135                 140

Thr Leu Glu Asn Gly Lys Gln Leu Thr Val Lys Arg Gln Gly Leu Tyr
145                 150                 155                 160

Tyr Ile Tyr Ala Gln Val Thr Phe Cys Ser Asn Arg Glu Ala Ser Ser
                165                 170                 175

Gln Ala Pro Phe Ile Val Gly Leu Trp Leu Lys Pro Ser Ser Gly Ser
            180                 185                 190
```

Glu Arg Ile Leu Leu Lys Ala Ala Asn Thr His Ser Ser Gln Leu
        195                 200                 205

Cys Glu Gln Gln Ser Ile His Leu Gly Gly Val Phe Glu Leu Gln Pro
    210                 215                 220

Gly Ala Ser Val Phe Val Asn Val Thr Asp Pro Ser Gln Val Ser His
225                 230                 235                 240

Gly Thr Gly Phe Thr Ser Phe Gly Leu Leu Lys Leu
                245                 250

<210> SEQ ID NO 12
<211> LENGTH: 1416
<212> TYPE: DNA
<213> ORGANISM: Homo sapiens

<400> SEQUENCE: 12

```
atgctgccct ttctgagcat gctggtgctg ctggtgcagc tctgggaaaa cctgggagcc      60
gagatgaaga gcctgtccca gagatctgtg cctaacacct gcacactggt catgtgcagc     120
cccaccgaga atggactgcc tggaagggac ggaagggatg aagggagggg ccctcggggc     180
gagaagggcg acccaggact gcctggacca atgggactga gcggactgca gggaccaaca     240
ggacctgtgg gaccaaaggg agagaacgga tccgccggag agccaggccc taagggcgag     300
aggggcctgt ctggcccccc tggcctgcca ggcatcccag ccccgccgg caaggagggc     360
ccatccggca gcagggcaa tatcggcccc cagggcaagc tggcccaaa gggcgaggca     420
ggaccaaagg gagaagtggg agcacctggc atgcagggat ccaccggagc aaagggatct     480
acaggaccaa agggcgagcg cggcgcccca ggcgtgcagg gcgcccccgg caatgcagga     540
gcagcaggac cagcaggacc tgcaggccca cagggcgccc tggctctag gggcccaccc     600
ggcctgaagg gcgacagggg agtgcctggc gataggggca tcaagggaga gagcggactg     660
ccagattccg ccgccctgag gcagcagatg gaggccctga agggcaagct gcagaggctg     720
gaggtggcct tctcccacta ccagaaggcc gccctgtttc agacggcca caggagactg     780
gacaagatcg aggatgagcg caacctgcac gaggatttcg tgtttatgaa gaccatccag     840
agatgcaaca caggcgagcg gtctctgagc ctgctgaatt gtgaggagat caagtctcag     900
ttcgagggct ttgtgaagga catcatgctg aacaaggagg agaccaagaa ggagaatagc     960
ttcgagatgc agaagggcga tcagaatccc cagatcgcag cacacgtgat cagcgaggca    1020
agctccaaga ccacatccgt gctgcagtgg gccgagaagg gctactatac catgtccaac    1080
aatctggtga cactggagaa cggcaagcag ctgaccgtga agacaggg cctgtactat    1140
atctatgccc aggtgacatt ctgctctaat cgggaggcct ctagccaggc ccctttttatc    1200
gcctctctgt gcctgaagag cccaggcaga ttcgagcgga tcctgctgag ggccgccaac    1260
acccactcct ctgccaagcc atgcggacag cagagcatcc acctgggagg cgtgttcgag    1320
ctgcagccag agcctccgt gtttgtgaat gtgacagacc catcccaggt gtctcacgga    1380
accggcttca tcctttttgg cctgctgaag ctgtga                              1416
```

<210> SEQ ID NO 13
<211> LENGTH: 471
<212> TYPE: PRT
<213> ORGANISM: Homo sapiens

<400> SEQUENCE: 13

Met Leu Pro Phe Leu Ser Met Leu Val Leu Val Gln Pro Leu Gly
1               5                   10                  15

```
Asn Leu Gly Ala Glu Met Lys Ser Leu Ser Gln Arg Ser Val Pro Asn
             20                  25                  30

Thr Cys Thr Leu Val Met Cys Ser Pro Thr Glu Asn Gly Leu Pro Gly
         35                  40                  45

Arg Asp Gly Arg Asp Gly Arg Glu Gly Pro Arg Gly Glu Lys Gly Asp
 50                  55                  60

Pro Gly Leu Pro Gly Pro Met Gly Leu Ser Gly Leu Gln Gly Pro Thr
 65                  70                  75                  80

Gly Pro Val Gly Pro Lys Gly Glu Asn Gly Ser Ala Gly Glu Pro Gly
                 85                  90                  95

Pro Lys Gly Glu Arg Gly Leu Ser Gly Pro Gly Leu Pro Gly Ile
             100                 105                 110

Pro Gly Pro Ala Gly Lys Glu Gly Pro Ser Gly Lys Gln Gly Asn Ile
             115                 120                 125

Gly Pro Gln Gly Lys Pro Gly Pro Lys Gly Glu Ala Gly Pro Lys Gly
 130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                 165                 170                 175

Gly Asn Ala Gly Ala Ala Gly Pro Ala Gly Pro Ala Gly Pro Gln Gly
             180                 185                 190

Ala Pro Gly Ser Arg Gly Pro Pro Gly Leu Lys Gly Asp Arg Gly Val
             195                 200                 205

Pro Gly Asp Arg Gly Ile Lys Gly Glu Ser Gly Leu Pro Asp Ser Ala
 210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                 245                 250                 255

His Arg Arg Leu Asp Lys Ile Glu Asp Glu Arg Asn Leu His Glu Asp
             260                 265                 270

Phe Val Phe Met Lys Thr Ile Gln Arg Cys Asn Thr Gly Glu Arg Ser
             275                 280                 285

Leu Ser Leu Leu Asn Cys Glu Glu Ile Lys Ser Gln Phe Glu Gly Phe
 290                 295                 300

Val Lys Asp Ile Met Leu Asn Lys Glu Glu Thr Lys Lys Glu Asn Ser
305                 310                 315                 320

Phe Glu Met Gln Lys Gly Asp Gln Asn Pro Gln Ile Ala Ala His Val
                 325                 330                 335

Ile Ser Glu Ala Ser Ser Lys Thr Thr Ser Val Leu Gln Trp Ala Glu
             340                 345                 350

Lys Gly Tyr Tyr Thr Met Ser Asn Asn Leu Val Thr Leu Glu Asn Gly
             355                 360                 365

Lys Gln Leu Thr Val Lys Arg Gln Gly Leu Tyr Tyr Ile Tyr Ala Gln
 370                 375                 380

Val Thr Phe Cys Ser Asn Arg Glu Ala Ser Ser Gln Ala Pro Phe Ile
385                 390                 395                 400

Ala Ser Leu Cys Leu Lys Ser Pro Gly Arg Phe Glu Arg Ile Leu Leu
                 405                 410                 415

Arg Ala Ala Asn Thr His Ser Ser Ala Lys Pro Cys Gly Gln Gln Ser
             420                 425                 430
```

Ile His Leu Gly Gly Val Phe Glu Leu Gln Pro Gly Ala Ser Val Phe
                435                      440                      445

Val Asn Val Thr Asp Pro Ser Gln Val Ser His Gly Thr Gly Phe Thr
    450                      455                      460

Ser Phe Gly Leu Leu Lys Leu
465                    470

<210> SEQ ID NO 14
<211> LENGTH: 1412
<212> TYPE: DNA
<213> ORGANISM: Mus musculus

<400> SEQUENCE: 14

```
atgctgccct tcctgagcat gctggtgctg ctggtgcagc tctgggcaa tctgggcgcc      60
gagatgaagt ccctgtctca gaggagcgtg ccaaacacct gcacactggt catgtgctct     120
ccaaccgaga atggactgcc aggaagggac ggaagagatg aagggaggg accaagggga     180
gagaagggcg accctggact gcctggacca atgggactgt ccggactgca ggaccaaca     240
ggccctgtgg gaccaaaggg agagaatgga agcgccggag agccaggacc taagggagag     300
aggggcctgt ccggcccccc tggcctgcct ggcatcccag gccccgccgg caaggagggc     360
ccttctggca gcagggcaa catcggacca cagggcaagc tggaccaaa gggagaggca     420
ggaccaaagg gagaagtggg agcacccggc atgcagggca gcaccggagc aaagggatcc     480
accggcccta agggagagag aggagcacct ggagtgcagg gcgcccagg caatgcagga     540
gcagcaggac cagcaggacc tgcaggccca cagggcgccc caggcagccg ggcccaccc     600
ggcctgaagg gcgacagggg agtgccaggc gatagggca tcaagggaga gtccggactg     660
ccagactctg ccgccctgag gcagcagatg gaggccctga aggcaagct gcagaggctg     720
gaggtggcct tctcccacta ccagaaggcc gccctgtttc agacggaca caggagactg     780
gataaggtgg aggaggaggt gaacctgcac gaggatttcg tgttcatcaa gaagctgaag     840
aggtgcaaca agggcgaggg cagcctgtcc ctgctgaatt gtgaggagat gcggcgccag     900
ttcgaggacc tggtgaagga tatcaccctg aacaaggagg agaagaagga gaattctttt     960
gagatgcaga ggggcgacga ggatcctcag atcgcagcac acgtggtgtc cgaggcaaac    1020
tctaatgccg ccagcgtgct gcagtgggcc aagaagggct actataccat gaagtctaac    1080
ctggtcatgc tggagaatgg caagcagctg acagtgaaga gagagggcct gtactacgtg    1140
tacacccagg tgacattctg cagcaacaga gagcccagct cccagcggcc ttttatcgtg    1200
ggcctgtggc tgaagccctc tatcggaagc gagaggatcc tgctgaaggc agccaatacc    1260
cactctagct cccagctgtg cgagcagcag tccgtgcacc tgggaggcgt gttcgagctg    1320
caggcaggag caagcgtgtt cgtgaacgga cagaggccag ccaggtcatc cacagagtgg    1380
gcttctctag ctttggcctg ctgaagctgt ga                                   1412
```

<210> SEQ ID NO 15
<211> LENGTH: 470
<212> TYPE: PRT
<213> ORGANISM: Mus musculus

<400> SEQUENCE: 15

Met Leu Pro Phe Leu Ser Met Leu Val Leu Leu Val Gln Pro Leu Gly
1               5                  10                 15

Asn Leu Gly Ala Glu Met Lys Ser Leu Ser Gln Arg Ser Val Pro Asn
                20                      25                      30

-continued

```
Thr Cys Thr Leu Val Met Cys Ser Pro Thr Glu Asn Gly Leu Pro Gly
        35                  40                  45

Arg Asp Gly Arg Asp Gly Arg Glu Gly Pro Arg Gly Glu Lys Gly Asp
 50                  55                  60

Pro Gly Leu Pro Gly Pro Met Gly Leu Ser Gly Leu Gln Gly Pro Thr
 65                  70                  75                  80

Gly Pro Val Gly Pro Lys Gly Glu Asn Gly Ser Ala Gly Glu Pro Gly
                 85                  90                  95

Pro Lys Gly Glu Arg Gly Leu Ser Gly Pro Pro Gly Leu Pro Gly Ile
                100                 105                 110

Pro Gly Pro Ala Gly Lys Glu Gly Pro Ser Gly Lys Gln Gly Asn Ile
            115                 120                 125

Gly Pro Gln Gly Lys Pro Gly Pro Lys Gly Glu Ala Gly Pro Lys Gly
        130                 135                 140

Glu Val Gly Ala Pro Gly Met Gln Gly Ser Thr Gly Ala Lys Gly Ser
145                 150                 155                 160

Thr Gly Pro Lys Gly Glu Arg Gly Ala Pro Gly Val Gln Gly Ala Pro
                165                 170                 175

Gly Asn Ala Gly Ala Ala Gly Pro Ala Gly Pro Ala Gly Pro Gln Gly
            180                 185                 190

Ala Pro Gly Ser Arg Gly Pro Pro Gly Leu Lys Gly Asp Arg Gly Val
        195                 200                 205

Pro Gly Asp Arg Gly Ile Lys Gly Glu Ser Gly Leu Pro Asp Ser Ala
210                 215                 220

Ala Leu Arg Gln Gln Met Glu Ala Leu Lys Gly Lys Leu Gln Arg Leu
225                 230                 235                 240

Glu Val Ala Phe Ser His Tyr Gln Lys Ala Ala Leu Phe Pro Asp Gly
                245                 250                 255

His Arg Arg Leu Asp Lys Val Glu Glu Glu Val Asn Leu His Glu Asp
            260                 265                 270

Phe Val Phe Ile Lys Lys Leu Lys Arg Cys Asn Lys Gly Glu Gly Ser
        275                 280                 285

Leu Ser Leu Leu Asn Cys Glu Glu Met Arg Arg Gln Phe Glu Asp Leu
290                 295                 300

Val Lys Asp Ile Thr Leu Asn Lys Glu Glu Lys Lys Glu Asn Ser Phe
305                 310                 315                 320

Glu Met Gln Arg Gly Asp Glu Asp Pro Gln Ile Ala Ala His Val Val
                325                 330                 335

Ser Glu Ala Asn Ser Asn Ala Ala Ser Val Leu Gln Trp Ala Lys Lys
            340                 345                 350

Gly Tyr Tyr Thr Met Lys Ser Asn Leu Val Met Leu Glu Asn Gly Lys
        355                 360                 365

Gln Leu Thr Val Lys Arg Glu Gly Leu Tyr Tyr Val Tyr Thr Gln Val
370                 375                 380

Thr Phe Cys Ser Asn Arg Glu Pro Ser Ser Gln Arg Pro Phe Ile Val
385                 390                 395                 400

Gly Leu Trp Leu Lys Pro Ser Ile Gly Ser Glu Arg Ile Leu Leu Lys
                405                 410                 415

Ala Ala Asn Thr His Ser Ser Gln Leu Cys Glu Gln Ser Val
            420                 425                 430

His Leu Gly Gly Val Phe Glu Leu Gln Ala Gly Ala Ser Val Phe Val
        435                 440                 445

Asn Val Thr Glu Ala Ser Gln Val Ile His Arg Val Gly Phe Ser Ser
```

-continued

```
                450             455             460
Phe Gly Leu Leu Lys Leu
465                 470

<210> SEQ ID NO 16
<211> LENGTH: 786
<212> TYPE: DNA
<213> ORGANISM: Homo sapiens

<400> SEQUENCE: 16
atgatcgaaa catacaacca aacttctccc cgatctgcgg ccactggact gcccatcagc    60
atgaaaattt ttatgtattt acttactgtt tttcttatca cccagatgat tgggtcagca   120 cttttgctg tgtatcttca tagaaggttg acaagatag aagatgaaag gaatcttcat    180 gaagatttg tattcatgaa acgatacag agatgcaaca caggagaaag atccttatcc    240
ttactgaact gtgaggagat taaaagccag tttgaaggct tgtgaagga tataatgtta    300 aacaaagagg agacgaagaa agaaacagc tttgaaatgc aaaaggtga tcagaatcct    360 caaattgcgg cacatgtcat aagtgaggcc agcagtaaaa caacatctgt gttacagtgg   420
gctgaaaaag gatactacac catgagcaac aacttggtaa ccctggaaaa tgggaaacag   480
ctgaccgtta aaagacaagg actctattat atctatgccc aagtcacctt ctgttccaat   540
cgggaagctt cgagtcaagc tccatttata gccagcctct gcctaaagtc ccccggtaga   600
ttcgagagaa tcttactcag agctgcaaat acccacagtt ccgccaaacc ttgcgggcaa   660
caatccattc acttgggagg agtatttgaa ttgcaaccag gtgcttcggt gtttgtcaat   720
gtgactgatc caagccaagt gagccatggc actggcttca cgtcctttgg cttactcaaa   780
ctctga                                                              786

<210> SEQ ID NO 17
<211> LENGTH: 261
<212> TYPE: PRT
<213> ORGANISM: Homo sapiens

<400> SEQUENCE: 17

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160
```

```
Leu Thr Val Lys Arg Gln Gly Leu Tyr Tyr Ile Tyr Ala Gln Val Thr
            165                 170                 175

Phe Cys Ser Asn Arg Glu Ala Ser Ser Gln Ala Pro Phe Ile Ala Ser
        180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 18
<211> LENGTH: 783
<212> TYPE: DNA
<213> ORGANISM: Mus musculus

<400> SEQUENCE: 18
atgatagaaa catacagcca accttccccc agatccgtgg caactggact tccagcgagc      60
atgaagattt ttatgtattt acttactgtt ttccttatca cccaaatgat tggatctgtg     120 cttttttgctg tgtatcttca tagaagattg ataaggtcg aagaggaagt aaaccttcat     180
gaagattttg tattcataaa aaagctaaag agatgcaaca aaggagaagg atctttatcc     240
ttgctgaact gtgaggagat gagaaggcaa tttgaagacc ttgtcaagga tataacgtta     300
aacaaagaag agaaaaaaga aaacagcttt gaaatgcaaa gaggtgatga ggatcctcaa     360
attgcagcac acgttgtaag cgaagccaac agtaatgcag catccgttct acagtgggcc     420
aagaaaggat attataccat gaaaagcaac ttggtaatgc ttgaaaatgg aaacagctg     480 acggttaaaa gagaaggact ctattatgtc tacactcaag tcaccttctg ctctaatcgg     540
gagccttcga gtcaacgccc attcatcgtc ggcctctggc tgaagcccag cagtggatct     600
gagagaatct tactcaaggc ggcaaatacc cacagttcct cccagctttg cgagcagcag     660
tctgttcact gggcggagt gtttgaatta caagctggtg cttctgtgtt tgtcaacgtg     720
actgaagcaa gccaagtgat ccacagagtt ggcttctcat cttttggctt actcaaactc     780
tga                                                                 783

<210> SEQ ID NO 19
<211> LENGTH: 260
<212> TYPE: PRT
<213> ORGANISM: Mus musculus

<400> SEQUENCE: 19

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Val Asn Leu His Glu Asp Phe Val
        50                  55                  60

Phe Ile Lys Lys Leu Lys Arg Cys Asn Lys Gly Glu Gly Ser Leu Ser
65                  70                  75                  80
```

Leu Leu Asn Cys Glu Glu Met Arg Arg Gln Phe Glu Asp Leu Val Lys
            85                  90                  95
Asp Ile Thr Leu Asn Lys Glu Lys Lys Glu Asn Ser Phe Glu Met
            100                 105                 110
Gln Arg Gly Asp Glu Asp Pro Gln Ile Ala Ala His Val Val Ser Glu
            115                 120                 125
Ala Asn Ser Asn Ala Ala Ser Val Leu Gln Trp Ala Lys Lys Gly Tyr
        130                 135                 140
Tyr Thr Met Lys Ser Asn Leu Val Met Leu Glu Asn Gly Lys Gln Leu
145                 150                 155                 160
Thr Val Lys Arg Glu Gly Leu Tyr Tyr Val Tyr Thr Gln Val Thr Phe
                165                 170                 175
Cys Ser Asn Arg Glu Pro Ser Ser Gln Arg Pro Phe Ile Val Gly Leu
            180                 185                 190
Trp Leu Lys Pro Ser Ser Gly Ser Glu Arg Ile Leu Leu Lys Ala Ala
            195                 200                 205
Asn Thr His Ser Ser Ser Gln Leu Cys Glu Gln Gln Ser Val His Leu
        210                 215                 220
Gly Gly Val Phe Glu Leu Gln Ala Gly Ala Ser Val Phe Val Asn Val
225                 230                 235                 240
Thr Glu Ala Ser Gln Val Ile His Arg Val Gly Phe Ser Ser Phe Gly
                245                 250                 255
Leu Leu Lys Leu
            260

<210> SEQ ID NO 20
<211> LENGTH: 930
<212> TYPE: DNA
<213> ORGANISM: Mus musculus

<400> SEQUENCE: 20

| | | | | | |
|---|---|---|---|---|---|
| atggatcagc | acacactgga | cgtggaggat | accgctgacg | ctaggcaccc | agctggcacc | 60 |
| tcctgccctt | ctgatgccgc | tctgctgcgc | gacacaggac | tgctggccga | tgccgctctg | 120 |
| ctgtctgaca | cagtgcggcc | aaccaacgcc | gctctgccaa | ccgatgctgc | ttaccctgct | 180 |
| gtgaacgtga | gggacagaga | ggctgcttgg | ccacctgccc | tgaacttctg | cagccgccac | 240 |
| cctaagctgt | acggctggt | ggccctggtg | ctgctgctgc | tgatcgctgc | ttgcgtgcca | 300 |
| atctttaccc | ggacagagcc | acgccccgct | ctgacaatca | ccacatcccc | caacctgggc | 360 |
| accagggaga | caacgccga | tcaggtgaca | ccagtgtctc | acatcggctg | ccccaacacc | 420 |
| acacagcagg | gaagcccagt | gttcgccaag | ctgctggcta | agaaccaggc | cagcctgtgc | 480 |
| aacaccacac | tgaactggca | cagccaggac | ggagctggaa | gctcctacct | gtcccagggc | 540 |
| ctgagatacg | aggaggataa | gaaggagctg | gtggtggact | ccctggact | gtactacgtg | 600 |
| ttcctggagc | tgaagctgtc | tccaaccttt | acaaacaccg | ccacaaggt | gcagggatgg | 660 |
| gtgtctctgg | tgctgcaggc | taagccccag | gtggacgatt | tcgataacct | ggccctgacc | 720 |
| gtggagctgt | tccttgtag | catggagaac | aagctggtgg | acaggtcttg | agccagctg | 780 |
| ctgctgctga | aggctggcca | caggctgtcc | gtgggactga | gagcctacct | gcacggcgcc | 840 |
| caggatgctt | acagagactg | ggagctgagc | taccctaaca | ccacatcctt | cggactgttt | 900 |
| ctggtgaagc | ctgacaaccc | atgggagtga | | | | 930 |

<210> SEQ ID NO 21

<211> LENGTH: 765
<212> TYPE: DNA
<213> ORGANISM: Homo sapiens

<400> SEQUENCE: 21

| | | | | | | |
|---|---|---|---|---|---|---|
| atggagtacg | cctctgacgc | cagcctggat | ccagaggccc | cttggccacc | tgcaccaagg | 60 |
| gcccgcgcct | gccgcgtgct | gccctgggcc | ctggtggccg | gcctgttatt | actgctgctg | 120 |
| ctggccgccg | cctgcgccgt | gttcctggca | tgtccttggg | ccgtgagcgg | agccagagcc | 180 |
| tccccaggct | ctgccgccag | ccctcggctg | agagagggac | cagagctgtc | cccagacgat | 240 |
| ccagcaggcc | tgctggacct | gaggcaggga | atgtttgccc | agctggtggc | ccagaacgtg | 300 |
| ctgctgatcg | acggccccct | gtcctggtac | tctgatcctg | gcctggccgg | cgtgtctctg | 360 |
| accggcggcc | tgagctataa | ggaggataca | aggagctggt | ggtggccaa | ggccggcgtg | 420 |
| tactacgtgt | tcttccagct | ggagctgagg | agagtggtgg | caggagaggg | ctctggaagc | 480 |
| gtgtccctgg | ccctgcacct | gcagcccctg | cggagcgccg | caggagccgc | cgccctggcc | 540 |
| ctgaccgtgg | acctgccacc | agccagctcc | gaggcaagga | attccgcctt | cggctttcag | 600 |
| ggcagactgc | tgcacctgtc | tgccggacag | aggctgggag | tgcacctgca | caccgaggcc | 660 |
| agggcccgcc | acgcatggca | gctgacccag | ggagcaacag | tgctgggcct | gttccgcgtg | 720 |
| acacctgaga | tcccagcagg | cctgcctagc | ccacggtccg | agtga | | 765 |

<210> SEQ ID NO 22
<211> LENGTH: 1389
<212> TYPE: DNA
<213> ORGANISM: Mus musculus

<400> SEQUENCE: 22

| | | | | | | |
|---|---|---|---|---|---|---|
| atgctgcctt | tcctgtccat | gctggtgctg | ctggtgcagc | cactgggcaa | cctgggagcc | 60 |
| gagatgaagt | ctctgagcca | gcgcagcgtg | cctaacacct | gcacactggt | catgtgctcc | 120 |
| cctacagaga | acggcctgcc | aggaagggac | ggaagagatg | gaaggagggac | accaagggga | 180 |
| gagaagggcg | acccccggact | gcctggacca | atgggactga | gcggcctgca | gggaccaacc | 240 |
| ggccccgtgg | gacctaaggg | agagaacgga | tccgctggag | agccaggacc | taagggagag | 300 |
| agaggactgt | ctggaccacc | tggactgcca | ggaatcccag | gaccagctgg | caaggaggga | 360 |
| ccatccggca | gcagggaaa | catcggacca | caggaaagc | ctggaccaaa | gggagaggct | 420 |
| ggacctaagg | gagaagtggg | cgccccagga | atgcagggct | ctacaggagc | taagggcagc | 480 |
| accggaccaa | agggagagag | gggagccccc | ggagtgcagg | gagcccctgg | caacgctgga | 540 |
| gccgctggcc | cagccggacc | cgctggccct | cagggagccc | ccggctctag | ggaccacca | 600 |
| ggcctgaagg | gagacagagg | cgtgcccgga | gatcggggca | tcaagggaga | gagcggcctg | 660 |
| cctgactccg | ccgctctgag | acagcagatg | gaggctctga | agggcaagct | gcagcggctg | 720 |
| gaggtggcct | ctctcccacta | ccagaaggcc | gctctgtttc | ctgacggaag | gacagagccc | 780 |
| aggcctgctc | tgaccatcac | cacatctcca | aacctgggca | aagagagaa | caacgccgat | 840 |
| caggtgaccc | ccgtgtctca | catcggatgc | cctaacacca | cacagcaggg | cagccccgtg | 900 |
| tttgccaagc | tgctggctaa | gaaccaggcc | agcctgtgca | acaccacact | gaactggcac | 960 |
| tcccaggatg | gcgccggaag | ctcctacctg | tctcagggcc | tgcggtacga | ggaggacaag | 1020 |
| aaggagctgg | tggtggatag | cccaggcctg | tactacgtgt | tcctggagct | gaagctgtcc | 1080 |
| cccacccttta | caaacaccgg | acacaaggtg | cagggatggg | tgagcctggt | gctgcaggct | 1140 |
| aagccccagg | tggacgattt | cgacaacctg | gccctgaccg | tggagctgtt | tccttgctct | 1200 |

| atggagaaca agctggtgga tagatcctgg agccagctgc tgctgctgaa ggctggacac | 1260 |
| cgcctgagcg tgggcctgag ggcttacctg cacggagctc aggacgctta cagggattgg | 1320 |
| gagctgtcct accctaacac cacatctttc ggcctgtttc tggtgaagcc agacaacccc | 1380 |
| tgggagtga | 1389 |

<210> SEQ ID NO 23
<211> LENGTH: 1389
<212> TYPE: DNA
<213> ORGANISM: Homo sapiens

<400> SEQUENCE: 23

| atgctgctgt tcctgctgtc cgccctggtg ctgctgaccc agcctctggg ctacctggag | 60 |
| gccgagatga agacctattc tcaccggaca atgccaagcg cctgcacact ggtcatgtgc | 120 |
| agcagcgtgg agtctggcct gccaggaagg gacggaaggg atggaaggga gggacctaga | 180 |
| ggcgagaagg gcgaccctgg cctgccagga gcagcaggac aggcaggaat gcccggccag | 240 |
| gccggccccg tgggacctaa gggcgacaac ggaagcgtgg agagccagg accaaagggc | 300 |
| gataccggcc cttccggacc acctggacca ccaggcgtgc ctggcccagc cggcagggag | 360 |
| ggccctctgg gcaagcaggg caatatcggc ccacagggca agcccggccc taagggcgag | 420 |
| gccgccccca gggcgaagt gggcgcccct ggcatgcagg aagcgccgg agcccgcggc | 480 |
| ctggccggac ctaagggcga gagaggcgtg cctggagaga ggggcgtgcc aggaaacaca | 540 |
| ggcgcagcag gatctgccgg agcaatggga ccccagggca gccctggcgc caggggccct | 600 |
| ccaggcctga agggcgacaa gggcatccca ggcgataagg gagcaaaggg agagagcggc | 660 |
| ctgccagatg tggcctccct cgccagcag gtggaggccc tgcagggcca ggtgcagcac | 720 |
| ctgcaggccg ccttctctca gtacaagaag gtggagctgt ttccaaacgg cgcctgcccc | 780 |
| tgggccgtga gcggagcccg ggcctcccca ggctctgccg ccagcctag gctgcgcgag | 840 |
| ggaccagagc tgagcccaga cgatccagca ggcctgctgg acctgagaca gggaatgttc | 900 |
| gcccagctgg tggcccagaa tgtgctgctg atcgacggcc cactgtcctg gtactctgat | 960 |
| ccaggcctgg ccggcgtgtc cctgaccggc ggcctgtctt ataaggagga tacaaaggag | 1020 |
| ctggtggtgg ccaaggccgg cgtgtactac gtgttcttcc agctggagct gaggagagtg | 1080 |
| gtggcaggag agggatccgg atctgtgagc ctggccctgc acctgcagcc cctgcggtcc | 1140 |
| gccgcaggag ccgccgccct ggccctgacc gtggacctgc acctgcctc tagcgaggca | 1200 |
| cgcaattccg ccttcggctt tcagggccgg ctgctgcacc tgtctgccgg acagagactg | 1260 |
| ggagtgcacc tgcacaccga ggcccgggcc agacacgcct ggcagctgac ccagggagca | 1320 |
| acagtgctgg gcctgtttag ggtgacacct gagatcccag ccggcctgcc aagccccgc | 1380 |
| tccgagtga | 1389 |

<210> SEQ ID NO 24
<211> LENGTH: 522
<212> TYPE: DNA
<213> ORGANISM: Mus musculus

<400> SEQUENCE: 24

| atggaggaga tgcctctgag ggagagctcc ccacagaggg ccgagagatg caagaagagc | 60 |
| tggctgctgt gcatcgtggc tctgctgctg atgctgctgt gctctctggg caccctgatc | 120 |
| tacacaagcc tgaagccaac cgccatcgag tcctgtatgg tgaagttcga gctgtctagc | 180 |

| | |
|---|---|
| tccaagtggc acatgacatc ccccaagcct cactgcgtga acaccacatc tgacggaaag | 240 |
| ctgaagatcc tgcagagcgg cacctacctg atctacggac aggtcatccc cgtggacaag | 300 |
| aagtacatca aggataacgc ccctttcgtg gtgcagatct acaagaagaa cgacgtgctg | 360 |
| cagacactga tgaacgattt tcagatcctg cccatcggcg agtgtacga gctgcacgct | 420 |
| ggcgacaaca tctacctgaa gttcaactcc aaggatcaca tccagaagac caacacatac | 480 |
| tggggaatca tcctgatgcc agatctgccc tttatctctt ga | 522 |

<210> SEQ ID NO 25
<211> LENGTH: 600
<212> TYPE: DNA
<213> ORGANISM: Homo sapiens

<400> SEQUENCE: 25

| | |
|---|---|
| atgaccctgc acccaagccc catcacatgc gagttcctgt tttctaccgc cctgatcagc | 60 |
| ccaaagatgt gcctgagcca cctggagaat atgcccctgt cccactctcg gacacaggga | 120 |
| gcccagagaa gctcctggaa gctgtggctg ttctgctcta tcgtgatgct gctgttcctg | 180 |
| tgcagctttt cctggctgat cttcatcttt ctgcagctgg agacagccaa ggagccttgc | 240 |
| atggccaagt ttggccctct gccatccaag tggcagatgg cctctagcga gccccttgc | 300 |
| gtgaacaagg tgagcgactg gaagctggag atcctgcaga acggcctgta cctgatctat | 360 |
| ggccaggtgg cccccaacgc caattacaac gacgtggccc ctttcgaggt gcggctgtat | 420 |
| aagaacaagg atatgatcca gaccctgaca aataagtcta agatccagaa cgtgggcggc | 480 |
| acatacgagc tgcacgtggg cgacaccatc gacctgatct tcaacagcga gcaccaggtg | 540 |
| ctgaagaaca atacatattg gggcatcatc ctgctggcca ccccagtt tatctcctga | 600 |

<210> SEQ ID NO 26
<211> LENGTH: 1164
<212> TYPE: DNA
<213> ORGANISM: Mus musculus

<400> SEQUENCE: 26

| | |
|---|---|
| atgctgcctt tcctgtctat gctggtgctg ctggtgcagc cactgggcaa cctgggagcc | 60 |
| gagatgaaga gcctgtccca gagatccgtg cccaacacct gcacactggt catgtgctct | 120 |
| cctaccgaga acggcctgcc aggaagggac ggaagagatg gaaggaggg acctcgggga | 180 |
| gagaagggcg acccaggact gcctggacca atgggactga gcggcctgca gggaccaaca | 240 |
| ggccccgtgg gacctaaggg agagaacgga agcgccggag agccaggacc taagggagag | 300 |
| agggactgt ccggaccacc tggactgcct ggaatcccag gaccagctgg caaggaggga | 360 |
| ccatccggca gcagggaaa catcggacca caggaaagc ctggaccaaa gggagaggct | 420 |
| ggaccaaagg gagaagtggg cgctcctgga atgcagggct ccaccggagc caagggctct | 480 |
| acaggaccaa aggagagag gggagctccc ggagtgcagg gagcccctgg caacgctgga | 540 |
| gccgctggcc cagccggacc cgctggccct caggagcc caggcagcag ggaccaccc | 600 |
| ggcctgaagg gcgacagggg cgtgccagga gataggggca tcaagggaga gtctggcctg | 660 |
| ccagacagcg ccgctctgag acagcagatg gaggccctga agcaagct gcagcggctg | 720 |
| gaggtggctt ctctcccacta ccagaaggcc gctctgtttc cagatggcag cctgaagccc | 780 |
| accgccatcg agtcctgcat ggtgaagttt gagctgagct cctctaagtg gcacatgaca | 840 |
| tctcccaagc tcactgcgt gaacaccaca tctgacggca agctgaagat cctgcagagc | 900 |
| ggcacctacc tgatctacgg ccaggtcatc cccgtggaca agaagtacat caaggataac | 960 |

| | | |
|---|---|---|
| gcccctttcg tggtgcagat ctacaagaag aacgacgtgc tgcagacact gatgaacgat | | 1020 |
| tttcagatcc tgccaatcgg cggagtgtac gagctgcacg ctggcgacaa catctacctg | | 1080 |
| aagttcaact ctaaggatca catccagaag accaacacat actggggcat catcctgatg | | 1140 |
| ccagatctgc cctttatcag ctga | | 1164 |

<210> SEQ ID NO 27
<211> LENGTH: 1152
<212> TYPE: DNA
<213> ORGANISM: Homo sapiens

<400> SEQUENCE: 27

| | | |
|---|---|---|
| atgctgctgt tcctgctgtc tgccctggtg ctgctgaccc agccactggg ctacctggag | | 60 |
| gccgagatga agacctattc ccaccgcaca atgccttctg cctgcacact ggtcatgtgc | | 120 |
| agcagcgtgg agagcggcct gccaggaagg gacggaagag atggaaggga gggacccaga | | 180 |
| ggcgagaagg gcgaccctgg cctgccagga gcagcaggac aggcaggaat gccaggccag | | 240 |
| gccggccccg tgggccctaa gggcgacaat ggatccgtgg gagagccagg accaaagggc | | 300 |
| gataccggcc cttctggacc acctggacca caggcgtgc ctggaccagc aggaagagag | | 360 |
| ggacctctgg gcaagcaggg aaacatcgga ccacagggca agccaggccc taagggcgag | | 420 |
| gccgccccca gggcgaagt gggcgcccct ggcatgcagg gatccgccgg agccaggggc | | 480 |
| ctggccggac ctaagggcga gcgcggcgtg cctggagaga gggcgtgcc aggaaataca | | 540 |
| ggcgcagcag gatctgccgg agcaatggga ccacagggca gccccggcgc cagaggccct | | 600 |
| ccaggcctga agggcgacaa gggaatccct ggcgataagg gagcaaaggg agagagcggc | | 660 |
| ctgccagacg tggcctccct gaggcagcag gtggaggccc tgcagggaca ggtgcagcac | | 720 |
| ctgcaggccg ccttcagcca gtacaagaag gtggagctgt tcccaaatgg cgagacagcc | | 780 |
| aaggagccct gcatggccaa gttcggccca ctgccagca agtggcagat ggcctctagc | | 840 |
| gagccccctt gcgtgaacaa ggtgagcgat tggaagctgg agatcctgca gaacggcctg | | 900 |
| tacctgatct atggccaggt ggccccaac gccaattaca cgacgtggc ccttttgag | | 960 |
| gtgcggctgt ataagaacaa ggatatgatc cagaccctga caaataagtc taagatccag | | 1020 |
| aacgtgggag gcacctacga gctgcacgtg ggcgacacaa tcgacctgat cttcaacagc | | 1080 |
| gagcaccagg tgctgaagaa caatacatat tggggcatca tcctgctggc caaccccag | | 1140 |
| tttatctcct ga | | 1152 |

<210> SEQ ID NO 28
<211> LENGTH: 597
<212> TYPE: DNA
<213> ORGANISM: Mus musculus

<400> SEQUENCE: 28

| | | |
|---|---|---|
| atggagggcg agggagtgca gcccctggat gagaacctgg agaacggctc ccggcctcgc | | 60 |
| ttcaagtgga agaagaccct gcggctggtg gtgtctggaa tcaagggcgc cggaatgctg | | 120 |
| ctgtgcttta tctacgtgtg cctgcaggctg agctcctctc ccgccaagga tccccctatc | | 180 |
| cagaggctga gaggagctgt gaccaggtgc gaggacggac agctgttcat cagctcctac | | 240 |
| aagaacgagt accagacaat ggaggtgcag aacaacagcg tggtcatcaa gtgtgatggc | | 300 |
| ctgtacatca tctacctgaa gggatccttc tttcaggagg tgaagatcga cctgcacttt | | 360 |
| cgggaggatc acaacccaat ctctatcccc atgctgaacg acggcaggag aatcgtgttc | | 420 |

| | |
|---|---|
| acagtggtgg ccagcctggc ttttaaggac aaggtgtacc tgaccgtgaa cgccccagat | 480 |
| acactgtgcg agcacctgca gatcaacgac ggagagctga tcgtggtgca gctgacccct | 540 |
| ggctactgtg ctccagaggg atcttaccac agcacagtga accaggtgcc cctgtga | 597 |

<210> SEQ ID NO 29
<211> LENGTH: 552
<212> TYPE: DNA
<213> ORGANISM: Homo sapiens

<400> SEQUENCE: 29

| | |
|---|---|
| atggagaggg tgcagcccct ggaggagaac gtgggaaatg ccgcccggcc tagattcgag | 60 |
| aggaacaagc tgctgctggt ggcctctgtg atccagggcc tgggcctgct gctgtgcttc | 120 |
| acctacatct gtctgcactt ttctgccctg caggtgagcc acagataccc ccgcatccag | 180 |
| agcatcaagg tgcagttcac cgagtataag aaggagaagg ctttatcct gacatcccag | 240 |
| aaggaggacg agatcatgaa ggtgcagaac aattctgtga tcatcaactg cgatggcttc | 300 |
| tacctgatct ccctgaaggg ctattttct caggaagtga atatcagcct gcactatcag | 360 |
| aaggacgagg agccactgtt tcagctgaag aaggtgcgga gcgtgaattc cctgatggtg | 420 |
| gccagcctga cctacaagga caaggtgtat ctgaacgtga ccacagataa tacatccctg | 480 |
| gacgatttcc acgtgaacgg cggcgagctg atcctgatcc accagaatcc cggcgagttt | 540 |
| tgcgtgctgt ga | 552 |

<210> SEQ ID NO 30
<211> LENGTH: 1215
<212> TYPE: DNA
<213> ORGANISM: Mus musculus

<400> SEQUENCE: 30

| | |
|---|---|
| atgctgccct tcctgtccat gctggtgctg ctggtgcagc tctgggcaa cctgggagcc | 60 |
| gagatgaagt ctctgagcca gagatccgtg ccaaacacct gcacactggt catgtgctct | 120 |
| cccaccgaga acggcctgcc tggaagggac ggaagagatg aagggaggg accccgggga | 180 |
| gagaagggcg atcctggact gccaggacct atgggactga gcggcctgca gggaccaaca | 240 |
| ggccccgtgg gacctaaggg agagaacgga agcgccggag agccaggacc aaagggagag | 300 |
| aggggactgt ccgccccacc tggactgcct ggaatccctg accagctggg caaggaggga | 360 |
| ccttccggca agcagggaaa catcggacca cagggaaagc caggacctaa gggagaggct | 420 |
| ggaccaaagg gagaagtggg cgctcccgga atgcagggct ctaccggagc caagggcagc | 480 |
| acaggaccta agggagagag gggagctcca ggagtgcagg gagccccgg caacgctgga | 540 |
| gctgctggac cagctggacc agctggccct caggagccc caggctctag ggaccacca | 600 |
| ggcctgaagg gcgacagggg cgtgccagga gataggggca tcaagggaga gagcggcctg | 660 |
| ccagattccg ccgctctgag acagcagatg gaggccctga agggcaagct gcagcggctg | 720 |
| gaggtggctt tcagccacta ccagaaggcc gctctgtttc ctgacggcag ctcctctcca | 780 |
| gccaaggatc ctccaatcca gcggctgcgc ggagctgtga ccaggtgcga ggatggccag | 840 |
| ctgttcatca gctcctacaa gaacgagtac cagacaatgg aggtgcagaa caactctgtg | 900 |
| gtcatcaagt gtgacggcct gtacatcatc tacctgaagg gcagcttctt tcaggaggtg | 960 |
| aagatcgacc tgcactttag agaggataca aacccaatct ccatccccat gctgaacgac | 1020 |
| ggcaggagaa tcgtgttcac cgtggtgcc tctctggctt ttaaggacaa ggtgtacctg | 1080 |
| accgtgaacg ccccgatac actgtgcgag cacctgcaga tcaacgacgg cgagctgatc | 1140 |

| gtggtgcagc tgacccctgg atactgtgct ccagagggct cctaccactc tacagtgaac | 1200 |
| caggtgcctc tgtga | 1215 |

<210> SEQ ID NO 31
<211> LENGTH: 1170
<212> TYPE: DNA
<213> ORGANISM: Homo sapiens

<400> SEQUENCE: 31

| atgctgctgt tcctgctgag cgccctggtg ctgctgaccc agccactggg ctacctggag | 60 |
| gccgagatga agacctattc ccacagaaca atgccttctg cctgcacact ggtcatgtgc | 120 |
| agcagcgtgg agtccggcct gccaggaagg gacggcagag atggcaggga gggccccagg | 180 |
| ggcgagaagg gcgaccccgg cctgcctgga gcagcaggcc aggccggcat gccaggccag | 240 |
| gccggcccag tgggccccaa gggcgacaac ggcagcgtgg gcgagcccgg ccctaagggc | 300 |
| gataccggcc cctccggccc ccctggccca cccggcgtgc caggaccagc aggaagggag | 360 |
| ggaccactgg gcaagcaggg caatatcgga cctcagggca agcctggacc aaagggagag | 420 |
| gcaggaccaa agggagaagt gggcgcccct ggcatgcagg gatctgccgg agcccggggc | 480 |
| ctggccggcc ccaagggcga gagaggcgtg cccggcgaga gggcgtgcc tggcaacaca | 540 |
| ggcgccgccg gctccgccgg cgccatggga cctcagggct ctccaggagc cagaggccct | 600 |
| ccaggcctga agggcgacaa gggaatccct ggcgataagg gagcaagggg agagagcggc | 660 |
| ctgccagacg tggcctccct gcggcagcag gtggaggccc tgcagggcca ggtgcagcac | 720 |
| ctgcaggccg ccttcagcca gtacaagaag gtggagctgt ttcctaatgg cgtgtctcac | 780 |
| cgctacccac ggatccagag catcaaggtg cagttcaccg agtataagaa ggagaagggc | 840 |
| tttatcctga catctcagaa ggaggacgag atcatgaagg tgcagaacaa tagcgtgatc | 900 |
| atcaactgcg atggcttcta cctgatcagc ctgaagggct attttcccca ggaagtgaat | 960 |
| atctctctgc actatcagaa ggatgaggag cctctgtttc agctgaagaa ggtgagatct | 1020 |
| gtgaacagcc tgatggtggc ctccctgacc tacaaggaca aggtgtatct gaacgtgacc | 1080 |
| acagataata catctctgga cgatttccac gtgaacggcg cgagctgat cctgatccac | 1140 |
| cagaatcccg gcgagttttg cgtgctgtga | 1170 |

<210> SEQ ID NO 32
<211> LENGTH: 969
<212> TYPE: DNA
<213> ORGANISM: Mus musculus

<400> SEQUENCE: 32

| atgcagctga agtgtccatg cttcgtgtcc ctgggaacaa gacagcccgt ctggaagaaa | 60 |
| ctgcacgtga gctccggctt ctttagcggc ctggggctgt ttctgctgct gctgtctagt | 120 |
| ctgtgcgccg cttccgcaga gactgaagtc ggagccatgg tgggcagtaa cgtggtcctg | 180 |
| tcatgcatcg acccacaccg acggcatttc aacctgtctg gcctgtacgt gtattggcag | 240 |
| attgagaatc ccgaagtgtc agtcacctac tatctgcctt acaagagccc agggatcaac | 300 |
| gtggactcaa gctataaaaa tagggggcac ctgtccctgg attctatgaa gcagggaaac | 360 |
| ttcagcctgt acctgaaaaa tgtgacccct caggacacac aggagttcac ttgtcgcgtc | 420 |
| tttatgaaca ctgcaaccga actggtgaag attctggagg aagtggtccg gctgagagtc | 480 |
| gcagccaact ttagcactcc tgtgatctct accagtgatt cctctaatcc aggccaggag | 540 |

| | |
|---|---|
| cggacatata cttgcatgtc taagaacgga taccccgaac ctaatctgta ttggatcaac | 600 |
| accacagaca atagtctgat tgataccgct ctgcagaaca atacagtcta cctgaacaag | 660 |
| ctggggctgt atgacgtgat ctctactctg cggctgccat ggaccagtag aggagatgtg | 720 |
| ctgtgctgcg tggagaacgt ggccctgcac cagaatatca cctcaattag ccaggctgag | 780 |
| tcctttaccg gcaacaatac aaagaatcct caggagacac ataacaatga actgaaagtg | 840 |
| ctggtgccag tgctggccgt cctggctgca gcagctttcg tgtcttttat catctacaga | 900 |
| aggacccgcc ctcaccgctc atacactgga cctaagaccg tgcagctgga actgacagac | 960 |
| catgcttga | 969 |

<210> SEQ ID NO 33
<211> LENGTH: 909
<212> TYPE: DNA
<213> ORGANISM: Homo sapiens

<400> SEQUENCE: 33

| | |
|---|---|
| atgcgtctgg gttcacctgg tctgctgttt ctgctgtttt caagtctgcg tgctgatact | 60 |
| caggagaagg aagtccgggc tatggtcgga agtgacgtgg agctgtcatg cgcttgtccc | 120 |
| gaagggtccc ggttcgacct gaacgatgtc tacgtgtatt ggcagacctc tgagagtaag | 180 |
| accgtggtca cataccacat ccctcagaac tccagcctgg aaaatgtgga ttcaaggtat | 240 |
| cggaacagag ccctgatgtc ccctgctggc atgctgcggg gagacttctc tctgagactg | 300 |
| tttaatgtga caccacagga tgagcagaaa ttccattgcc tggtcctgtc acagtccctg | 360 |
| ggatttcagg aggtgctgag tgtcgaagtg actctgcacg tcgccgctaa tttctccgtg | 420 |
| cctgtggtca gcgcaccaca tagcccctct caggacgagc tgacctttac atgtacttcc | 480 |
| atcaacggct acccccgccc taacgtgtac tggattaaca agactgacaa tagcctgctg | 540 |
| gatcaggcac tgcagaacga caccgtgttt ctgaatatgc gaggactgta cgatgtggtc | 600 |
| agcgtcctgc gtattgccag gaccccatct gtgaacatcg ggtgctgtat tgagaacgtc | 660 |
| ctgctgcagc agaatctgac agtggggagc cagactggta atgacatcgg cgagagggat | 720 |
| aagattaccg aaaaccccgt gagtacaggc gagaagaacg cagccacatg gtcaatcctg | 780 |
| gctgtgctgt gcctgctggt ggtcgtggct gtcgcaattg gctgggtgtg ccgcgatcgg | 840 |
| tgtctgcagc actcttatgc cggtgcttgg gcagtgagtc cagagactga actgaccggc | 900 |
| catgtctaa | 909 |

<210> SEQ ID NO 34
<211> LENGTH: 1574
<212> TYPE: DNA
<213> ORGANISM: Mus musculus

<400> SEQUENCE: 34

| | |
|---|---|
| cttaagatgg aaactgatac tctgctgctc tgggtgctgc tcctctgggt gcctggttca | 60 |
| actgggaca ttcgacgggc tgacattgtg atgacccaga ccacactgag cctgcccgtg | 120 |
| tccctgggcg accaggccag catctcctgc cggagctccc agtctatcgt gcacagcaac | 180 |
| ggaaacacat acctggagtg gtatctgcag aagcctggcc agtccccaaa gctgctgatc | 240 |
| tacaaggtgt ccaacaggtt cagcggcgtg cctgaccgct tttctggaag cggctccgga | 300 |
| acagatttca cactgaagat cagcagggtg gaggctgagg acctgggcgt gtactactgc | 360 |
| ttccaggat cccacgtgcc ttacaccttt ggcgaggca caaagctgga gatcaagaga | 420 |
| gccgatgctg ctccaaccgt gtctggaagc ggaggcgggg gttctggagg cggtgggagc | 480 |

```
ggtggcggag ggtctgaggc taagctgcag gagagcggcc ccgtgctggt gaagcctgga      540
gccagcgtga agatgtcctg taaggcttct ggatacacct tcacagacta ctacatgaac      600
tgggtgaagc agagccacgg caagtccctg gagtggatcg gagtgatcaa cccttacaac      660
ggcgacacct cttacaacca gaagtttaag ggcaaggcca ccctgacagt ggataagtct      720
agctccaccg cttacatgga gctgaacagc ctgacatccg aggattctgc cgtgtactac      780
tgtgctaggt actacggaag ctggttcgcc tactggggcc agggaacact gatcaccgtg      840
tccacagcca agaccacacc ccctagcgtg taccccctgg ctcctaggtc tagcagaggc      900
tgcaagccat gcatctgtac cgtgcccgag gtgagcagcg tgttcatctt ccacccaag      960 cccaaggacg tgctgaccat cacactgacc cctaaggtga catgcgtggt ggtggatatc     1020
agcaaggacg atccagaggt gcagttctcc tggtttgtgg acgatgtgga ggtgcacacc     1080
gcccagacac agccaaggga ggagcagttc aactccacct ttagatccgt gtctgagctg     1140
cccatcatgc accaggactg gctgaacgga aaggagttca gtgccgggt gaactccgcc     1200 gcttttcctg ctccaatcga gaagaccatc tctaagacaa agggccgccc aaaggctcca     1260
caggtgtaca ccatccctcc acccaaggag cagatggcta aggataaggt gagcctgacc     1320
tgtatgatca cagacttctt ccccgaggat atcacagtgg agtggcagtg aacggacag     1380 cctgccgaga actacaagaa cacccagcca atcatggaca cagatggctc ttacttcgtg     1440
tacagcaagc tgaacgtgca gaagtctaac tgggaggctg gcaacacctt cacctgcagc     1500
gtgctgcacg aaggtctcca taatcaccac accgaaaaga gcctcagtca cagccctggg     1560
aaatgaggcg cgcc                                                      1574

<210> SEQ ID NO 35
<211> LENGTH: 1484
<212> TYPE: DNA
<213> ORGANISM: Homo sapiens

<400> SEQUENCE: 35
cttaagatgg aaactgacac cctgctgctg tgggtcctgc tgctgtgggt gcctggatcc       60
accggcgata tcgtgctgac ccagtctcct ggcacactga gtctgtcacc aggggagcga      120
gcaacactgt cttgtagagc cagccagtct gtgggaagct cctacctggc ttggtatcag      180
cagaagccag gccaggcacc caggctgctg atctacggag ccttcagccg ggccactggc      240
attccagaca ggttctctgg aagtggctca gggaccgact caccctgac catcagccga      300 ctggagcccg aagacttcgc cgtgtactat tgccagcagt acggctctag tccttggact      360
tttggacagg gcaccaaagt ggagatcaag cgcggcgggg gaggctctgg gggaggcggg      420 agtgaggcg gggatcaca ggtccagctg gtggaaagcg gcggggagt ggtccagcca      480 ggccggagcc tgcggctgag ctgcgccgct tcaggattca cattttcaag ctataccatg      540
cactgggtcc ggcaggcacc agggaaggga ctggagtggg tgaccttcat cagctatgac      600
ggcaacaaca gtattacgc tgattccgtg aaagggaggt ttaccattag ccgcgacaac      660
tccaaaaata cactgtacct gcagatgaac agcctgcggg ccgaggatac tgctatctac      720
tattgcgcaa gaaccgggtg gctgggaccc ttcgactatt ggggccaggg gactctggtc      780
accgtgtcct ctgataagac acacacatgc cctccctgtc ctgcaccaga gctgctgggc      840
gggccatccg tgttcctgtt tccacccaag cctaaagaca ccctgatgat cagccggaca      900
cctgaagtca cttgcgtggt cgtggacgtg agtcacgagg atccagaagt caagtttaac      960
```

```
tggtacgtgg atggcgtcga ggtgcataat gccaagacca aacctcgcga ggaacagtac   1020
aatagcacat atcgagtcgt gtccgtcctg actgtgctgc atcaggattg gctgaacggc   1080
aaagagtata agtgcaaagt gagcaataag gcactgcctg ccccaatcga gaaacaatt    1140 tccaaggcta aaggccagcc cagggaacct caggtgtaca ctctgcctcc aagtcgcgag   1200
gaaatgacca agaaccaggt gagcctgacc tgtctggtga aagggttcta tccatcagac   1260
attgcagtgg agtgggaaag caatggacag cccgaaaaca attacaagac cacaccccct   1320
gtgctggaca gcgatggctc cttctttctg tattctaagc tgactgtgga taaaagtcgc   1380
tggcagcagg ggaacgtctt tagctgttcc gtgatgcatg aggctctgca caatcattac   1440
acacagaagt ctctgagtct gtcacccggc aaatgaggcg cgcc                   1484

<210> SEQ ID NO 36
<211> LENGTH: 632
<212> TYPE: DNA
<213> ORGANISM: Artificial Sequence
<220> FEATURE:
<223> OTHER INFORMATION: CMV promoter

<400> SEQUENCE: 36
gttgacattg attattgact agttattaat agtaatcaat tacggggtca ttagttcata   60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccattgacgc   540
aaatgggcgg taggcgtgta cggtgggagg tctatataag cagagctctc tggctaacta   600
gagaacccac tgcttactgg cttatcgaaa tt                                 632

<210> SEQ ID NO 37
<211> LENGTH: 394
<212> TYPE: DNA
<213> ORGANISM: Artificial Sequence
<220> FEATURE:
<223> OTHER INFORMATION: RSV promoter

<400> SEQUENCE: 37
tgtacgggcc agatatacgc gtatctgagg ggactagggt gtgtttaggc gaaaagcggg   60
gcttcggttg tacgcggtta ggagtcccct caggatatag tagtttcgct tttgcatagg   120
gagggggaaa tgtagtctta tgcaatacac ttgtagtctt gcaacatggt aacgatgagt   180
tagcaacatg ccttacaagg agagaaaaag caccgtgcat gccgattggt ggaagtaagg   240
tggtacgatc gtgccttatt aggaaggcaa cagacaggtc tgacatggat tggacgaacc   300
actgaattcc gcattgcaga gataattgta tttaagtgcc tagctcgata caataaacgc   360
catttgacca ttcaccacat tggtgtgcac ctcc                              394

<210> SEQ ID NO 38
<211> LENGTH: 188
<212> TYPE: DNA
<213> ORGANISM: Artificial Sequence
```

<220> FEATURE:
<223> OTHER INFORMATION: BGH polyA

<400> SEQUENCE: 38

```
ctgtgccttc tagttgccag ccatctgttg tttgcccctc cccgtgcctt ccttgaccc       60 tggaaggtgc cactcccact gtcctttcct aataaaatga ggaaattgca tcgcattgtc      120
tgagtaggtg tcattctatt ctggggggtg ggtggggca ggacagcaag ggggaggatt       180
gggaagac                                                               188
```

<210> SEQ ID NO 39
<211> LENGTH: 249
<212> TYPE: DNA
<213> ORGANISM: Artificial Sequence
<220> FEATURE:
<223> OTHER INFORMATION: SV40 late polyA

<400> SEQUENCE: 39

```
gacatgataa gatacattga tgagtttgga caaaccacaa ctagaatgca gtgaaaaaaa       60
tgctttattt gtgaaatttg tgatgctatt gctttatttg tgaaatttgt gatgctattg      120
ctttatttgt aaccattata agctgcaata acaagttaa caacaacaat tgcattcatt       180
ttatgtttca ggttcagggg gaggtgtggg aggttttta aagcaagtaa aacctctaca       240
aatgtggta                                                              249
```

<210> SEQ ID NO 40
<211> LENGTH: 345
<212> TYPE: DNA
<213> ORGANISM: Artificial Sequence
<220> FEATURE:
<223> OTHER INFORMATION: SV40 enhancer promoter

<400> SEQUENCE: 40

```
gctgtggaat gtgtgtcagt tagggtgtgg aaagtcccca ggctcccag caggcagaag        60 tatgcaaagc atgcatctca attagtcagc aaccaggtgt ggaaagtccc caggctcccc     120
agcaggcaga agtatgcaaa gcatgcatct caattagtca gcaaccatag tcccgcccct     180
aactccgccc atcccgcccc taactccgcc cagttccgcc cattctccgc cccatggctg     240
actaattttt tttatttatg cagaggccga ggccgcctcg gcctctgagc tattccagaa     300
gtagtgagga ggcttttttg gaggcctagg cttttgcaaa aagct                      345
```

<210> SEQ ID NO 41
<211> LENGTH: 99
<212> TYPE: DNA
<213> ORGANISM: Artificial Sequence
<220> FEATURE:
<223> OTHER INFORMATION: Rabbit beta-globin polyA

<400> SEQUENCE: 41

```
gacctctggc taataaagga aatttatttt cattgcaata gtgtgttgga attttttgtg       60
tctctcactc ggaaggacat atgggagggc aaatcattt                              99
```

<210> SEQ ID NO 42
<211> LENGTH: 723
<212> TYPE: DNA
<213> ORGANISM: Artificial Sequence
<220> FEATURE:
<223> OTHER INFORMATION: GFP

<400> SEQUENCE: 42

```
accatggtga gcaagggcga ggagctgttc accggggtgg tgcccatcct ggtcgagctg      60
gacggcgacg taaacggcca caagttcagc gtgtccggcg agggcgaggg cgatgccacc     120
tacggcaagc tgaccctgaa gttcatctgc accaccggca agctgcccgt gccctggccc     180
accctcgtga ccaccctgac ctacggcgtg cagtgcttca gccgctaccc cgaccacatg     240
aagcagcacg acttcttcaa gtccgccatg cccgaaggct acgtccagga gcgcaccatc     300
ttcttcaagg acgacggcaa ctacaagacc cgcgccgagg tgaagttcga gggcgacacc     360
ctggtgaacc gcatcgagct gaagggcatc gacttcaagg aggacggcaa catcctgggg     420
cacaagctgg agtacaacta caacagccac aacgtctata tcatggccga caagcagaag     480
aacggcatca aggtgaactt caagatccgc cacaacatcg aggacggcag cgtgcagctc     540
gccgaccact accagcagaa cacccccatc ggcgacggcc ccgtgctgct gcccgacaac     600
cactacctga gcacccagtc cgccctgagc aaagacccca acgagaagcg cgatcacatg     660
gtcctgctgg agttcgtgac cgccgccggg atcactctcg gcatggacga gctgtacaag     720
taa                                                                  723

<210> SEQ ID NO 43
<211> LENGTH: 454
<212> TYPE: DNA
<213> ORGANISM: Artificial Sequence
<220> FEATURE:
<223> OTHER INFORMATION: MoMuLV LTR

<400> SEQUENCE: 43
ttaattaagt aacgccattt tgcaaggcat ggaaaaatac ataactgaga atagagaagt      60
tcagatcaag gtcaggaaca gatggaacag ctgaatatgg gccaaacagg atatctgtgg     120
taagcagttc ctgccccggc tcagggccaa gaacagatgg aacagctgaa tatgggccaa     180
acaggatatc tgtggtaagc agttcctgcc ccggctcagg gccaagaaca gatggtcccc     240
agatgcggtc cagccctcag cagtttctag agaaccatca gatgtttcca gggtgcccca     300
aggacctgaa atgaccctgt gccttatttg aactaaccaa tcagttcgct tctcgcttct     360
gttcgcgcgc ttctgctccc cgagctcaat aaaagagccc acaaccnctc actcggggcg     420
ccagtcctcc gattgactga gtcgcccgct taag                                454

<210> SEQ ID NO 44
<211> LENGTH: 1349
<212> TYPE: DNA
<213> ORGANISM: Artificial Sequence
<220> FEATURE:
<223> OTHER INFORMATION: EF1alpha promoter

<400> SEQUENCE: 44
ttaattaaga gtaattcata caaaaggact cgcccctgcc ttggggaatc ccagggaccg      60
tcgttaaact cccactaacg tagaacccag atcgctgcg ttcccgcccc ctcacccgc       120 ccgctctcgt catcactgag gtggagaaga gcatgcgtga ggctccggtg cccgtcagtg     180
ggcagagcgc acatcgccca cagtccccga aagttgggg ggaggggtcg gcaattgaac      240
cggtgcctag agaaggtggc gcggggtaaa ctgggaaagt gatgtcgtgt actggctccg     300
ccttttttcc gagggtgggg gagaaccgta tataagtgca gtagtcgccg tgaacgttct     360
ttttcgcaac gggtttgccg ccagaacaca ggtaagtgcc gtgtgtggtt cccgcgggcc     420
tggcctcttt acgggttatg gcccttgcgt gccttgaatt acttccacgc ccctggctgc     480
agtacgtgat tcttgatccc gagcttcggg ttggaagtgg gtgggagagt tcgaggcctt     540
```

-continued

```
gcggttaagg agcccttcg cctcgtgctt gagttgaggc ctggcttggg cgctggggcc     600
gccgcgtgcg aatctggtgg caccttcgcg cctgtctcgc tgctttcgat aagtctctag    660
ccatttaaaa ttttgatga cctgctgcga cgcttttttt ctggcaagat agtcttgtaa    720
atgcgggcca agatctgcac actggtattt cggttttgg ggccgcgggc ggcgacgggg    780
cccgtgcgtc ccagcgcaca tgttcggcga ggcggggcct gcgagcgcgg ccaccgagaa    840
tcggacgggg gtagtctcaa gctggccggc ctgctctggt gcctggcctc gcgccgccgt    900
gtatcgcccc gccctgggcg gcaaggctgg cccggtcggc accagttgcg tgagcggaaa    960
gatggccgct tcccggccct gctgcaggga gctcaaaatg gaggacgcgg cgctcggag    1020 agcgggcggg tgagtcaccc acacaaagga aaagggcctt tccgtcctca gccgtcgctt   1080
catgtgactc cacggagtac cgggcgccgt ccaggcacct cgattagttc tcgagctttt   1140
ggagtacgtc gtctttaggt tgggggagg ggttttatgc gatggagttt ccccacactg   1200
agtgggtgga gactgaagtt aggccagctt ggcacttgat gtaattctcc ttggaatttg   1260 cccttttga gtttggatct tggttcattc tcaagcctca gacagtggtt caaagttttt    1320
ttcttccatt tcaggtgtcg tgacttaag                                     1349
```

<210> SEQ ID NO 45
<211> LENGTH: 481
<212> TYPE: DNA
<213> ORGANISM: Artificial Sequence
<220> FEATURE:
<223> OTHER INFORMATION: HGH polyA

<400> SEQUENCE: 45

```
gacgggtggc atccctgtga cccctcccca gtgcctctcc tggccctgga agttgccact      60
ccagtgccca ccagccttgt cctaataaaa ttaagttgca tcattttgtc tgactaggtg    120
tccttctata atattatggg gtggagggg gtggtatgga gcaaggggca agttgggaag    180
acaacctgta gggcctgcgg ggtctattgg gaaccaagct ggagtgcagt ggcacaatct    240
tggctcactg caatctccgc ctcctgggtt caagcgattc tcctgcctca gcctcccgag    300
ttgttgggat tccaggcatg catgaccagg ctcagctaat ttttgttttt ttggtagaga    360
cggggtttca ccatattggc caggctggtc tccaactcct aatctcaggt gatctaccca    420
ccttggcctc ccaaattgct gggattacag gcgtgaacca ctgctccctt ccctgtcctt    480
t                                                                     481
```